(12) United States Patent
Dull et al.

(10) Patent No.: US 10,508,096 B2
(45) Date of Patent: Dec. 17, 2019

(54) NICOTINE SALTS, CO-CRYSTALS, AND SALT CO-CRYSTAL COMPLEXES

(71) Applicant: R.J. Reynolds Tobacco Company, Winston-Salem, NC (US)

(72) Inventors: Gary M. Dull, Lewisville, NC (US); Susana del Rio Gancedo, Cambridge (GB); Judit Galcera Julia, Sant Just Desvern (ES)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 0 days.

(21) Appl. No.: 15/695,227

(22) Filed: Sep. 5, 2017

(65) Prior Publication Data

US 2018/0051002 A1  Feb. 22, 2018

Related U.S. Application Data

(63) Continuation-in-part of application No. 15/671,722, filed on Aug. 8, 2017, which is a continuation of application No. 14/721,283, filed on May 26, 2015, now Pat. No. 9,738,622.

(60) Provisional application No. 62/003,295, filed on May 27, 2014.

(51) Int. Cl.
```
C07D 401/04    (2006.01)
A61K 9/00      (2006.01)
C07C 65/11     (2006.01)
A24B 15/38     (2006.01)
C07C 65/03     (2006.01)
A24B 13/00     (2006.01)
A61M 15/06     (2006.01)
A61M 11/04     (2006.01)
A24F 47/00     (2006.01)
```

(52) U.S. Cl.
CPC ............ *C07D 401/04* (2013.01); *A24B 13/00* (2013.01); *A24B 15/38* (2013.01); *A61K 9/0056* (2013.01); *C07C 65/03* (2013.01); *C07C 65/11* (2013.01); *A24F 47/008* (2013.01); *A61M 11/042* (2014.02); *A61M 15/06* (2013.01); *A61M 2205/8206* (2013.01); *C07B 2200/13* (2013.01)

(58) Field of Classification Search
CPC .................................................. C07D 401/04
USPC ........................................ 546/279.4; 514/343
See application file for complete search history.

(56) References Cited

U.S. PATENT DOCUMENTS

| | | |
|---|---|---|
| 2,033,909 A | 3/1936 | Cox et al. |
| 2,822,306 A | 2/1958 | Thienemann et al. |
| 4,153,063 A | 5/1979 | Roselius et al. |
| 4,830,028 A | 5/1989 | Lawson et al. |
| 4,967,771 A | 11/1990 | Fagg et al. |
| 5,031,646 A | 7/1991 | Lippiello et al. |
| 7,008,742 B2 | 3/2006 | Molaire |
| 7,452,555 B2 | 11/2008 | Childs |
| 7,650,891 B1 | 1/2010 | Groves et al. |
| 7,927,613 B2 | 4/2011 | Almarsson et al. |
| 7,935,817 B2 | 5/2011 | Blazecka et al. |
| 8,058,437 B2 | 11/2011 | Bauer et al. |
| 8,163,790 B2 | 4/2012 | Childs |
| 8,173,625 B2 | 5/2012 | Brittain et al. |
| 8,197,592 B2 | 6/2012 | Thompson et al. |
| 8,212,079 B2 | 7/2012 | Childs |
| 8,241,371 B2 | 8/2012 | Hanna et al. |
| 8,350,085 B2 | 1/2013 | Childs |
| 8,415,507 B2 | 4/2013 | Schultheiss et al. |
| 8,466,280 B2 | 6/2013 | Grunenberg et al. |
| 8,470,832 B2 | 6/2013 | George et al. |
| 8,513,236 B2 | 8/2013 | Schultheiss et al. |
| 8,999,405 B1 | 4/2015 | Bachman |
| 9,724,341 B2 | 8/2017 | Myers et al. |
| 2002/0048610 A1 | 4/2002 | Cima et al. |
| 2003/0224006 A1 | 12/2003 | Zaworotko et al. |
| 2006/0018840 A1 | 1/2006 | Lechuga-Ballesteros et al. |
| 2007/0287194 A1 | 12/2007 | Childs et al. |
| 2008/0280858 A1 | 11/2008 | Hanna et al. |
| 2008/0302377 A1 | 12/2008 | Nauryzbaev et al. |
| 2010/0204204 A1 | 8/2010 | Zaworotko et al. |
| 2011/0152266 A1 | 6/2011 | Grunenberg et al. |
| 2011/0174323 A1 | 7/2011 | Coleman, III et al. |
| 2011/0236478 A1 | 9/2011 | Dokou et al. |
| 2011/0251426 A1 | 10/2011 | Childs et al. |

(Continued)

FOREIGN PATENT DOCUMENTS

| | | |
|---|---|---|
| WO | WO 03/101454 | 12/2003 |
| WO | WO 2006/004646 | 1/2006 |

(Continued)

OTHER PUBLICATIONS

Halebian et al., Pharmaceutical Applications, etc., Pharmaceutical Sciences 58(8), 1969, 911-929.*

(Continued)

*Primary Examiner* — Patricia L Morris

(74) *Attorney, Agent, or Firm* — Womble Bond Dickinson (US) LLP

(57) ABSTRACT

The invention provides certain nicotine salt co-crystals and provides novel polymorphic forms of certain nicotine salts. In particular, certain nicotine salt-co-crystals are described, including nicotine and two different coformers. The invention further provides methods of preparation and characterization of nicotine salts, co-crystals, and salt co-crystals. In addition, tobacco products, including smoking articles, smokeless tobacco products, and electronic smoking articles comprising nicotine salts, co-crystals, and/or salt co-crystals are also provided.

15 Claims, 21 Drawing Sheets

(56) References Cited

U.S. PATENT DOCUMENTS

| | | |
|---|---|---|
| 2011/0257430 A1 | 10/2011 | Childs |
| 2011/0259353 A1 | 10/2011 | Coleman, III et al. |
| 2011/0268809 A1 | 11/2011 | Brinkley et al. |
| 2012/0022117 A1 | 1/2012 | Gruss et al. |
| 2012/0028930 A1 | 2/2012 | Kalofonos et al. |
| 2012/0028998 A1 | 2/2012 | Sansone et al. |
| 2012/0192880 A1 | 8/2012 | Dube et al. |
| 2012/0192882 A1 | 8/2012 | Dube et al. |
| 2012/0211016 A1 | 8/2012 | Byrd, Jr. et al. |
| 2012/0258170 A1 | 10/2012 | Kruthiventi et al. |
| 2013/0040970 A1 | 2/2013 | Cosgrove et al. |
| 2013/0072440 A1 | 3/2013 | Dokou et al. |
| 2013/0078307 A1 | 3/2013 | Holton, Jr. et al. |
| 2013/0203806 A1 | 8/2013 | Chorlton et al. |
| 2013/0274296 A1 | 10/2013 | Jackson et al. |
| 2014/0000638 A1 | 1/2014 | Sebastian et al. |
| 2014/0088044 A1 | 3/2014 | Rigas et al. |
| 2016/0185750 A1 | 6/2016 | Dull et al. |
| 2018/0051002 A1 | 2/2018 | Dull et al. |

FOREIGN PATENT DOCUMENTS

| | | |
|---|---|---|
| WO | WO 2006/053082 | 5/2006 |
| WO | WO 2010/044736 | 4/2010 |
| WO | WO 2011/017533 | 2/2011 |
| WO | WO 2013/158643 | 10/2013 |
| WO | WO 2014/006604 | 9/2014 |
| WO | WO 2014/182736 | 11/2014 |
| WO | WO 2015/166350 | 11/2015 |
| WO | WO 2015/183801 | 12/2015 |
| WO | WO 2016/071705 | 5/2016 |
| WO | WO 2016/071706 | 5/2016 |
| WO | WO 2017/051181 | 3/2017 |
| WO | WO 2017/055866 | 4/2017 |
| WO | WO 2017/089931 | 6/2017 |

OTHER PUBLICATIONS

Dean "Analytical Chem . . . " p. 10.24-10.26 (1995).*
Seddon "Pseudopolymorph . . . " Crystal Growth & design v.4(6) p. 1087 (2004) (2 pages from internet).*
Ivanisevic et al., "Use of X-ray . . . "Pharm. Sci. Encycl. p. 1-42 (2010).*
Ivanisevic et al., "Uses of X-ray, etc.," Pharm. Form. Qual. 2011, pp. 30-33.*
Bhattacharya et al., "Thermoanalytical and Crystallographic Methods" in Brittain H. ed., 2nd ed. Informa Healthcare:NY 2009 p. 318-335.*
Aakeroy, "Crystal Engineering, etc.," Acta Cryst. (1997) B53, 569-586.*
Sekhon BS, "Pharmaceutical co-cyrstals, etc." Ars Pharm., 50(2): 99-117 (2009).*
Kirk-Othmer Encyclopedia of Chemical Technology, 8, pp. 95-147 (2002).*
Stahly, "Diversity in Single-, etc.", Crystal Growth & Design, 7 (6), 2007, 1007-1026.*
Vippagunta et al., "Crystalline Solids", Advanced Drug Delivery Reviews 48 (2001) 3-26.*
Braga et al., "Making crystals from . . . " J. Royal Soc. Chem. Commun. p. 3635-3645 (2005).*
Davidovich et al., "Detection of polymorphism . . . " Am. Pharm. Rev. v.&(1) p. 10, 12, 14, 16, 100 (2004).*
Weyna et al., "Synthesis and Structural, etc.," Crystal Growth & Design, 2009, 9(2), 1106-1123.*
Bernstein, "Polymorphism kn . . . " 115-118, 272. (Year: 2002).*
www.jce.divched.org "Nicotine Volatilization in Tobacco Matrix," *Journal of Chemical Education*, 2005, vol. 82, No. 10, pp. 1577-1578.
http://www.fda.gov/Drugs/GuidanceComplianceRegulatoryInformation/Guidance/default.htm; "Guidance for Industry, Regulatory Classification of Pharmaceutical Co-Crystals," U.S. Department of Health and Human Services, Food and Drug Administration, Center for Drug Evaluation and Research, (CDER), Apr. 2013, pp. 1-5.
Challener, "API Synthesis & Manufacturing: Scientific Advances in Cocrystals are Offset by Regulatory Uncertainty," *Pharmaceutical Technology*, May 2014, pp. 42-45. www.PharmTech.com.
Dezelic et al. "Nicotine Compounds with Aromatic Acids," *Kem. Vjestnik*, 17, 1943, 39-57.
Dezelic et al., "Nicotine Compounds with Aromatic Acids. Part II," *Glasnik Drustva Hemicara Technol. NR Bosne Hercegovine*, 1961, vol. 10, pp. 55-62.
Dezelic et al., "Determination of the Composition and the Molecualar Weights of Some Salts of Heterocyclic Bases from the UV Spectra" *Glasnik Hemicara i Tehnologa BiH, Sarajevo*, 1964-1965, 13-14, 27-36.
Dezelic et al., "Determination of Structure of Some Salts of Nicotine, pyridine and N-Methylpyrrolidine on the Basis of Their Infra-Red Spectra," *Spectrochimica Acta, Part A: Molecular and Biomolecular Spectroscopy* (1967), 23(A), 1149-53.
Kim et al., "The Crystal Structure of a 1:1 Nicotine-Salicylic Acid Complex (Nicotinyl Salicylate)," *Acta Cryst.*, 1971, B27, pp. 1123-1131.
Lasslo et al., "Salts of p-Acetamidobenzoic Acid," *J. Amer. Pharm. Assoc.* (1912-1977), 1959, 48, 345-7.
Nikolin et al., "Structure of Some Nicotine Salts and Their Fungicidal Action," *Glasnik Hemicara i Tehnologa BiH, Sarajevo*, 18, (1970) pp. 17-24.
Perfetti, "Structural Study of Nicotine Salts," *Beitrage Tabakforschung Int.*, vol. 12, No. 2, 43-54 (1983).
Perfetti, "The Transfer of Nicotine from Nicotine Salts to Mainstream Smoke," *Beitrage Tabakforschung Int., Contributions to Tobacco Research*, vol. 19, No. 3, 2000, pp. 141-158.
Seeman et al., "The Form of Nicotine in Tobacco. Thermal Transfer of Nicotine and Nicotine Acid Salts to Nicotine in the Gas Phase," *J. Agric. Food Chem.* 1999, vol. 47, pp. 5133-5145.

\* cited by examiner

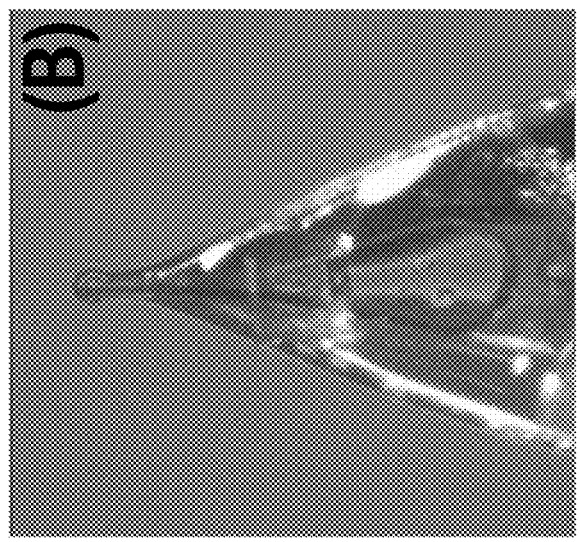
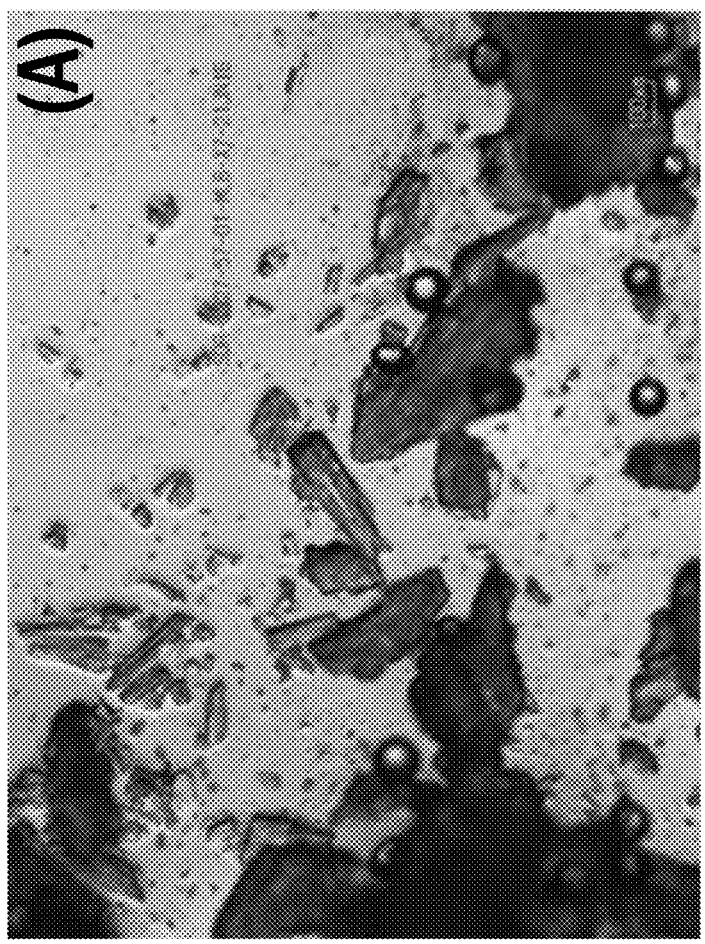
FIG. 1A
FIG. 1B

FIG. 17
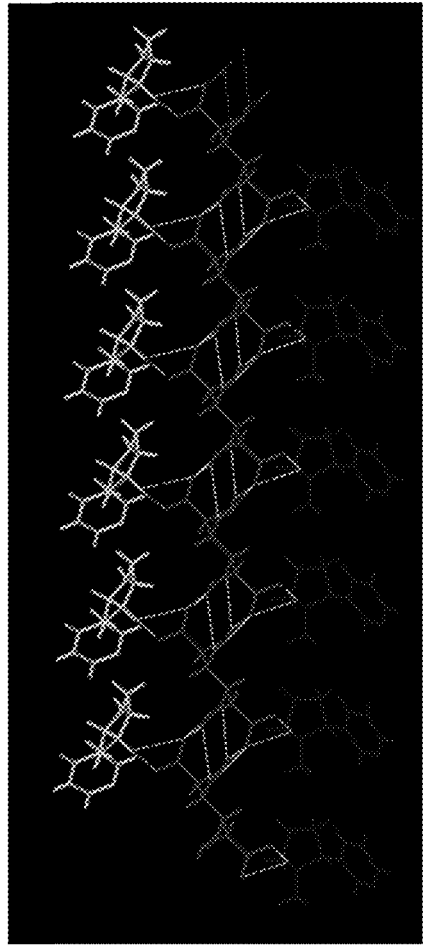
nicotinium
mucate
nicotinium
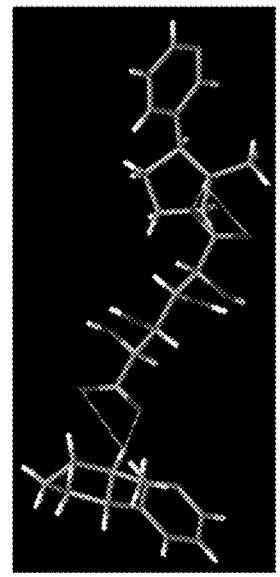
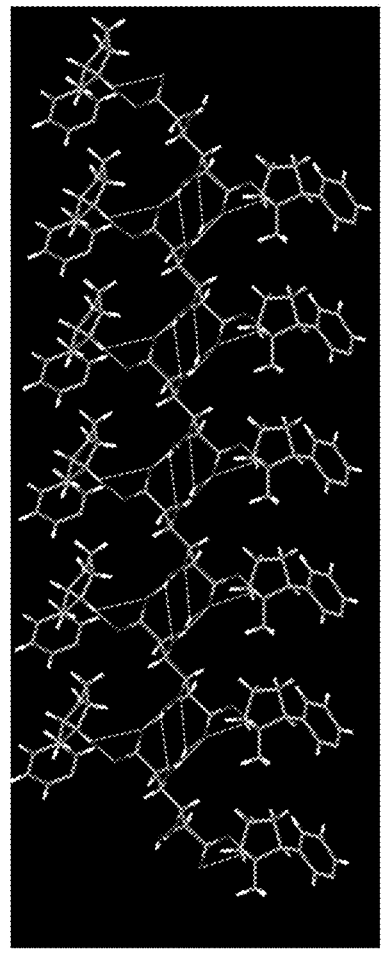

NICOTINE SALTS, CO-CRYSTALS, AND SALT CO-CRYSTAL COMPLEXES

CROSS-REFERENCE TO RELATED APPLICATIONS

The present application is a continuation-in-part of U.S. patent application Ser. No. 15/671,722, filed Aug. 8, 2017, which is a continuation of U.S. Patent Application No. 14/721,283, filed May 26, 2015, now issued as U.S. Pat. No. 9,738,622, which claims priority to U.S. Provisional Patent Application No. 62/003,295, filed May 27, 2014. All of these applications are incorporated by reference herein in their entireties.

FIELD OF THE INVENTION

The present invention relates to various salts, co-crystals, and salt co-crystals of nicotine and to compositions and products (e.g., tobacco products) into which such salts, co-crystals, and salt co-crystals can be incorporated.

BACKGROUND OF THE INVENTION

Cigarettes, cigars and pipes are popular smoking articles that employ tobacco in various forms. Such smoking articles are used by heating or burning tobacco, and aerosol (e.g., smoke) is inhaled by the smoker. Electronic smoking articles are a further type of tobacco product, which comprise a reservoir and heating system for the delivery of aerosolizable materials. Tobacco also may be enjoyed in a so-called "smokeless" form. Particularly popular smokeless tobacco products are employed by inserting some form of processed tobacco or tobacco-containing formulation into the mouth of the user.

Various types of cigarette components, including tobacco types, tobacco blends, top dressing and casing materials, blend packing densities and types of paper wrapping materials for tobacco rods, are set forth in the art. See, for example, the various representative types of cigarette components, as well as the various cigarette designs, formats, configurations and characteristics, that are set forth in Johnson, Development of Cigarette Components to Meet Industry Needs, $52^{nd}$ T.S.R.C. (September 1998); U.S. Pat. No. 5,101,839 to Jakob et al.; U.S. Pat. No. 5,159,944 to Arzonico et al.; U.S. Pat. No. 5,220,930 to Gentry and U.S. Pat. No. 6,779,530 to Kraker; US Pat. App. Pub. Nos. 2005/0016556 to Ashcraft et al.; 2005/0066986 to Nestor et al.; 2005/0076929 to Fitzgerald et al.; 2006/0272655 to Thomas et al.; 2007/0056600 to Coleman, III et al.; and 2007/0246055 to Oglesby, each of which is incorporated herein by reference.

Exemplary smokeless tobacco formulations, ingredients, and processing methodologies are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0196730 to Engstrom et al.; 2008/0209586 to Neilsen et al.; 2008/0305216 to Crawford et al.; 2009/0065013 to Essen et al.; 2009/0293889 to Kumar et al.; 2010/0291245 to Gao et al. and 2011/0139164 to Mua et al.; PCT WO 04/095959 to Arnarp et al. and WO 2010/132444 A2 to Atchley; each of which is incorporated herein by reference. Exemplary smokeless tobacco products that have been marketed include those referred to as CAMEL Snus, CAMEL Orbs, CAMEL Strips and CAMEL Sticks by R. J. Reynolds Tobacco Company; GRIZZLY moist tobacco, KODIAK moist tobacco, LEVI GARRETT loose tobacco and TAYLOR'S PRIDE loose tobacco by American Snuff Company, LLC; KAYAK moist snuff and CHATTANOOGA CHEW chewing tobacco by Swisher International, Inc.; REDMAN chewing tobacco by Pinkerton Tobacco Co. LP; COPENHAGEN moist tobacco, COPENHAGEN Pouches, SKOAL Bandits, SKOAL Pouches, RED SEAL long cut and REVEL Mint Tobacco Packs by U.S. Smokeless Tobacco Company; and MARLBORO Snus and Taboka by Philip Morris USA.

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. Pub. No. 2013/0255702 to Griffith Jr. et al., U.S. Pat. Pub. Nos. 2014/0000638 to Sebastian et al., 2014/0060554 to Collett et al., 2014/0060555 to Chang et al., 2014/0096781 to Sears et al., 2014/0096782 to Ampolini et al., and 2015/0059780 to Davis et al., which are incorporated herein by reference in their entireties.

Certain of these types of smoking articles, smokeless tobacco products, and electronic smoking articles comprise a tobacco extract, which in some products may be purified such that the extract is comprised primarily of nicotine. However, tobacco extracts comprising a high percentage of nicotine (including extracts comprising at least about 90%, at least about 95%, and at least about 99% nicotine by weight) are typically in oil form. As such, nicotine extracts can be difficult to handle and incorporate into certain tobacco products.

It would be desirable to provide such nicotine-based extracts in a form that is amenable to incorporation in tobacco products. It would further be desirable to incorporate such extracts into an enjoyable form of a tobacco product and to provide processes for preparing such forms of nicotine-based extracts as well as for preparing various types of compositions and products incorporating such forms of nicotine-based extracts.

SUMMARY OF THE INVENTION

The present invention provides various forms of nicotine that can be applicable to a wide range of products, including tobacco products. Particularly, the present application describes nicotine salts, co-crystals, and salt co-crystals and the preparation of such nicotine salts, co-crystals, and salt co-crystals. It also describes the incorporation of such nicotine salts, co-crystals, and/or salt co-crystals into various products including tobacco products (e.g., smoking articles, smokeless tobacco products, and electronic smoking articles) and pharmaceutical products.

In a first aspect of the invention is provided nicotine salt-co-crystals. In particular, the disclosure describes nicotine L-malate-(L-malic acid-succinic acid), nicotine fumarate nicotinamide, and nicotine monoorotate succinic acid. Advantageously, in some embodiments, a given percentage of these nicotine salt-co-crystals is in crystalline form. For example, in various embodiments at least about 50% of the nicotine salt-co-crystal is in crystalline form. In other embodiments, at least about 80% or at least about 90% of the nicotine salt-co-crystal is in crystalline form.

The nicotine salt-co-crystals can, in some embodiments, be characterized as having particular peaks in X-ray powder diffraction patterns obtained therefrom. For example, nicotine L-malate-(L-malic acid-succinic acid) can be characterized by an X-ray powder diffraction pattern having peaks at one or more of the following 2-theta diffraction angles: 17.1, 18.7, 20.0, 21.6, 25.1, and 25.4. Nicotine fumarate nicotinamide can be characterized by an X-ray powder diffraction pattern having peaks at one or more of the following 2-theta diffraction angles: 5.8, 14.5, 18.2, 19.2, 23.3, 25.5, and 28.5.

The invention also provides new nicotine mucate salt forms and products incorporating such salt forms. For example, a nicotine mucate salt form is provided which is characterized by an X-ray powder diffraction pattern having peaks at one or more of the following 2-theta diffraction angles: 10.2, 15.5, 16.1, 17.1, 19.4, 21.7, and 26.7.

The nicotine salts and salt co-crystals described in the present application are generally applicable for use in a range of products including, but not limited to, smoking articles, electronic smoking articles, smokeless tobacco products (e.g., lozenges and gums), pharmaceutical products, and the like. Accordingly, in another aspect of the invention is provided a product incorporating one or more nicotine salts and/or salt co-crystals as described herein. In various embodiments, electronic smoking articles, smokeless tobacco products, and/or pharmaceutical products incorporating one or more of the salts and/or salt co-crystal complexes disclosed herein are provided.

For example, in one aspect, the disclosure provides an electronic smoking article comprising an inhalable substance medium contained within a cartridge body and a heating member positioned to provide heat to at least a portion of the inhalable substance medium, wherein the inhalable substance medium comprises: the disclosed form of nicotine mucate or a salt-co-crystal selected from nicotine L-malate-(L-malic acid-succinic acid), nicotine fumarate nicotinamide, and nicotine monoorotate succinic acid. The inhalable substance medium can further comprise, for example, one or more of glycerin, water, and a flavorant. The amount of salt or salt-co-crystal incorporated can vary and, in some embodiments, can be that amount sufficient to provide nicotine in an amount of about 0.01 mg to about 0.5 mg, about 0.05 mg to about 0.3 mg, or about 0.1 mg to about 0.2 mg per puff on the article.

In another aspect, the disclosure provides a smokeless tobacco product comprising the disclosed form of nicotine mucate or a salt-co-crystal selected from nicotine L-malate-(L-malic acid-succinic acid), nicotine fumarate nicotinamide, and nicotine monoorotate succinic acid. Exemplary smokeless tobacco products include, but are not limited to, loose moist snuff (e.g., snus); loose dry snuff; chewing tobacco; pelletized tobacco pieces; extruded or formed tobacco strips, pieces, rods, cylinders or sticks; finely divided ground powders; finely divided or milled agglomerates of powdered pieces and components; flake-like pieces; molded tobacco pieces; gums; rolls of tape-like films; readily water-dissolvable or water-dispersible films or strips; meltable compositions; lozenges; pastilles; and capsule-like materials possessing an outer shell and an inner region.

In a further aspect, the disclosure provides a pharmaceutical product comprising a nicotine salt or salt co-crystal as described herein (e.g., the disclosed form of nicotine mucate or a salt co-crystal selected from nicotine L-malate-(L-malic acid-succinic acid), nicotine fumarate nicotinamide, and nicotine monoorotate succinic acid). Such products can be, for example, in a form selected from the group consisting of a pill, tablet, lozenge, capsule, caplet, pouch, gum, inhaler, solution, and cream. One exemplary lozenge formulation comprises one or more of the nicotine salts or crystalline polymorphic forms disclosed herein and at least about 50% by weight isomalt.

Additionally, in a still further aspect, the disclosure provides methods of preparing certain nicotine salts, salt co-crystals, and crystalline polymorphic forms. For example, the disclosure provides methods of preparing a novel nicotine mucate salt form. The disclosure also provides method of preparing nicotine salt co-crystals, e.g., comprising combining a nicotine salt and a coformer and isolating the as-produced solid. In certain embodiments, the combining comprises grinding the nicotine salt and coformer or comprises mixing the nicotine salt and coformer in neat nicotine or in a solvent, e.g., including, but not limited to, acetone or THF.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

FIGS. 1A and 1B are optical micrographs of a batch of nicotine L-malate-(L-malic acid-succinic acid) salt co-crystals at varying magnifications;

FIG. 1B is an optical micrograph of a single crystal of a nicotine L-malate-(L-malic acid-succinic acid) salt co-crystal used for single crystal x-ray diffraction data collection;

FIG. 17 is a single crystal x-ray structure of the previously reported mucate salt;

DETAILED DESCRIPTION OF THE PREFERRED EMBODIMENTS

Figure 2:
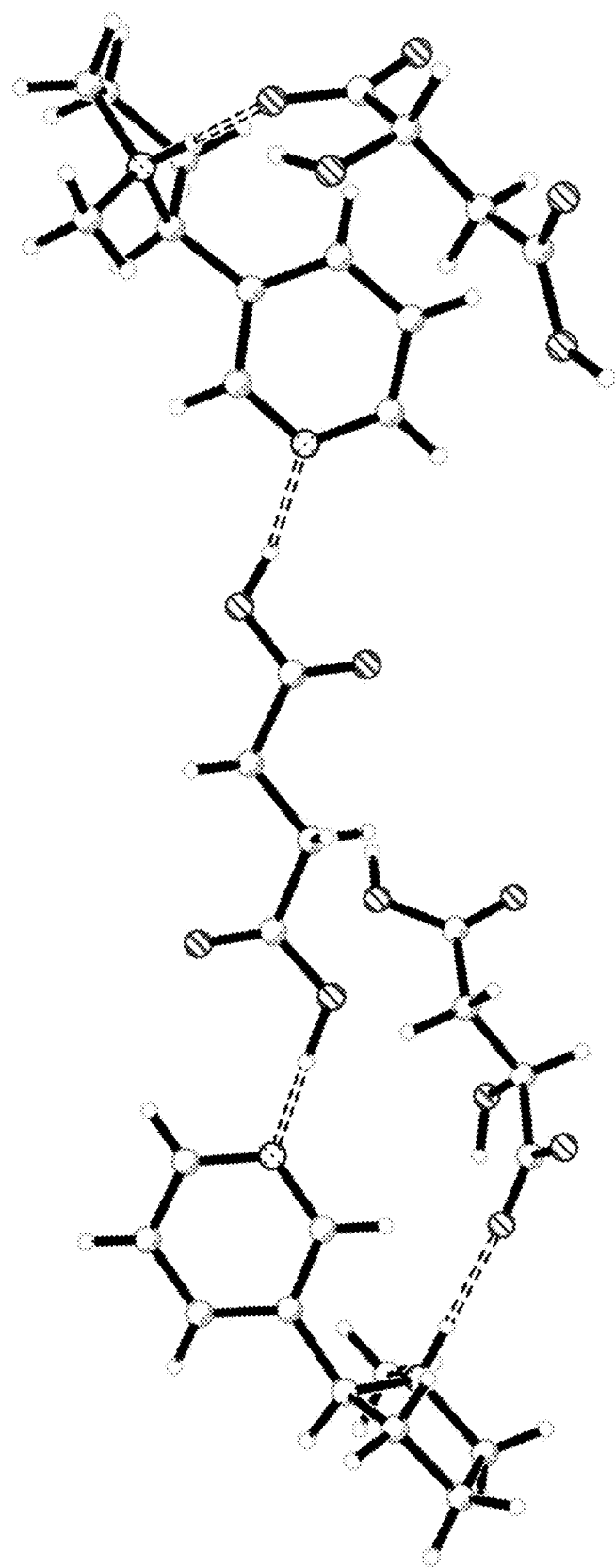
FIG. 2 is a ball and stick diagram of a (S)-nicotine L-malate-(L-malic acid-succinic acid) salt co-crystal with minor components of the disorder omitted for clarity.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The present invention relates to nicotine salts, co-crystals, and salt co-crystals and methods of preparation thereof. It also relates to products (including tobacco products and pharmaceutical products) that comprise one or more nicotine salts, co-crystals, and/or salt co-crystals. In certain embodiments, nicotine provided in one or more such forms can advantageously be isolated in a physical form that is an improvement over neat nicotine, which is a hygroscopic, oily liquid. For example, in certain embodiments, nicotine salts, co-crystals, and/or salt co-crystals as described herein can be in an easier to handle form than neat nicotine (e.g., a solid or semi-solid form), can be provided in a higher purity form than neat nicotine, and/or can exhibit greater thermodynamic, physical, and/or chemical stability (e.g., a higher resistance to oxidation, reduced risk of hydrate formation, and/or a longer shelf life) than neat nicotine. In some embodiments, nicotine salts, co-crystals, and/or salt co-crystals can provide increased stability in the presence of relevant excipients in the product into which the salt, co-crystal, and/or salt co-crystal will be incorporated, as compared to neat nicotine. In some embodiments, nicotine salts, co-crystals, and salt co-crystals can exhibit a significant degree of water-solubility, rendering them applicable for incorporation within a wide range of compositions and products.

Nicotine itself can be isolated and/or treated such that it is in one of two enantiomeric forms or it may be provided in racemic form. Nicotine is naturally occurring in levorotatory, (L)-nicotine form (also known as (–)-nicotine or S-nicotine). In the salts, co-crystals, and salt co-crystals provided herein, the nicotine is generally in the form of (L)-nicotine, although this disclosure is not intended to preclude the preparation and application of dextrorotatory ((D)-nicotine) salts, co-crystals, and salt co-crystals or racemic forms of nicotine in the disclosed salts, co-crystals, and salt co-crystals. Accordingly, nicotine salts, co-crystals, and salt co-crystals can be in an enantiomerically highly pure form (i.e., (L)- or (D)- form) or in racemic form as described herein.

A "nicotine salt" is a form of nicotine characterized by the interaction between nicotine in ionic form and a coformer in ionic form (e.g., an acid) via the transfer of one or more protons from the coformer donor to the nicotine acceptor. The structure of nicotine is such that it comprises two nitrogen atoms that are capable of accepting protons from a coformer and, accordingly, it can be present in non-protonated, mono-protonated, and/or di-protonated form in a given sample.

Certain nicotine salts are presently known. For example, nicotine sulfate has been sold as a pesticide and nicotine bitartrate dihydrate (also known as nicotine hydrogen tartrate) is a commercially available, water-soluble nicotine salt. Various other salts have been studied, including a nicotine acetic acid salt (which forms a viscous oil) as well as, for example, nicotine citrates and nicotine malates. See, for example, the types of ingredients and techniques set forth in U.S. Pat. No. 2,033,909 to Cox et al. and Perfetti, *Beitrage Tabakforschung Int.,* 12, 43-54 (1983). Additionally, certain salts of nicotine have been available from sources such as Pfaltz and Bauer, Inc. and K&K Laboratories, Division of ICN Biochemicals, Inc. Exemplary known nicotine salts include nicotine salts such as nicotine tartrate and nicotine bitartrate, nicotine chloride (e.g., nicotine hydrochloride and nicotine dihydrochloride), nicotine sulfate, nicotine perchlorate, nicotine ascorbate, nicotine fumarate, nicotine citrate, nicotine malate, nicotine lactate, nicotine aspartate, nicotine salicylate, nicotine tosylate, nicotine succinate, nicotine pyruvate, and nicotine salt hydrates (e.g., nicotine zinc chloride monohydrate). A nicotine salt with levulinic acid is discussed in US Pat. App. Pub. No. 2011/0268809 and Int. App. Pub. No. PCT/US2011/033928, both to Brinkley et al., which are incorporated herein by reference. See also, for example, U.S. Pat. No. 4,830,028 to Lawson et al. and U.S. Pat. No. 5,031,646 to Lippiello et al. and Leonard, Ind. Eng.

Chem. 48: 1331-1341 (1956). However, certain previously disclosed nicotine salts of organic acids are not commonly crystalline and can exhibit a range of stoichiometries, which may make them unsuitable for use in certain applications.

Certain nicotine salts, polymorphic forms, co-crystals, and salt co-crystals have been further disclosed in US Pat. App. Publ. No. 2015/0344456 to Dull et al., to which the present application claims priority and which is incorporated herein by reference in its entirety and in US Pat. App. Publ. No. 2016/0185750 to Dull et al., which is incorporated herein by reference in its entirety.

A "nicotine co-crystal" is a form of nicotine comprising nicotine and at least one other component ("coformer"), both in neutral form. Co-crystals are typically characterized by a crystalline structure, which is generally held together by freely reversible, non-covalent interactions. Co-crystals are typically made up of nicotine and at least one other component in a defined stoichiometric ratio. In some embodiments, co-crystals can encompass hydrates, solvates, and clathrates. Co-crystals can comprise nicotine in combination with an organic and/or an inorganic component. Co-crystals can generally be distinguished from salts by the absence of a proton transfer between the components (i.e., the nicotine and the one or more coformers) in a co-crystal. According to the U.S. Food and Drug Administration's Guidance for Industry (April 2013), a co-crystal is defined as a solid that is a crystalline material composed of two or more molecules in the same crystal lattice, where the components are in a neutral state and interact via nonionic interactions. See U.S. Department of Health and Human Services, Food and Drug Administration, Guidance for Industry: Regulatory Classification of Pharmaceutical Co-Crystals (April 2013), which is incorporated herein by reference.

A "nicotine salt co-crystal" is a type of hybrid structure with both salt and co-crystal characteristics. Typically, a nicotine molecule within a salt co-crystal is associated with at least two coformers (which may be the same or different), wherein one coformer is in ionic form (e.g., an acid) and transfers a proton to the nicotine molecule and wherein a second coformer does not transfer a proton to the nicotine molecule.

The stoichiometry of the salts, co-crystals, and salt co-crystals described herein can vary. For example, in certain embodiments, where two components (i.e., nicotine and one coformer) are present, the nicotine: coformer stoichiometry can range in certain embodiments from about 5:1 to about 1:5 nicotine: coformer. Where more than one coformer is used to form a nicotine salt, co-crystal, or salt co-crystal, the ratios of the coformers with respect to both the nicotine and to one another can also vary. In preferable embodiments, a given sample of the salts, co-crystals, and salt co-crystals provided according to the present disclosure exhibit substantially one single stoichiometry.

The salts, co-crystals, and salt co-crystals described herein can, in some embodiments, exist in various polymorphic and pseudopolymorphic forms. Polymorphism is the ability of a crystalline material to exist in more than one form or crystal structure. Polymorphism can result, e.g., from the existence of different crystal packing structures (packing polymorphism) or from the existence of different conformers of the same molecule (conformational polymorphism). Pseudopolymorphism is the result of hydration or solvation of a material and is also referred to as solvomorphism.

The salts, co-crystals, and salt co-crystals of the present disclosure can incorporate nicotine derived from some form of a plant of the Nicotiana species (e.g., some form of tobacco). The nicotine can be, for example, in the form of a highly purified tobacco extract. Various methods are known for the isolation and purification of nicotine from tobacco (including, but not limited to, extraction from tobacco with water; extraction from tobacco with organic solvents; steam distillation from tobacco; or pyrolytic degradation of tobacco and distillation of nicotine therefrom). For exemplary extraction methods, see for example, U.S. Pat. Nos. 2,822,306 and 4,153,063 to Roselius et al. and US Pat. App. Pub. No. 2008/0302377 to Kauryzbaev et al., which are incorporated herein by reference.

The selection of the plant from the *Nicotiana* species (from which such extracts and other tobacco materials that can be combined with the salts, co-crystals, and/or salt co-crystals described herein are obtained) can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and Rustica tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. *Nicotiana* species can be derived using genetic-modification or crossbreeding techniques (e.g., tobacco plants can be genetically engineered or crossbred to increase or decrease production of or to other change certain components, characteristics or attributes). Additional information on types of *Nicotiana* species suitable for use in the present invention can be found in US Pat. App. Pub. No. 2012/0192880 to Dube et al., which is incorporated by reference herein. Tobacco plants can be grown in greenhouses, growth chambers, or outdoors in fields, or grown hydroponically.

The portion or portions of the plant of the *Nicotiana* species used according to the present invention can vary. For example, virtually all of the plant (e.g., the whole plant) can be harvested, and employed as such. Alternatively, various parts or pieces of the plant can be harvested or separated for further use after harvest. For example, the leaves, stem, stalk, roots, lamina, flowers, seed, and various portions and combinations thereof, can be isolated for further use or treatment. The plant material of the invention may thus comprise an entire plant or any portion of a plant of the *Nicotiana* species. See, for example, the portions of tobacco plants set forth in US Pat. App. Pub. Nos. 2011/0174323 to Coleman, III et al. and 2012/0192880 to Dube et al., which are incorporated by reference herein.

The plant of the *Nicotiana* species can be employed in either an immature or mature form, and can be used in either a green form or a cured form, as described in 2012/0192880 to Dube et al., which is incorporated by reference herein. The tobacco material can be subjected to various treatment processes such as, refrigeration, freezing, drying (e.g., freeze-drying or spray-drying), irradiation, yellowing, heating, cooking (e.g., roasting, frying or boiling), fermentation, bleaching or otherwise subjected to storage or treatment for later use. Exemplary processing techniques are described, for example, in US Pat. App. Pub. Nos. 2009/0025739 to Brinkley et al. and 2011/0174323 to Coleman, III et al., which are incorporated by reference herein. At least a portion of the plant of the Nicotiana species can be treated with enzymes and/or probiotics before or after harvest, as discussed in US Pat. App. Pub. Nos. 2013/0269719 to Marshall et al. and 2014/0020694 to Moldoveanu, which are incorporated herein by reference.

A harvested portion or portions of the plant of the *Nicotiana* species can be physically processed. A portion or portions of the plant can be separated into individual parts or pieces (e.g., roots can be removed from stalks, stems can be removed from stalks, leaves can be removed from stalks and/or stems, petals can be removed from the remaining portion of the flower). The harvested portion or portions of the plant can be further subdivided into parts or pieces (e.g., shredded, cut, comminuted, pulverized, milled or ground into pieces or parts that can be characterized as filler-type pieces, granules, particulates or fine powders). The harvested portion or portions of the plant can be subjected to external forces or pressure (e.g., by being pressed or subjected to roll treatment). When carrying out such processing conditions, the harvested portion or portions of the plant can have a moisture content that approximates its natural moisture content (e.g., its moisture content immediately upon harvest), a moisture content achieved by adding moisture to the harvested portion or portions of the plant, or a moisture content that results from the drying of the harvested portion or portions of the plant. As such, harvested portion or portions of the plant can be used as such as components of tobacco products, or processed further.

To provide a nicotine extract, the plant of the *Nicotiana* species or portions thereof is typically subjected to one or more types of processing conditions. Typical separation processes can include one or more process steps (e.g., solvent extraction using polar solvents, organic solvents, and/or supercritical fluids), chromatography, distillation, filtration, recrystallization, and/or solvent-solvent partitioning. Exemplary extraction and separation solvents or carriers include water, alcohols (e.g., methanol or ethanol), hydrocarbons (e.g., heptane and hexane), halogenated hydrocarbons (e.g., monofluorotrichloromethane (Freon 11), dichlorotrifluoroethane (Freon 123), and the like), diethyl ether, methylene chloride, and supercritical carbon dioxide. See, for example, the description of isolated tobacco components and techniques for isolation in U.S. Pat. No. 4,967,771 to Fagg et al., US Pat. App. Pub. Nos. 2011/0174323 to Coleman, III et al.; 2011/0259353 to Coleman, III et al.; 2012/0192880 to Dube et al.; 2012/0192882 to Dube et al.; and 2012/0211016 to Byrd, Jr. et al., which are incorporated by reference herein.

Although the nicotine incorporated within the salts, co-crystals, and salt co-crystals of the present disclosure are commonly derived from some form of a plant of the Nicotiana species as outlined above, the source of the nicotine is not limited thereto. For example, in some embodiments, nicotine may be provided synthetically. In some embodiments, nicotine may be obtained from another source (e.g., another type of plant).

Nicotine is typically isolated (e.g., as described above) or prepared in neat (liquid) form. According to the present invention, nicotine is modified such that it is provided in other forms by incorporating the nicotine as a component of a salt, co-crystal, or salt co-crystal, e.g., in the form of an oil, solid, semi-solid, etc. In some embodiments, certain salts, co-crystals, and salt co-crystals are desirably provided in solid form, e.g., solid, crystalline form. Advantageously (although not necessarily), coformers (including acids) that are combined with nicotine to form such nicotine salts, co-crystals, or salt co-crystals are "GRAS" (Generally Regarded As Safe) according to the U.S. Food and Drug Administration. Furthermore, it is beneficial (although again, not necessary) for the nicotine salts, co-crystals, and/or salt co-crystals produced thereby to also be GRAS.

In one embodiment, a salt of nicotine and mucic acid is provided with 0.6 equivalents of mucic acid to 1.0 equivalent of nicotine. A salt of nicotine and mucic acid has been described with 0.7 equivalents of mucic acid (see US Pat. App. Publ. No. 2015/0344456 to Dull et al.). The presently disclosed salt form can be prepared, e.g., from ethanol and, in some embodiments is provided as a white crystalline powder. In some embodiments, the salt with 0.6 equivalents of mucic acid has a melting point around 125° C. and exhibits no significant weight loss below 100° C. in thermogravimetric analysis (TGA) studies. Further detail is provided in Example 5.

In another embodiment, a salt co-crystal of nicotine, L-malic acid, and succinic acid is provided, i.e., referred to herein as nicotine L-malate (L-malic acid-succinic acid). In certain embodiments, the salt co-crystal has about 1.2-1.6 equivalents malic acid and 0.4 to 0.6 equivalents succinic acid (e.g., about 1.3 equivalents malic acid and about 0.5 equivalents succinic acid or about 1.5 equivalents malic acid and about 0.5 equivalents succinic acid). The stoichiometry of this salt co-crystal can be described as being about 2:0.1:0.9 nicotine L-malate:L-malic acid:succinic acid (as determined, e.g., by $^1$H NMR and/or by SCXRD and/or by elemental analysis). The nicotine L-malate-(L-malic acid-succinic acid) salt co-crystal, as demonstrated herein, has been reproducibly prepared on a scale of up to 10 grams. The material is anhydrous, highly hygroscopic and melts at around 107° C. In some embodiments, this salt co-crystal can be prepared using 1 equivalent of each of nicotine L-malate and succinic acid, e.g., by formation in a solvent such as acetone. Further detail is provided in Example 2.

In a further embodiment, a nicotine monoorotate succinic acid salt co-crystal was obtained at small scale by a grinding preparation technique. The material was obtained as a mixture with the starting materials, but was characterized as being in salt co-crystal form. Attempts to scale up the preparation method were unsuccessful. Further detail is provided in Example 3.

In another embodiment, a salt co-crystal of nicotine, fumaric acid, and nicotinamide is provided, i.e., a nicotine monofumarate nicotinamide salt co-crystal. In certain embodiments, the stoichiometry of this salt co-crystal is about 1.3 equivalents of fumaric acid and 1.3 equivalents of nicotinamide. This material is crystalline and highly hygroscopic. This salt co-crystal can, in some embodiments, be prepared by reaction in nitromethane or acetone or by a grinding technique. Experiments using a range of techniques and solvents were carried out, highlighting that preparation procedures were not reproducible. Moreover, a number of other crystalline solids were obtained throughout, including suspected fumaric acid: nicotinamide co-crystals. The nicotine monofumarate nicotinamide salt co-crystal is crystalline, highly hygroscopic and deliquesces at elevated temperature/humidity and after the GVS experiment. Thermal analysis showed two broad endotherms at low temperatures, with decomposition above 125° C., highlighting its low thermal stability. Further detail is provided in Example 4.

One skilled in the art will understand that all diffraction pattern data provided herein should not be construed as absolute and, accordingly, the nicotine salts and salt co-crystals of the invention are not limited to particles having XRPD patterns identical to those in the referenced figures. Any nicotine salts, co-crystals, or salt co-crystals having XRPD patterns substantially the same as those of the relevant figures will be considered to fall within the scope of the invention. A person skilled in the art of X-ray powder diffraction is able to judge the substantial identity of X-ray powder diffraction patterns. Generally, a measurement error of a diffraction angle in an X-ray powder diffractogram is about 2-theta=0.5° or less (more suitably, about 2-theta=0.2° or less) and such degree of a measurement error should be taken into account when considering the X-ray powder diffraction pattern in the figures provided herewith and/or the peak values provided herein. In other words, the peaks in the figures and the peak values given throughout the specification can be viewed, in certain embodiments, as being +/−0.5° or +/−0.2°. See Fundamentals of Powder Diffraction and Structural Characterization, Pecharsky and Zavalij, Kluwer Academic Publishers, 2003.

Other nicotine salts, co-crystals, and salt co-crystals are also encompassed by the present disclosure. For a list of pharmaceutically acceptable counter-ions, see Handbook of Pharmaceutical Salts—Properties, Selection, and Use, P. Heinrich Stahl, Camille G. Wermuth (Eds.) VHCA (Verlag Helvetica Chemica Acta -Zürich), Wiley-VCH (New York) 2002, which is incorporated herein by reference. For example, certain coformers useful for reaction with the nicotine, which may result in the formation of a salt, co-crystal, or salt co-crystal include, but are not limited to: acetic acid; adipic acid; ascorbic acid; capric (decanoic) acid; citric acid; D-glucuronic acid; D-gluconic acid; DL-lactic acid; L-lactic acid; galactaric (mucic) acid; hippuric (N-benzoylglycine) acid; hydrochloric acid; L-aspartic acid; L-glutamic acid; L-glutaric acid; glycerophosphoric acid; glycolic acid; lauric acid; DL-malic acid; L-malic acid; DL-tartaric acid; L-tartaric acid; palmitic acid; phosphoric acid; sebacic (1,8-octanedicarboxylic) acid; stearic (octadecanoic) acid; succinic acid; sulfuric acid; and thiocyanic acid (HS—CN). Other exemplary coformers for reaction with the nicotine, which may result in the formation of a salt, co-crystal, or salt co-crystal include, but are not limited to, (+)-camphoric acid; 1,5-naphthalenedisulfonic acid; 1-hydroxy-2-naphthoic (xinafoic) acid; 2,5-dihydroxybenzoic (gentisic) acid; benzenesulfonic acid; benzoic acid; caprylic (octanoic) acid; cyclamic acid; ethanesulfonic acid; fumaric acid; D-glucoheptonic acid; 4-hydroxybenzoic acid; isobutyric acid; ketoglutaric (2-oxo-glutaric) acid; 2-ketobutyric acid; lactobionic acid; maleic acid; malonic acid; methanesulfonic acid; naphthalene-2-sulfonic acid; nicotinic acid; oleic (Z-octadecenoic) acid; orotic acid; oxalic acid; pamoic acid; pivalic acid; propionic acid; L-pyroglutamic acid; and p-toluenesulfonic acid.

Certain other types of coformers are generally associated with pharmacological effects and are not typically preferred for the preparation of salts, co-crystals, and salt co-crystals. Although complexes of nicotine with such coformers may not be preferred, in certain specialized embodiments, they may be reacted with nicotine to form salts, co-crystals, and/or salt co-crystals. Such coformers include, but are not limited to, (1S)-camphor-10-sulfonic acid; 4-acetamidobenzoic acid; 4-aminosalicylic acid, N-acetyl-4-aminosalicylic acid; caproic (hexanoic) acid; dichloroacetic acid; hydrobromic acid; DL-mandelic acid; L-mandelic acid; nitric acid; formic acid; salicylic acid; cinnamic (e.g., trans-cinnamic) acid; and undecylenic acid. Other exemplary coformers that may form salts, co-crystals, and/or salt co-crystals with nicotine include, but are not limited to, isothionic acid; lauric (dodecanoic) acid; 2-hydroxybenzoic acid; trans-2-hexanoic acid; trimesic acid; and 5-nitroisophthalic acid.

Various other coformers can be used to provide nicotine in the form of a salt, co-crystal, or salt co-crystal. Exemplary co-formers include, but are not limited to, L-proline, tromethamine; urea, xylitol; caffeine; glycine/glycine anhydride; vanillin; methyl 4-hydroxybenzoate (methylparaben); succinamide; L-alanine; mannitol; L-phenylalanine; saccharin; propylparaben; N-methylglucamine; L-tyrosine; gentisic acid; sorbic acid; benzoic acid; L-methionine; maltol; L-lysine, tromethamine; nicotinamide; isonicotinamide; phenylalanine; benzoquinone; terephthalaldehyde; 2,4-dihydroxybenzoic acid; and 4-hydroxybenzoic acid.

Additional coformers include pyruvic acid, 1-hydroxy-2-naphthoic acid, 4-aminobenzoic acid, 3,5-dihydroxybenzoic acid, 2,3-dihydroxybenzoic acid, 3,4-dihydroxybenzoic acid, 2,4-dihydroxybenzoic acid, vanillic acid, ethyl vanillin, isonicotinic acid, gallic acid, menthol (e.g., racemic menthol or (−)-menthol), paracetamol, aspirin, ibuprofen, naproxen, ketoprofen, flurbiprofen, glucose, serine, malic acid, acetamide, sulfacetamide, benzoic acid, 4-aminobenzoic acid, creatine, 2-hydroxyethanesulfonic acid, clofibric acid, taurine (tauric acid), iproniazid, L-histadine, L-arginine, L-asparagine, glutamine, L-cysteine, alanine, valine, isoleucine, leucine, morpholine, threonine, and N-methylglucamine.

Certain exemplary coformers that can provide a nicotine salt, co-crystal, or salt co-crystal are sugar-based acids (i.e., monosaccharides with a carboxyl group). Representative types of sugar acids include aldonic acids (e.g., glyceric acid, xylonic acid, gluconic acid, and ascorbic acid), ulosonic acids (e.g., neuraminic acid and ketodeoxyoctulosonic acid), uronic acids (e.g., glucuronic acid, galacturonic acid, and iduronic acid), and aldaric acids (e.g., tartaric acid, meso-galactaric acid/mucic acid, and D-glucaric acid/saccharic acid). In one preferred embodiment, the coformer or coformers used to provide a nicotine salt, co-crystal, or salt co-crystal according to the present disclosure is an aldaric acid, and in a particular preferred embodiment, the aldaric acid is mucic acid ((2S,3R,4S,5R)-2,3,4,5-tetrahydroxyhexanedioic acid, also referred to as galactaric or meso-galactaric acid).

Other exemplary coformers that can provide a nicotine co-crystal, salt, or salt co-crystal are polyfunctional aromatic acids. Polyfunctional aromatic acids often comprise a substituted or unsubstituted phenyl group as the aromatic component, but can alternatively comprise another aromatic moiety, e.g., pyridine, pyrazine, imidazole, pyrazole, oxazole, thiophene, naphthalene, anthracene, and phenanthrene. Substituents on the optionally substituted aromatic acids may be any type of substituent, including, but not limited to, halo (e.g., Cl, F, Br, and I); alkyl, halogenated alkyl (e.g., $CF_3$, 2-Br-ethyl, $CH_2F$, $CH_2Cl$, $CH_2CF_3$, or $CF_2CF_3$); alkenyl, hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate groups. Exemplary polyfunctional aromatic acids can be, for example:

substituted and unsubstituted aromatic dicarboxylic acids (e.g., 1,2-benzenedicarboxylic acid (phthalic acid), 1,3-benzenedicarboxylic acid (isophthalic acid), 1,4-benzenedicarboxylic acid (terephthalic acid), 2-iodo-1,3-benzenedicarboxylic acid, 2-hydroxy-1,4-benzenedicarboxylic acid, 2-nitro-1,4-benzenedicarboxylic acid, 3-fluoro-1,2-benzenedicarboxylic acid, 3-amino-1,2-benzenedicarboxylic acid, 3-nitro-1,2-benzenedicarboxylic acid, 4-bromo-1,3-benzenedicarboxylic acid, 4-hydroxy-1,3-benzenedicarboxylic acid, 4-amino-1,2-benzenedicarboxylic acid, 4-nitro-1,2-benzenedicarboxylic acid, 4-sulfo-1,2-benzenedicarboxylic acid, 4-amino-1,3-benzenedicarboxylic acid, 5-bromo-1,3- benzenedicarboxylic acid, 5-hydroxy-1,3-benzenedicarboxylic acid, 5-amino-1,3-benzenedicarboxylic acid, 5-nitro-1,3-benzenedicarboxylic acid, 5-ethynyl-1,3-benzenedicarboxylic acid, 5-cyano-1,3-benzenedicarboxylic acid, 5-nitro-1,3-benzenedicarboxylic acid, 2,5-hydroxy-1,4-benzenedicarboxylic acid, and 2,3,5,6-tetrafluoro-1,4-benzenedicarboxylic acid;

substituted and unsubstituted hydroxybenzoic acids (e.g., 2-hydroxybenzoic acid (salicylic acid), 3-hydroxybenzoic acid, 4-hydroxybenzoic acid, 2-methyl-4-hydroxybenzoic acid, 3-tert-butyl-4-hydroxybenzoic acid, 4-ethoxy-2-hydroxybenzoic acid, 3-chloro-5-hydroxybenzoic acid, 5-chloro-2-hydroxybenzoic acid, 3-bromo-4-hydroxybenzoic acid, 3-bromo-5-hydroxybenzoic acid, 4-bromo-2-hydroxybenzoic acid, 5-bromo-2-hydroxybenzoic acid, 2-fluoro-5-hydroxybenzoic acid,3-fluoro-4-hydroxybenzoic acid, 3-fluoro-2-hydroxybenzoic acid, 3-fluoro-5-hydroxybenzoic acid, 2-fluoro-6-hydroxybenzoic acid, 4-fluoro-3-hydroxybenzoic acid, 2-fluoro-4-hydroxybenzoic acid, 5-fluoro-2-hydroxybenzoic acid, 2-amino-3-hydroxybenzoic acid, 2-amino-5-hydroxybenzoic acid, 3-amino-2-hydroxybenzoic acid, 3-amino-4-hydroxybenzoic acid, 3-amino-5-hydroxybenzoic acid, 4-amino-2-hydroxybenzoic acid, 4-amino-3-hydroxybenzoic acid, 5-amino-2-hydroxybenzoic acid (mesalamine), 5-aminomethyl-2-hydroxybenzoic acid, 4-formyl-3-hydroxybenzoic acid, 3-formyl-4-hydroxybenzoic acid, 5-(acetylamino)-2-hydroxybenzoic acid), 4-nitro-2-hydroxybenzoic acid, 3,5-diethyl-4-hydroxybenzoic acid, 3,5-di-tert-butyl-4-hydroxybenzoic acid, 3,5-diisopropyl-2-hydroxybenzoic acid, 3,4-dimethoxy-4-hydroxybenzoic acid (syringic acid), 3,5-dichloro-2-hydroxybenzoic acid, 3,5-dichloro-4-hydroxybenzoic acid, 3,6-dichloro-2-hydroxybenzoic acid, 2,3-difluoro-4-hydroxybenzoic acid, 3,4-difluoro-2-hydroxybenzoic acid, 3,5-dibromo-2-hydroxybenzoic acid, 3,5-diodo-2-hydroxybenzoic acid, 4-amino-5-chloro-2-hydroxybenzoic acid, 3,5-dinitro-2-hydroxybenzoic acid, 2,4,6-tribromo-2-hydroxybenzoic acid, 2,3,5,6-tetrafluoro-4-hydroxybenzoic acid, and 2,3,4,5-tetrafluoro-6-hydroxybenzoicacid);

substituted and unsubstituted dihydroxybenzoic acids (e.g., 2,3-dihydroxybenzoic acid (pyrocatechuic acid/hypogallic acid), 2,4-dihydroxybenzoic acid (β-resorcylic acid), 2,5-dihydroxybenzoic acid (gentisic acid/hydroquinonecarboxylic acid), 2,6-dihydroxybenzoic acid (γ-resorcylic acid), 3,4-dihydroxybenzoic acid (protocatechuic acid), 3,5-dihydroxybenzoic acid (α-resorcylic acid), 4-hydroxy-3-methoxybenzoic acid (vanillic acid), 6-methyl-2,4-dihdroxybenzoic acid (orsellenic acid), 4-bromo-3,5-dihydroxybenzoic acid, 5-bromo-2,4-dihydroxybenzoic acid, 5-bromo-3,4-dihydroxybenzoic acid, 6-carboxymethyl-2,3-dihydroxybenzoic acid, 3,5-dibromo-2,4-dihydroxybenzoic acid, 3,5-dichloro-2,6-dihydroxybenzoic acid, and 5-amino-3-chloro-2,4-dihydroxybenzoic acid); and substituted and unsubstituted trihydroxybenzoic acids (e.g., 2,3,4-trihydroxybenzoic acid, 2,4,5-trihydroxybenzoic acid, 2,4,6-trihydroxybenzoic acid (phloroglucinol carboxylic acid), and 3,4,5-trihydroxybenzoic acid (gallic acid)).

substituted and unsubstituted aromatic tricarboxylic acids (e.g., 1,2,3-benzenetricarboxylic acid, 1,2,4-benzenetricarboxylic acid (trimellitic acid); and substituted and unsubstituted aromatic tetracarboxylic acids (e.g., 1,2,3,4-benzenetetracarboxylic acid (mellophanic acid) and 1,2,4,5-benzenetetracarboxylic acid (pyromellitic acid).

Other coformers useful in certain embodiments are flavor acids, including but not limited to, 3-hydroxy-2-oxopropionic acid; 2-oxobutyric acid (2-ketobutyric acid), 3-methyl-2-oxobutanoic acid; 3-methyl-2-oxopentanoic acid; 4-methyl-2-oxopentanoic acid; and 2-oxopentanedioic acid. Additional coformers can have higher molecular weights, such as 2-oxo-3-phenylpropionic acid; 5-oxooctanoic acid; and 5-oxodecanoic acid.

It is noted that certain coformers as described herein may contain one or more chiral centers, which may be either of the (R) or (S) configuration, or which may comprise a mixture thereof. As a result, various diastereomeric nicotine salts, co-crystals and salt co-crystals may be provided according to the present disclosure. The invention includes such diastereomers, either individually, or admixed in any proportions. Certain coformers as described herein may be geometric isomers, including but not limited to cis and trans isomers across a double bond. The invention includes all nicotine salts, co-crystals, and salt co-crystals prepared with such isomers, which may be provided in the form of pure isomers or in admixture with other isomers.

The method(s) by which the nicotine salts, co-crystals, and salt co-crystals described herein can be produced can vary. In some embodiments, no solvent (or a minimal amount of solvent) is used to prepare the nicotine salts, co-crystals, and salt co-crystals. Although in so-called "solventless" methods, a solvent is commonly not used, it is noted that one or more solvents may optionally be added (typically in a small amount) to the mixture to facilitate the formation of a nicotine salt, co-crystal, or salt co-crystal. In certain embodiments, the components (i.e., the nicotine and the one or more coformers) are combined in the absence of a solvent to form a slurry. Solids comprising nicotine salts, co-crystals, and/or salt co-crystals may be isolated therefrom via common methods (e.g., filtration). The slurry may be optionally heated such that the nicotine and one or more coformers interact in melted form to produce a salt, co-crystal, or salt co-crystal. In certain embodiments, physical methods are used to combine the components (i.e., the nicotine and the one or more coformers). For example, the nicotine and the coformer(s) can be ground together mechanically (e.g., using a mortar and pestle, ball mill, or vibratory mill).

In certain embodiments, a combination of nicotine and a coformer in a given solvent (or solvents) and evaporation of that solvent can provide the desired nicotine salt, co-crystal, or salt co-crystal. Typically, in such methods, the nicotine and coformer are provided in stoichiometric amounts (i.e., no excess nicotine or coformer is added). In such methods, selection of solvent is important, as the solvent (or solvents) in which the reaction is conducted can impact the intermolecular interactions. The evaporation of solvent can be done at a controlled rate (e.g., slowly) to encourage the preparation of a single nicotine salt, co-crystal, or salt co-crystal crystal for characterization. For example, the evaporation of solvent may be effected over the course of hours, days, weeks, or months.

In some embodiments, a combination of nicotine and a coformer in a given solvent (or solvents) and addition of a non-solvent can provide the desired nicotine salt, co-crystal, or salt co-crystal. Exemplary solvents and non-solvents that can be used for the preparation of nicotine salts, co-crystals, and salt co-crystals include, but are not limited to, water, alcohols (e.g., methanol, ethanol, n-butanol, isopropanol), ethers (e.g., diethyl ether, petroleum ether), ethyl acetate (EtOAc), acetone, tetrahydrofuran (THF), methylene chloride (DCM), chloroform, alkanes (e.g., pentane, hexane, heptane, octane, nonane, cyclohexane), benzene, toluene, 1,4-dioxane, nitromethane, and combinations thereof. In some embodiments, nicotine salts, co-crystals, and salt co-crystals can be prepared in supercritical fluids.

In other embodiments, the desired nicotine salt, co-crystal, or salt co-crystal can be prepared by freeze drying and subsequent maturation of a solution of nicotine and one or more coformers. For example, a solution may be prepared, frozen, and lyophilized to remove the solvent. A maturation solvent can then be added and the resulting solids can be obtained by common methods (e.g., filtration). Maturation solvents include, but are not limited, the types of solvents noted above.

The method of production of nicotine salts, co-crystals, and salt co-crystals as described herein may, in some embodiments, employ an excess of the coformer component. In such embodiments, it can advantageously be possible to purify the resulting salt, co-crystal, or salt co-crystal by removing excess coformer therefrom (i.e., that coformer which is not part of the structure of the salt, co-crystal, or salt co-crystal).

Exemplary means for salt, co-crystal, or salt co-crystal formation that may, in certain embodiments, be applicable for the preparation of the nicotine salts, co-crystals, and salt co-crystals described herein are disclosed, for example, in U.S. Pat. No. 8,513,236 to Schultheiss et al.; U.S. Pat. No. 8,470,832 to George et al.; U.S. Pat. No. 8,466,280 to Grunenberg et al.; U.S. Pat. No. 8,415,507 to Schultheiss et al.; U.S. Pat. No. 8,350,085 to Childs; U.S. Pat. No. 8,241,371 to Hanna et al.; U.S. Pat. No. 8,212,079 to Childs; U.S. Pat. No. 8,173,625 to Brittain et al; U.S. Pat. No. 8,163,790 to Childs; U.S. Pat. No. 8,197,592 to Imamura et al.; U.S. Pat. No. 8,058,437 to Bauer et al.; U.S. Pat. No. 7,935,817 to Blazecka et al.; U.S. Pat. No. 7,927,613 to Almarsson et al.; U.S. Pat. No. 7,452,555 to Childs; U.S. Pat. No. 7,008,742 to Molaire; U.S. Pat. App. Pub. Nos. 2013/0203806 to Chorlton et al.; 2013/0072440 to Dokou et al.; 2013/0040970 to Cosgrove et al.; 2012/0258170 to Kruthiventi et al.; 2012/0028998 to Sansone et al.; 2012/0028930 to Kalofonos et al.; 2012/0022117 to Gruss et al.; 2011/0257340 to Childs; 2011/0251426 to Hanna et al.; 2011/0236478 to Dokou et al.; 2011/0152266 to Grunenberg et al.; 2010/0204204 to Zaworotko et al; 2008/0280858 to Hanna et al., 2007/0287194 to Childs et al.; 2003/0224006 to Zaworotko et al.; and 2002/0048610 to Cima et al., which are all incorporated herein by reference in their entireties. Other references that provide exemplary means for the formation of certain nicotine salts include M. Dezelic and B. Nikolin, "Nicotine Compounds with Aromatic Acids. Part II.," Glasnik Drustva Hemicara Technol. N. R. Bosne I Hercegovine, Sarajevo, 10 (1961) 55-62 and M. Dezelic and D. Tomic, "Nicotine Compounds with Aromatic Acids," Kem. Vjestnik 17 (1943):39-57, which are incorporated herein by reference.

For the preparation of the nicotine salts, co-crystals, and salt-co-crystals disclosed herein, the product can, in some embodiments, be provided by combining one or more acids, nicotine, one or more coformers, and/or nicotine salts (depending on the desired product) in the absence of solvent. In some embodiments, an excess of nicotine is added to the reaction mixture and, advantageously, excess nicotine is removed (e.g., by vacuum and/or by washing/filtration, such as with THF, heptane, and/or EtOAc). Although such slurry methods commonly employ no solvent, it is noted that, in some embodiments, some solvent can be added to facilitate the formation of a salt, co-crystal, or salt-co-crystal.

In some embodiments, a solvent is used to facilitate salt formation. For example, an acid can be dissolved in THF, nicotine can be added thereto, and the resulting mixture can be stirred/shaken to produce the salt, co-crystal, or salt-co-crystal. Although a single solvent can, in some embodiments, be sufficient to form the desired salt, co-crystal, or salt-co-crystal, in some embodiments, an anti-solvent is used to promote the formation of a solid material. The solvent can be removed (e.g., by evaporation) to provide the salt, co-crystal, or salt-co-crystal. In some embodiments, the solid is washed, e.g., with THF, heptane, and/or EtOAc. In some embodiments, mechanical grinding is used to promote the formation of the salt, co-crystal, or salt-co-crystal, as will be described further herein (see, e.g., the Examples).

Desirably, single crystal x-ray diffraction (SCXRD) can be used in some embodiments to determine the makeup of the solids (i.e., the nicotine salts, co-crystals, and salt co-crystals). However, suitable, x-ray quality crystals cannot always be readily produced. Therefore, a variety of other solid state spectroscopic techniques can be used including, but not limited to, x-ray powder diffraction (XRPD), Raman spectroscopy, FTIR spectroscopy, vibrational spectroscopy, polarized light microscopy (PLM), and solid state NMR. The nicotine salts, co-crystals, and salt co-crystals described herein may be further characterized, for example, using such techniques as $^{13}C$ NMR and $^{1}H$ NMR (in a suitable solvent, e.g., in $D_2O$ or DMSO-$d_6$) to evaluate the chemical structure, Gravimetric Vapor Sorption (GVS) to evaluate the hygroscopicity, thermogravimetric analysis (TGA) and differential scanning calorimetry (DSC) to evaluate the thermal properties, and/or chromatography (e.g., HPLC) in a suitable solvent to evaluate the purity. Products as described herein can be further analyzed via Karl Fischer Titration (KF) to determine the water content.

It is noted that, in certain cases, it is difficult to distinguish between co-crystals and salts. Typically, distinguishing a salt from a co-crystal requires evidence of proton transfer, which may not be straightforward to identify even with single crystal x-ray diffraction. In other terms, distinguishing a salt from a co-crystal generally requires evidence of ionic interactions, as opposed to merely non-ionic interactions. Accordingly, although the novel compositions described herein are described as salts, it is noted that in some embodiments, it may not be known whether a given product exists in salt, co-crystal, or salt co-crystal form or in some type of intermediate form (e.g., wherein the proton has not been transferred to a basic site, but may reside in space between the donor coformer and acceptor).

The nicotine salts, co-crystals, and salt co-crystals described herein can be incorporated into various products, including tobacco-containing products. The important characteristics of nicotine salts, co-crystals, and salt co-crystals for use in different types of products vary, as will be discussed in detail below.

The nicotine salts, co-crystals, and salt co-crystals provided herein can, in some embodiments, be used as compositions in the manufacture of smoking articles. For example, salts, co-crystals, and salt co-crystals prepared in accordance with the present invention can be mixed with casing materials and applied to tobacco as a casing ingredient or as a top dressing. Still further, salts, co-crystals, and salt co-crystals of the present disclosure can be incorporated into a cigarette filter (e.g., in the filter plug, plug wrap, or tipping paper) or incorporated into cigarette wrapping paper, preferably on the inside surface, during the cigarette manufacturing process. See, for example, the description and references related to tobacco isolates used in smoking articles set forth in US Pat. Pub. No. 2012/0192880 to Dube et al., which is incorporated by reference herein. Representative tobacco blends, non-tobacco components, and representative cigarettes manufactured therefrom are also set forth in the Dube et al. reference noted above.

Typically, the amount of nicotine salt, co-crystal, or salt co-crystal incorporated into a smoking article is that amount sufficient to provide the desired amount of free nicotine in the mainstream smoke produced therefrom. For example, in some embodiments, the smoking article may provide nicotine in an amount of about 0.1 mg to about 10 mg, about 0.5 mg to about 9 mg, or about 1 mg to about 8 mg. Accordingly, the amount of nicotine salt, co-crystal, or salt co-crystal incorporated into the smoking article can be, for example, that amount sufficient to produce these amounts of nicotine when the article is used.

Figure 18:
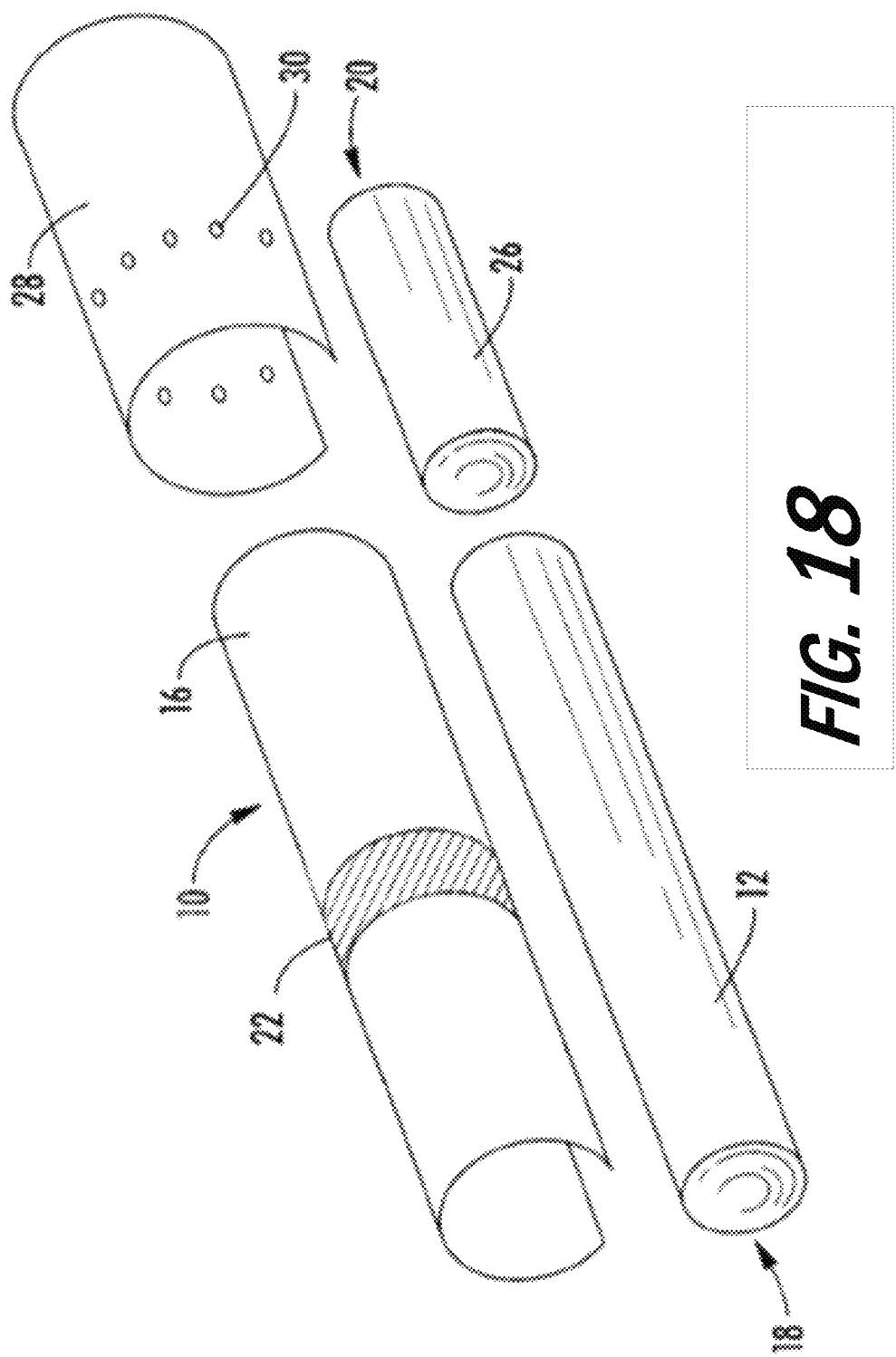
FIG. 18 is an exploded perspective view of a smoking article having the form of a cigarette, showing the smokable material, the wrapping material components, and the filter element of the cigarette.

Referring to FIG. 18, there is shown a smoking article 10 in the form of a cigarette and possessing certain representative components of a smoking article that can contain the formulation of the present invention. The cigarette 10 includes a generally cylindrical rod 12 of a charge or roll of smokable filler material (e.g., about 0.3 g to about 1.0 g of smokable filler material such as tobacco material) contained in a circumscribing wrapping material 16. The rod 12 is conventionally referred to as a "tobacco rod." The ends of the tobacco rod 12 are open to expose the smokable filler material. The cigarette 10 is shown as having one optional band 22 (e.g., a printed coating including a film-forming agent, such as starch, ethylcellulose, or sodium alginate) applied to the wrapping material 16, and that band circumscribes the cigarette rod in a direction transverse to the longitudinal axis of the cigarette. The band 22 can be printed on the inner surface of the wrapping material (i.e., facing the smokable filler material), or less preferably, on the outer surface of the wrapping material.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough.

A ventilated or air diluted smoking article can be provided with an optional air dilution means, such as a series of perforations 30, each of which extend through the tipping material and plug wrap. The optional perforations 30 can be made by various techniques known to those of ordinary skill in the art, such as laser perforation techniques. Alternatively, so-called off-line air dilution techniques can be used (e.g., through the use of porous paper plug wrap and pre-perforated tipping paper). The salts of the invention can be incorporated within any of the components of a smoking article, including but not limited to, as a component of the tobacco charge, as a component of the wrapping paper (e.g., included within the paper or coated on the interior or exterior of the paper), as an adhesive, as a filter element component, and/or within a capsule located in any region of the smoking article.

The temperature at which nicotine, the coformer component (or components), and any degradation products thereof are released from a nicotine salt, co-crystal, or salt co-crystal can be a relevant consideration in the context of smoking articles. It is typically important that nicotine is released from the salt, co-crystal, or salt co-crystal (i.e., that the nicotine transfers to the mainstream smoke and is delivered to the user) at the burn temperature of the smoking article. It can also be important in some embodiments to ensure that certain undesirable coformers and/or degradation products thereof are not transferred to the mainstream smoke (and delivered to the user). The relevant temperature may vary slightly, depending upon the specific location(s) of the salt, co-crystal, or salt co-crystal within the smoking article. For example, in certain embodiments, the temperature at which a smoking article burns (and thus the temperature to which the salt is exposed) can be between at least about 100° C., at least about 200° C., or at least about 500° C., including between about 100° C. and about 500° C. in certain regions of a smoking article and between about 600° C. and about 900° C. in other regions of a smoking article. These considerations can impact selection of the salts, co-crystals, or salt co-crystals that are suitable for a particular application.

In other embodiments, the nicotine salts, co-crystals, and salt co-crystals disclosed herein can be incorporated within smokeless tobacco products. Representative smokeless tobacco compositions according to the present invention can have various types of formats and configurations, and as a result, the character, nature, behavior, consistency, shape, form, size and weight of the composition can vary. In some embodiments, the nicotine salts, co-crystals, and salt co-crystals disclosed herein can be incorporated into smokeless tobacco products, such as loose moist snuff (e.g., snus); loose dry snuff; chewing tobacco; pelletized tobacco pieces; extruded or formed tobacco strips, pieces, rods, cylinders or sticks; finely divided ground powders; finely divided or milled agglomerates of powdered pieces and components; flake-like pieces; molded tobacco pieces; gums; rolls of tape-like films; readily water-dissolvable or water-dispersible films or strips; meltable compositions; lozenges; pastilles; or capsule-like materials possessing an outer shell and an inner region. The shape of a representative composition can be generally spherical, cylindrical (e.g., ranging from the general shape of a flattened disc to the general shape of a relatively long, slender stick), helical, obloid, square, rectangular, or the like; or the composition can have the form of a bead, granular powder, crystalline powder, capsule, film, strip, gel, or the like. The shape of the composition can resemble a wide variety of pill, tablet, lozenge, capsule, and caplet types of products. Various types of smokeless tobacco products are described or referenced in US Pat. Pub. Nos. 2013/0206150 to Duggins et al.; 2013/0074855 to Holton, Jr.; 2012/0118310 to Cantrell et al.; 2012/0138073 to Cantrell et al.; 2012/0138074 to Cantrell et al.; and 2012/0152265 to Dube et al., which are all incorporated herein by reference.

Figure 19:
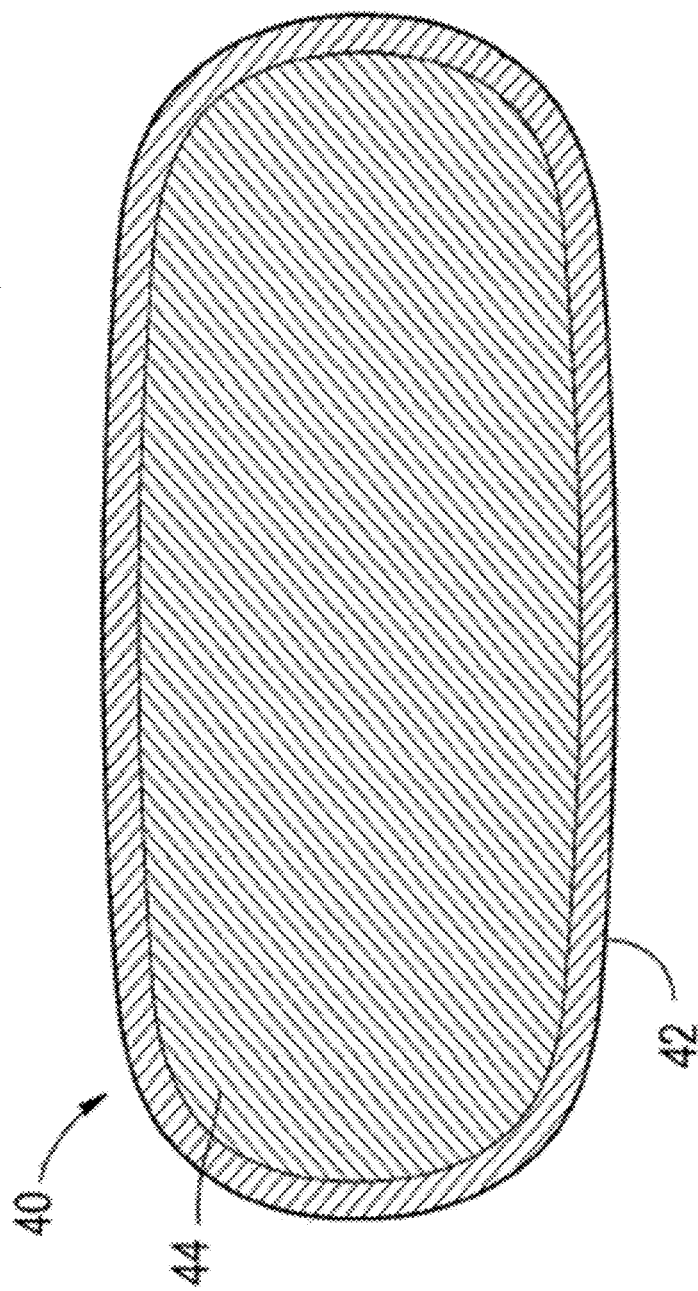
FIG. 19 is a cross-sectional view of a smokeless tobacco product embodiment, taken across the width of the product, showing an outer pouch filled with a smokeless tobacco composition of the invention.

Referring to FIG. 19, a representative snus type of tobacco product comprising one or more nicotine salts, co-crystals, or salt co-crystals according to the present disclosure is shown. In particular, FIG. 19 illustrates a smokeless tobacco product 40 having a water-permeable outer pouch 42 containing a smokeless tobacco composition 44. Any of the components of the tobacco product can comprise one or more nicotine salts, co-crystals, or salt co-crystals, according to the present disclosure (e.g., the interior or exterior of the pouch lining or a portion of the smokeless tobacco composition contained therein).

Other exemplary smokeless tobacco products into which the salts, co-crystals, and salt co-crystals described herein can be incorporated can have the form of a gum, lozenge, tablet, microtab, or other tablet-type product. See, for example, the types of nicotine-containing lozenges, lozenge formulations, lozenge formats and configurations, lozenge characteristics and techniques for formulating or manufacturing lozenges set forth in U.S. Pat. Nos. 4,967,773 to Shaw; U.S. Pat. No. 5,110,605 to Acharya; U.S. Pat. No.

5,733,574 to Dam; U.S. Pat. No. 6,280,761 to Santus; U.S. Pat. No. 6,676,959 to Andersson et al.; U.S. Pat. No. 6,248,760 to Wilhelmsen; and U.S. Pat. No. 7,374,779; US Pat. Pub. Nos. 2013/0074855 and 2013/0078307 to Holton, Jr.; 2001/0016593 to Wilhelmsen; 2004/0101543 to Liu et al.; 2006/0120974 to Mcneight; 2008/0020050 to Chau et al.; 2009/0081291 to Gin et al.; and 2010/0004294 to Axelsson et al.; and 2013/0312774 to Holton, Jr., which are all incorporated herein by reference.

One representative type of smokeless tobacco product comprising one or more of the nicotine salts, co-crystals, or salt co-crystals described herein is a lozenge, e.g., as substantially described in US Pat. App. Pub. Nos. 2013/0312774, 2013/0074856, and 2013/0074855, all to Holton, Jr., which are incorporated herein by reference. Such lozenges can comprise, in addition to one or more nicotine salts, co-crystals, or salt-co-crystals, a majority of one or more sugar alcohols (e.g., isomalt and maltitol syrup), e.g., in an amount of at least about 50% by weight, at least about 70% by weight, at least about 80% by weight, or at least about 90% by weight. Other ingredients of particular interest in such lozenge products include, but are not limited to, salts (e.g., NaCl), sweeteners (e.g., sucralose), and one or more flavorings.

The amount of nicotine salt, co-crystal, or salt co-crystal incorporated within a smokeless tobacco composition can vary and can be dependent, in part, on the specific type of smokeless tobacco composition. Clearly, the amount of a given nicotine salt, co-crystal, or salt co-crystal to be incorporated within a product will depend on the desired nicotine content of that product, and can be calculated based on the mass of the coformer and the stoichiometry of the salt, co-crystal, or salt co-crystal. Exemplary amounts include from about 0.1% by weight of the consumable material to about 10% by weight of the consumable or inhalable material. For example, for a lozenge, the amount of nicotine salt, co-crystal, or salt co-crystal is at least about 0.5%, generally at least about 1%, often at least about 1.5%, often at least about 2%, often at least about 2.5%, and frequently at least about 3% by weight of the product, e.g., about 0.5% to about 10%, including about 1% to about 5% by weight of the product. The amount of nicotine salt, co-crystal, or salt co-crystal can be determined based on the desired nicotine content in the lozenge.

Various other substances can be added to the smokeless tobacco compositions comprising the nicotine salts, co-crystals, or salt co-crystals of the present invention. For example, excipients such as fillers or carriers for active ingredients (e.g., calcium polycarbophil, microcrystalline cellulose, hydroxypropylcellulose, sodium carboxymethylcellulose, cornstarch, silicon dioxide, calcium carbonate, lactose, and starches including potato starch, maize starch, etc.), thickeners, film formers and binders (e.g., hydroxypropyl cellulose, hydroxypropyl methylcellulose, acacia, sodium alginate, gum arabic, lecithin, xanthan gum and gelatin), antiadherents (e.g., talc), glidants (e.g., colloidal silica), humectants (e.g., glycerin), preservatives and antioxidants (e.g., sodium benzoate and ascorbyl palmitate), surfactants (e.g., polysorbate 80), dyes or pigments (e.g., titanium dioxide or D&C Yellow No. 10), and lubricants or processing aids (e.g., calcium stearate or magnesium stearate) are added to the compositions in certain embodiments. Other exemplary types of ingredients include salts (e.g., sodium chloride, potassium chloride, sodium citrate, potassium citrate, sodium acetate, potassium acetate, and the like), natural sweeteners (e.g., fructose, sucrose, glucose, maltose, vanillin, ethyl vanillin glucoside, mannose, galactose, lactose, and the like), artificial sweeteners (e.g., sucralose, saccharin, aspartame, acesulfame K, neotame and the like), pH adjusters or buffering agents (e.g., metal hydroxides, preferably alkali metal hydroxides such as sodium hydroxide and potassium hydroxide, and other alkali metal buffers such as metal carbonates, preferably potassium carbonate or sodium carbonate, or metal bicarbonates such as sodium bicarbonate, and the like), effervescing materials such as certain acid/base combinations, oral care additives (e.g., thyme oil, eucalyptus oil, and zinc), preservatives (e.g., potassium sorbate, and the like), syrups (e.g., honey, high fructose corn syrup, and the like), and mixtures thereof. In certain embodiments, the smokeless tobacco composition can include lipid components that provide a meltable composition that melts (as opposed to merely dissolving) in the oral cavity, such as compositions set forth in US Pat. Pub. No. 2012/0037175 to Cantrell et al., which is incorporated by reference herein. Exemplary encapsulated additives that can be included within the smokeless tobacco products disclosed herein are described, for example, in WO 2010/132444 to Atchley, which has been previously incorporated by reference herein. See also, the smokeless tobacco ingredients set forth in US Pat. Pub. Nos. 2012/0055494 to Hunt et al. and 2012/0199145 to Byrd et al., which are incorporated by reference herein.

The manners and methods used to formulate and manufacture the smokeless tobacco product can vary. Ingredients, including the nicotine salts, co-crystals, or salt co-crystals described herein, can be combined and processed into the desired composition by techniques such as extrusion, compression, molding, spraying, and the like. It is noted that certain considerations noted above for electronic smoking articles are not relevant in the context of a smokeless tobacco product. For example, nicotine salts, co-crystals, or salt co-crystals that are useful in smokeless tobacco products need not transfer to aerosol form at a given temperature. In smokeless tobacco products, the main consideration is that the nicotine salt, co-crystal, or salt co-crystal contained therein can provide nicotine when the smokeless tobacco product is placed in the mouth of the user (i.e., at some point during residence of the smokeless tobacco product in the mouth of the user). Accordingly, certain nicotine salts, co-crystals, or salt co-crystals that are useful for one type of tobacco product may not be useful for others.

Figure 20:
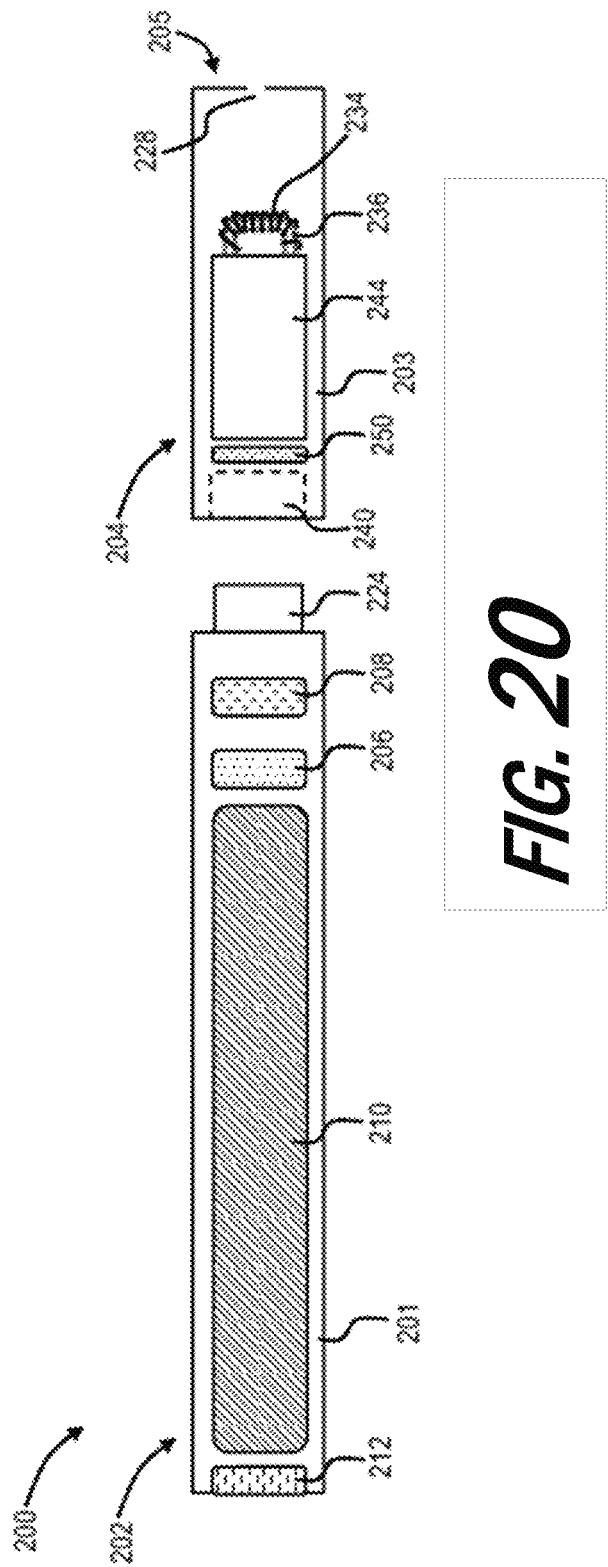
FIG. 20 is a cross-sectional view of an electronic smoking article, which can encompass a variety of combinations of components useful in forming an electronic aerosol delivery device.

In certain embodiments, the nicotine salts, co-crystals, and salt co-crystals provided according to the present disclosure are incorporated within electronic smoking articles. An exemplary embodiment of an electronic smoking article 200 incorporating a nicotine salt, co-crystal, or salt co-crystal according to the present disclosure is shown in FIG. 20. As illustrated therein, a control body 202 can be formed of a housing 201 that can include a control component 206, a flow sensor 208, a battery 210, and an LED 212. The electronic smoking article also may comprise a cartridge 204 that can be formed of a housing 203 enclosing a reservoir 244 that is in fluid communication with a transport element 236 adapted to wick or otherwise transport an aerosol precursor composition stored in the reservoir to a heater 234 (e.g., a resistive heating wire that may be coiled around at least a portion of the transport element). Exemplary reservoirs and transport elements are disclosed in US Pat. Pub. No. 2014/0261487 to Chapman et al., and exemplary heaters are disclosed in US Pat. Pub. No. 2014/0157583 to Ward et al., the disclosures of which are incorporated herein by reference in their entireties. An opening 228 may be present in the cartridge housing 203 at a mouthend 205 thereof to allow for egress of formed aerosol from the cartridge 204.

Such components are representative of the components that may be present in a control body and/or cartridge and are not intended to limit the scope of components that are encompassed by the present disclosure.

The cartridge 204 may be adapted to engage the control body 202 through a press-fit engagement between the control body projection 224 and the cartridge receptacle 240. Such engagement can facilitate a stable connection between the control body 202 and the cartridge 204 as well as establish an electrical connection between the battery 210 and control component 206 in the control body and the heater 234 in the cartridge. Other types of connections (e.g., a screw thread connection) also are encompassed. The electronic smoking article 200 may be adapted for air intake, which may be provided in a coupler as described, for example, in US Pat. Pub. No. 2014/0261408 to DePiano et al., the disclosure of which is incorporated herein by reference in its entirety. The cartridge 204 also may include one or more electronic components 250, which may include an IC, a memory component, a sensor, or the like. The electronic component 250 may be adapted to communicate with the control component 206 so as to provide an input. See, for example, US Pat. Pub. Nos. 2014/0096781 to Sears et al. and 2014/0096782 to Ampolini et al., the disclosures of which are incorporated herein by reference in their entirety.

The electronic smoking article can encompass a variety of combinations of components useful in forming an electronic aerosol delivery device. Reference is made for example to the following: a reservoir and heater system for controllable delivery of multiple aerosolizable materials disclosed in US Pat. Pub. No. 2014/0000638 to Sebastian et al.; microheaters as disclosed in US Pat. Pub. No. 2014/0060554 to Collett et al.; carbon-based cartridges and components thereof, as disclosed US Pat. Pub. No. 2013/0255702 to Griffith, Jr. et al.; single-use cartridges as disclosed in US Pat. Pub. No. 2014/0060555 to Chang et al.; aerosol precursor transport elements, such as disclosed in US Pat. Pub. No. 2014/0209105 to Sears et al.; charging components, such as an adaptor disclosed in US Pat. Pub. No. 2014/0261495 to Novak, III et al.; vibration components, such as disclosed in US Pat. Pub. No. 2015/0020825 to Galloway et al.; and batteries, such as disclosed in U.S. Pat. Pub. No. 2010/0028766 to Peckerar et al.

Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

In certain embodiments, the aerosol precursor comprises a nicotine salt, co-crystal, or salt co-crystal as disclosed herein. In one embodiment, the aerosol precursor composition can comprise, for example, a polyhydric alcohol (e.g., glycerin, propylene glycol, or a combination thereof), water, a nicotine salt, co-crystal, or salt co-crystal as described herein, and a flavorant (e.g., menthol). Exemplary flavoring agents include vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Flavoring agents also can include acidic or basic characteristics (e.g., organic acids, such as levulinic acid, succinic acid, and pyruvic acid). Representative types of aerosol precursor compositions are set forth in U.S. Pat. No. 4,793,365 to Sensabaugh, Jr. et al.; U.S. Pat. No. 5,101,839 to Jakob et al.; U.S. Pat. Pub. No. 2013/0008457 to Zheng et al.; and Chemical and Biological Studies on New Cigarette Prototypes that Heat Instead of Burn Tobacco, R. J. Reynolds Tobacco Company Monograph (1988). The disclosures of all of the foregoing documents are incorporated herein by reference in their entireties.

One or more acid components can be included within the aerosol precursor, e.g., to modify the sensory characteristics of the aerosol precursor and the aerosol produced therefrom. Organic acids particularly may be incorporated into the aerosol precursor to affect the flavor, sensation, and/or organoleptic properties of nicotine. Such organic acids can be included in the aerosol precursor with nicotine in varying amounts ranging from greater than equimolar to less than equimolar (based on total organic acid content) with the nicotine. A range of organic acids can be used in accordance with such embodiments, e.g., as set forth in Perfetti, *Beitrage Tabakforschung Int.*, 12, 43-54 (1983), which is incorporated herein by reference. Certain exemplary organic acids that may be useful include, but are not limited to, such acids as tartaric acid, ascorbic acid, fumaric acid, citric acid, malic acid, lactic acid, aspartic acid, salicylic acid, 4-amino salicylic acid, N-acetyl-4-aminosalicylic acid, p-toluenesulfonic acid, succinic acid, pyruvic acid, formic acid, acetic acid, propionic acid, isobutyric acid, butyric acid, alpha-methylbutyric acid, 2-ketobutyric acid, isovaleric acid, beta-methylvaleric acid, caproic acid, 2-furoic acid, phenylacetic acid, heptanoic acid, octanoic acid, nonanoic acid, oxalic acid, malonic acid, glycolic acid, levulinic acid, 4-aminobenzoic acid, 4-acetamidobenzoic acid, 3-hydroxybenzoic acid, 2,5-dihydroxybenzoic acid, 2,3-dihydroxybenzoic acid, 2,4-dihydroxybenzoic acid, 3,4-dihydroxybenzoic acid, vanillic acid, mucic acid, cyclamic acid, benzenesulfonic acid, 2-hydroxyethanesulfonic acid, 1-hydroxy-2-naphthoic acid, ketoglutaric acid, D-glucuronic acid, maleic acid, glutamic acid, L-pyroglutamic acid, nicotinic acid, isonicotinic acid, gallic acid, phthalic acid, mandelic acid, hippuric acid, cinnamic acid, adipic acid, orotic acid, sorbic acid, clofibric acid, tauric acid, and combinations of two or more such organic acids. By using a nicotine salt, co-crystal, or salt co-crystal in place of nicotine, it may be possible in certain embodiments to reduce and or eliminate the amount of acid advantageously incorporated within the aerosol precursor.

The amount of aerosol precursor composition that is used within the smoking article is such that the article exhibits acceptable sensory and organoleptic properties, and desirable performance characteristics. For example, it is highly preferred that sufficient aerosol precursor composition components, such as glycerin and/or propylene glycol, be employed in order to provide for the generation of a visible mainstream aerosol that in many regards resembles the appearance of tobacco smoke. Typically, the amount of aerosol-generating material incorporated into the smoking article is in the range of about 1.5 g or less, about 1 g or less, or about 0.5 g or less. The amount of aerosol precursor composition can be dependent upon factors such as the number of puffs desired per cartridge used with the smoking article. It is desirable for the aerosol-generating composition not to introduce significant degrees of unacceptable off-taste, filmy mouth-feel, or an overall sensory experience that is significantly different from that of a traditional type of cigarette that generates mainstream smoke by burning tobacco cut filler. The selection of the particular aerosol-generating material and reservoir material, the amounts of those components used, and the types of tobacco material used, can be altered in order to control the overall chemical composition of the mainstream aerosol produced by the smoking article.

Typically, the amount of nicotine incorporated into an aerosol precursor of an electronic smoking article is that amount sufficient to provide the desired amount of free nicotine in the aerosol produced therefrom. For example, the article may provide nicotine in an amount of about 0.01 mg to about 0.5 mg, about 0.05 mg to about 1 mg, about 0.08 mg to about 0.5 mg, about 0.1 mg to about 0.3 mg, or about 0.15 mg to about 0.25 mg per puff on the article. Accordingly, the amount of nicotine salt, co-crystal, or salt co-crystal incorporated into the aerosol precursor can be, for example, that amount sufficient to produce these amounts of nicotine when the article is used.

When the nicotine salts, co-crystals, or salt co-crystals described herein are used in electronic smoking articles, the temperature at which nicotine is released into aerosol form from the salt, co-crystal, or salt co-crystal is an important consideration. It is typically important that nicotine is released from the salt, co-crystal, or salt co-crystal (i.e., that the nicotine transfers to aerosol form) at the operating temperature of the electronic smoking articles. Although not intended to be limiting, exemplary operating temperatures of electronic smoking articles are within the range of about 100° C. to about 500° C. (e.g., about 120° C. to about 300° C.). Accordingly, selection of an appropriate nicotine salt, co-crystal, or salt co-crystal for incorporation into such products can depend, in part, on the characteristics of the bond between the nicotine and the coformer and the volatility of the salt, co-crystal, or salt co-crystal. For example, nicotine citrate may not be a good salt for an electronic smoking article because it is not sufficiently volatile.

Furthermore, in some embodiments, the temperature at which the coformer component (or components) is released from a nicotine salt, co-crystal, or salt co-crystal can be a relevant consideration. As it may not be advantageous for certain coformers (e.g., certain acids) to be present in the aerosol (and delivered to the user), it can be important to consider the temperature at which not only the nicotine, but also the coformer of the nicotine salt, co-crystal, or salt co-crystal transfers to aerosol form. In other embodiments, the coformer(s) of a given nicotine salt, co-crystal, or salt co-crystal may be desirably contained in the aerosol and desirably delivered to the user. In such cases, it may be advantageous to ensure that such coformer(s) are sufficiently volatile at the temperature of use of the electronic smoking article. Additionally, any degradation products produced via heating nicotine salts, co-crystals, or salt co-crystals to the relevant temperature (i.e., the typical operation temperature of an electronic smoking article) should also be evaluated and taken into consideration during product preparation and selection for a particular application. In particular, in certain embodiments, acid degradation products produced via heating nicotine salts, co-crystals, or salt co-crystals to the relevant temperature should be evaluated and taken into consideration.

Accordingly, in certain embodiments, following preparation of the nicotine salts, co-crystals, or salt co-crystals described herein, they are analyzed to evaluate whether the nicotine and/or coformer and/or degradation products thereof transfer from the aerosol precursor to the aerosol. Such analysis can be conducted, for example, by high performance liquid chromatography and/or gas chromatography of the condensate collected from the aerosol. Both the presence and amount of nicotine and/or coformer and/or degradation products thereof is evaluated to determine whether a given salt, co-crystal, or salt co-crystal is a good candidate for incorporation within an electronic smoking article.

In still further embodiments, nicotine salts, co-crystals, and/or salt co-crystals disclosed herein may be incorporated within pharmaceutical products. For example, a nicotine salt, co-crystal, or salt co-crystal can be used as a replacement for, or in addition to, the nicotine in nicotine-containing pharmaceutical products. Such products can be used for treatment of a wide variety of conditions, diseases, and disorders responsive to stimulation of one or more types of nicotinic acetylcholinergic receptors (nAChRs). The products can be used to treat those types of conditions, diseases, and disorders that have been reported to be treatable through the use or administration of nicotine as an agonist of nAChRs. As such, the products can be used to treat various CNS conditions, diseases, and disorders, and the compositions also can be used as smoking cessation aids (i.e., as components of NRT). The combined amount of nicotine present (including nicotine present as the salt, co-crystal, and/or salt co-crystal form and, optionally, any one or more other forms of nicotine) is preferably that amount effective to treat some symptoms of, or prevent occurrence of the symptoms of, a condition, disease, or disorder from which the subject or patient suffers. Exemplary conditions, diseases or disorders that can be treated include cognitive disorders such as Alzheimer's disease and attention deficit disorder, schizophrenia, Parkinson's disease, Tourette's syndrome, ulcerative colitis, dry eye disease, hypertension, depression, overactive bladder, obesity, seven year itch/scabies, and hemorrhoids. Such products may also find use as a treatment to reduce stress or pain and/or as a smoking cessation aid.

The shape of the pharmaceutical products can resemble a wide variety of pill, tablet, lozenge, capsule, caplet, pouch and gum types of products that traditionally have been employed for the administration of pharmaceutical types of products. The general nature of a representative composition can be soft or hard to the feel, or of intermediate softness or hardness; and as such, the composition can be considered to be malleable, flexible, chewy, resilient, brittle, or the like. Pharmaceutical products containing nicotine salts, co-crystals, or salt co-crystals as provided herein are not limited to oral products, and such compositions as creams (including salves, ointments, and pastes), liquids (e.g., sprays or enemas), and the like are also encompassed by the present invention as well. In addition, the nicotine salts, co-crystals, and salt co-crystals disclosed herein can also be incorporated within various devices for delivery, such as inhalers (e.g., metered dose inhalers, dry powder inhalers, and nebulizers). Pharmaceutical products according to the present invention can contain, in addition to a nicotine salt, co-crystal, and/or salt co-crystal as described herein, one or more pharmaceutically acceptable components, e.g., excipients (e.g., salts, sweeteners, fillers, flavorants, antiadherents, glidants, preservatives and antioxidants, surfactants, dyes or pigments, lubricants, and/or processing aids).

The application as written focuses on the incorporation of novel nicotine salts, co-crystals, and salt co-crystals. However, it is noted that, in some embodiments, known nicotine salts can be employed in compositions disclosed herein to provide novel compositions and/or novel products incorporating such compositions. For example, although not intended to be limiting, known salts such as nicotine L-malate (CAS RN 253180-13-1), nicotine 4-acetamidobenzoic acid salt (CAS RN 110441-65-1), nicotine 3-hydroxybenzoic acid (CAS RN 1644394-41-1, disclosed, for example, in Int. App. Pub. No. WO2015/006652), nicotine 2,5-dihydroxybenzoic acid (CAS RN 6012-21-1), nicotine 4-aminosalicylic acid salt (1-hydroxy-4-amino benzoic acid salt) (CAS RN 20334-41-2), nicotine salicylic acid salt (2-hydroxybenzoic acid salt) (CAS RN 29790-52-1), nicotine phthalic acid salt (1,2-benzene dicarboxylic acid salt) (CAS RN 88660-55-3), nicotine N-acetyl-4-aminosalicylic acid salt (N-acetyl-2-hydroxy-4-aminobenzoic acid salt) (CAS RN 900789-26-6), and/or nicotine di-L-(+)-tartrate dihydrate (CAS RN 6019-06-3) can be used in the compositions and products disclosed herein.

It is further noted that, although the application as written focuses on the formation of nicotine salts, co-crystals, and salt co-crystals and on the incorporation of such formed nicotine salts, co-crystals, and salt co-crystals into various products, it may be possible, in some embodiments, to form such nicotine salts, co-crystals, and salt co-crystals in situ. For example, nicotine can be combined with one or more coformers as broadly described herein, and optionally, other components (e.g., those types of components typically contained in the product to be formed), and a nicotine salt, co-crystal, or salt co-crystal is formed in situ. In other words, although it is often advantageous for reasons disclosed herein, isolation and/or purification of the nicotine salt, co-crystal, or salt co-crystal is not required in all embodiments prior to introduction into a product.

For example, in one embodiment, an aerosol precursor of an electronic smoking article can be prepared by mixing a nicotine salt, co-crystal, or salt co-crystal with desired aerosol precursor components (e.g., carriers and flavorants) or can be prepared by mixing nicotine, a coformer (e.g., an acid), and desired aerosol precursor components. See, for example, the methods of incorporating certain salts into aerosol devices in Int. App. Pub. No. WO2014/182736 to Ploom, Inc., which is incorporated herein by reference.

Aspects of the present invention are more fully illustrated by the following examples, which are set forth to illustrate certain aspects of the present invention and are not to be construed as limiting thereof.

EXPERIMENTAL

General
X-Ray Powder Diffraction (XRPD)

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The software used for data collection was Diffrac Plus XRD Commander v2.6.1 and the data was analyzed and presented using Diffrac Plus EVA v13.0.0.2 or v15.0.0.0.

Samples were run under ambient conditions as flat plate specimens using powder as received. Each sample was gently packed into a cavity cut into a polished, zero-background (510) silicon wafer. The sample was rotated in its own plane during analysis.

The details of the data collection are: Angular range: 2 to 42° 2θ; Step size: 0.05° 2θ; and collection time: 0.5 s/step.
Single Crystal X-Ray Diffraction (SCXRD)

Data were collected on an Oxford Diffraction Supernoval Dual Source, Cu at Zero, Atlas CCD diffractometer equipped with an Oxford Cryosystems Cobra cooling device. The data was collected using Cu Kα radiation. Structures were typically solved using either the SHELXS or SHELXD programs and refined with the SHELXL program as part of the Bruker AXS SHELXTL suite (V.6.10). Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.
$^1$H Nuclear Magnetic Resonance ($^1$H NMR)

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in DMSO-$d_6$, unless otherwise stated. Off-line analysis was carried out using ACD Spectrus Processor 2014.
Differential Scanning Calorimetry (DSC)

Certain DSC data were collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminum pan, was heated at 10° C./min from 25° C. to 180° C. A purge of dry nitrogen at 50 ml/min was maintained over the sample.

The instrument control software was Advantage for Q Series v2.8.0.394 and Thermal Advantage v5.5.3 and the data were analyzed using Universal Analysis v4.5A.

Other DSC data were collected on a TA Instruments Discovery DSC equipped with a 50 position auto-sampler. The calibration for thermal capacity was carried out using sapphire and the calibration for energy and temperature was carried out using certified indium. Typically 0.5-3 mg of each sample, in a pin-holed aluminum pan, was heated at 10° C./min from 25° C. to 180° C. A purge of dry nitrogen at 50 ml/min was maintained over the sample. The instrument control and data analysis software was TRIOS v3.2.0.3877.
Thermo-Gravimetric Analysis (TGA)

Certain TGA data were collected on a TA Instruments Q500 TGA, equipped with a 16 position auto-sampler. The instrument was temperature calibrated using certified Alumel and Nickel. Typically 5-10 mg of each sample was loaded onto a pre-tared aluminum DSC pan and heated at 10° C./min from ambient temperature to 180° C. A nitrogen purge at 60 ml/min was maintained over the sample. The instrument control software was Advantage for Q Series v2.5.0.256 and Thermal Advantage v5.5.3 and the data were analyzed using Universal Analysis v4.5A.

Other TGA data were collected on a TA Instruments Discovery TGA, equipped with a 25 position auto-sampler. The instrument was temperature calibrated using certified Alumel and Nickel. Typically 5-10 mg of each sample was loaded onto a pre-tared aluminum DSC pan and heated at 10° C./min from ambient temperature to 180° C. A nitrogen purge at 60 ml/min was maintained over the sample. The instrument control and data analysis software was TRIOS v3.2.0.3877.

Polarized Light Microscopy (PLM)

Certain samples were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarized light, coupled to a λ false-color filter.

Certain samples were studied on a Nikon SMZ1500 polarized light microscope with a digital video camera connected to a DS Camera Control Unit DS-L2 for image capture. A small amount of each sample was placed on a glass slide, mounted in immersion oil and covered with a glass slip, the individual particles being separated as well as possible. The sample was viewed with appropriate magnification and partially polarized light, coupled to a λ false-color filter.

Scanning Electron Microscopy (SEM)

Data were collected on a Phenom Pro Scanning Electron Microscope. A small quantity of sample was mounted onto an aluminum stub using conducting double-sided adhesive tape. A thin layer of gold was applied using a sputter coater (20 mA, 120 s). Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. Data collection and analysis were done using Tiamo v2.2.

Gravimetric Vapor Sorption (GVS)

Sorption isotherms were obtained using a SMS DVS Intrinsic moisture sorption analyzer, controlled by DVS Intrinsic Control software v 1.0.1.2 (or v 1.0.1.3). The sample temperature was maintained at 25° C. by the instrument controls. The humidity was controlled by mixing streams of dry and wet nitrogen, with a total flow rate of 200 ml/min The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was carried out using Microsoft Excel using DVS Analysis Suite v6.2 (or 6.1 or 6.0).

TABLE 1

| Method for SMS DVS Intrinsic experiments | |
| --- | --- |
| Parameter | Value |
| Adsorption - Scan 1 | 40-90 |
| Desorption/Adsorption - Scan 2 | 90-0, 0-40 |
| Intervals (% RH) | 10 |

TABLE 1-continued

| Method for SMS DVS Intrinsic experiments | |
| --- | --- |
| Parameter | Value |
| Number of Scans | 2 |
| Flow rate (ml/min) | 200 |
| Temperature (° C.) | 25 |
| Stability (° C./min) | 0.2 |
| Sorption Time (hours) | 6 hour time out |

The sample is recovered after completion of the isotherm and re-analyzed by XRPD.

Example 1

Screen Por preparation of Nicotine Salt Co-Crystals

Various nicotine salts were prepared to carry out co-crystal screens. Salts were prepared as described below and analyzed by XRPD and 1H NMR to confirm salt formation and to identify the crystalline form obtained.

Nicotine L-Malate Salt

L-malic acid (2.9 g) was dissolved in THF (15 mL) by stirring for 10 minutes at 25° C. Nicotine (5.7 mL, 1.7 equiv.) was added and the solution was seeded with about 3 mg nicotine salicylate (mistakenly added rather than nicotine malate; however, no salicylate salt or salicylic acid was observed in the final product). A gel was formed at the bottom of the mixture and it was stirred with a spatula, resulting in a gummy solid in suspension. After 20 minutes, a further amount of THF (10 mL) was added and the gummy solid was stirred at 25° C. overnight, after which time a white solid was isolated by filtration under suction and washing with heptane (2×10 mL). The solid was dried under vacuum at 25° C. overnight (5.4 g, 87% yield) and analyzed by XRPD and $^1$HNMR, which was consistent with previous data for nicotine malate (see US Pat. App. Publ. No. 2015/0344456 to Dull et al., which is incorporated herein by reference in its entirety)

Nicotine Salicylate Salt

Salicylic acid (4.8 g) was dissolved in THF (15 mL) by stirring for 5 minutes at 25° C. Nicotine (5.7 mL, 1.7 equiv.) was added but no precipitation was observed. The solution was seeded with 5 mg of previously prepared nicotine salicylate, after which precipitation was observed. The suspension was stirred at 25° C. for 40 minutes. The liquor was light-pink and the solid was filtered under suction and washed with heptane (10 mL) and THF (5 mL). The solid was dried under vacuum at 25° C. overnight (6.8 g, 66% yield) and analyzed by XRPD and $^1$HNMR, which was consistent with previously reported data for nicotine salicylate.

Nicotine Orotate Salt

Orotic acid (4.8 g) was treated with ethyl acetate (25 mL) by stirring for 15 minutes at 50° C. Nicotine (5.0 mL, 1.0 equiv.) was added and the mixture was stirred at 50° C. for ~15 minutes, with precipitation observed over time. A ramp was set up to cool the sample down to 5° C. at 0.1° C./min. When the sample reached about 40° C., the solid appeared to be stationary at the bottom of the vial and was stirred manually with a spatula to ease mixing and crystallization. The solution was seeded with nicotine monoorotate after about an hour (at 40° C.) and further precipitation was observed. The ramp was continued overnight and the resulting mixture was filtered under suction and the solid was washed with heptane (3×10 mL). The washed solid was dried overnight under vacuum at room temperature (2.4 g, 25% yield) and analyzed by XRPD and $^1$H NMR, which were indicative of a nicotine monoorotate salt (see US Pat. App. Publ. No. 2016/0185750 to Dull et al., which is incorporated herein by reference in its entirety)

Nicotine Fumarate Salt

Fumaric acid (3.6 g) was treated with THF (25 mL) by stirring for 15 minutes at 50° C. An excess of nicotine (10.0 mL, 2.0 equiv.) was added and the mixture was stirred at 50° C. for ~15 minutes, with precipitation observed over time. A ramp was set up to cool the sample down to 5° C. at 0.1° C./min. After around one hour, a thin suspension was observed and the liquid was light pink. The solution was seeded with nicotine fumarate (at 40° C.) and further precipitation was observed. The ramp was continued overnight and the resulting mixture was filtered under suction and the solid was washed with heptane (10 mL) and THF (50mL). The washed solid was dried overnight under vacuum at 25° C. (6.5 g, 76% yield) and analyzed by XRPD and $^1$HNMR, which were indicative of a nicotine fumarate salt (see US Pat. App. Publ. No. 2016/0185750 to Dull et al., which is incorporated herein by reference in its entirety)

Nicotine Mucate salt

Mucic acid (5.4 g) was treated with ethanol (25 mL) by stirring for 15 minutes at 25° C. Nicotine (10.0 mL, 2.4 equiv.) was added and the suspension was stirred at 25° C. for ~15 minutes. The suspension was seeded with nicotine mucate. The temperature was raised and maintained at 50° C. for 1 hour and then cooled to 5° C. at 0.1° C./min. After ~1 hour, a thick off-white suspension was observed. The resulting mixture was filtered under suction and the solid was washed with ethanol (3×20 mL). The washed solid was dried overnight under vacuum at 25° C. (8 g, 84% yield) and analyzed by XRPD, which was indicative of a new form of nicotine mucate (compare with data presented in US Pat. App. Publ. No. 2015/0344456, which is incorporated herein by reference in its entirety). $^1$H NMR analysis was consistent with a nicotine mucate salt, and further characterization of this salt is provided in Example 5, below.

Co-Crystal Screen

About 50 mg of various nicotine salts prepared as described above were weighed into 1.5 mL clear glass vials. A coformer (about 1.0 equivalents) was added to each (neat) in solid form (with the exception of methyl salicylate, which was added as a liquid), as shown below in Tables 2-8. Nitromethane or heptane (20 µL) and two stainless steel beads were added to each vial and the vials were capped. The mixtures were ground using a Fritsch planetary mill at 650 rpm for 2 hours. Blanks were also run using the nicotine salts and nitromethane (no coformers). Any solids obtained were analyzed by XRPD and any gels or oils were opened up for air drying and analyzed by XRPD.

TABLE 2

Co-crystal screen using nicotine L-malate salt in nitromethane

| Coformer | Observations after milling | XRPD |
|---|---|---|
| L-aspartic acid | Wet solid | Salt + coformer |
| Succinic acid* | Wet solid | New pattern + coformer |
| L-pyroglutamic acid | Gel - opened for air drying | N/A |
| Hippuric acid | Wet solid | Salt + coformer |
| L-ascorbic acid | Gummy solid | Salt + coformer |
| Nicotinamide | Wet solid | Salt + coformer |
| Ethyl vanillin | Yellow gel; opened for air drying; gummy solid observed after 4 days | Salt + coformer |

TABLE 2-continued

Co-crystal screen using nicotine L-malate salt in nitromethane

| Coformer | Observations after milling | XRPD |
|---|---|---|
| Sulfacetamide | Wet solid | Salt + coformer |
| Creatine | Wet solid | Salt + coformer |
| Saccharin | Colorless oil; opened for air drying | N/A |
| Vanillic acid | Wet solid | Salt + coformer |
| Methyl salicylate | Wet gummy solid | Salt |
| Blank (no coformer) | Wet solid | Salt |

*Material was further evaluated (see herein below)

TABLE 3

Co-crystal screen using nicotine salicylate salt in nitromethane

| Coformer | Observations after milling | XRPD |
|---|---|---|
| L-aspartic acid | Wet solid | Salt + coformer |
| Succinic acid | Colorless oil; opened for air drying | N/A |
| L-pyroglutamic acid | Gel - opened for air drying, gummy solid after one day | Salt |
| Hippuric acid | Wet solid | Salt + coformer |
| L-ascorbic acid | Gel; opened for air drying Gummy solid after one day | Coformer |
| Nicotinamide | Wet solid | Salt + coformer |
| Ethyl vanillin | Orange oil; opened for air drying | N/A |
| Sulfacetamide | Wet solid | Salt + coformer |
| Creatine | Wet solid | Salt + coformer |
| Saccharin | Colorless oil; opened for air drying | N/A |
| Vanillic acid | Yellow gel; opened for air drying Yellow solid after one day | Salt + coformer |
| Methyl salicylate | Gel; opened for air drying Yellow solid after one day | Salt |
| Blank (no coformer) | Wet solid | Salt |

TABLE 4

Co-crystal screen using nicotine mono orotate salt in nitromethane

| Coformer | Observations after milling | XRPD |
|---|---|---|
| L-aspartic acid | Wet solid | Monoorotate + coformer |
| Succinic acid* | Wet solid/paste | New pattern + monoorotate + diorotate + coformer |
| L-pyroglutamic acid | Wet solid/paste | Diorotate |
| Hippuric acid | Wet solid/paste | Diorotate + coformer |
| L-ascorbic acid | Wet solid/paste | Monoorotate + diorotate + coformer |
| Nicotinamide | Wet solid | Monoorotate + coformer |
| Ethyl vanillin | Yellow gel; opened for air drying; gummy solid observed after 1 day | Monoorotate + diorotate + coformer |
| Sulfacetamide | Wet solid | Monoorotate + diorotate + coformer |
| Creatine | Wet solid | Monoorotate + coformer |
| Saccharin | Wet solid | Poorly crystalline monoorotate + diorotate |
| Vanillic acid | Wet solid | Monoorotate + dioorotate + coformer |
| Methyl salicylate | Wet solid | Monoorotate + dioorotate |
| Blank monoorotate (no coformer) | Wet solid | Monoorotate |
| Blank diorotate (no coformer) | Wet solid | Dioorotate |

*Material was further evaluated (see herein below)

TABLE 5

Co-crystal screen using nicotine fumarate salt in nitromethane

| Coformer | Observations after milling | XRPD |
|---|---|---|
| L-aspartic acid | Wet solid | Coformer |
| Succinic acid | Oil; opened for drying | N/A |
| L-pyroglutamic acid | Oil; opened for drying | N/A |
| Hippuric acid | Gummy solid/gel | Coformer |
| L-ascorbic acid | Oil; opened for drying | N/A |
| Nicotinamide* | Wet solid/gel | New Pattern |
| Ethyl vanillin | Wet solid/gel | New Pattern (but contaminated with nicotinamide) |
| Sulfacetamide | Oil; opened for drying | N/A |
| Creatine | Gummy solid/gel | Coformer |
| Saccharin | Gummy solid/gel | Amorphous |
| Vanillic acid | Gummy solid/gel | Coformer |
| Methyl salicylate | Gummy solid/gel | Amorphous |
| Blank monoorotate (no coformer) | Gel, unable to take XRPD | N/A |

*Material was further evaluated (see herein below)

Other screens were conducted using heptane as the solvent, as it was determined that the wet and gel-like appearance of the materials may indicate that the attempted nicotine salts are too soluble in nitromethane.

TABLE 6

Co-crystal screen using nicotine fumarate salt in heptane

| Coformer | Observations after milling | XRPD |
|---|---|---|
| L-aspartic acid | Wet solid | Salt and coformer |
| Succinic acid | Wet solid | Poorly crystalline salt and coformer |
| L-pyroglutamic acid | Wet solid | Salt and coformer |
| Hippuric acid | Wet solid | Salt and coformer |
| L-ascorbic acid | Wet solid | Poorly crystalline salt and coformer |
| Nicotinamide | Wet solid | Poorly crystalline salt and coformer |
| Ethyl vanillin | Wet solid | Salt and coformer |
| Sulfacetamide | Wet solid | Coformer |
| Creatine | Wet solid | Salt and coformer |
| Saccharin | Wet solid; deliquesced upon XRPD sample preparation | N/A |
| Vanillic acid | Yellow wet solid | Salt and coformer |
| Methyl salicylate | Wet solid | Salt |
| Blank monoorotate (no coformer) | N/A | N/A |

The screen using nicotine fumarate salt in heptane did not produce any new crystalline material. The XRPD analysis of the blank was thus not carried out.

TABLE 7

Co-crystal screen using nicotine mucate salt in nitromethane

| Coformer | Observations after milling | XRPD |
|---|---|---|
| L-aspartic acid | Wet solid | Salt and coformer |
| Succinic acid | Wet solid | Salt and coformer |
| L-pyroglutamic acid | Gummy solid | Poorly crystalline salt |
| Hippuric acid | Gummy solid | Salt |
| L-ascorbic acid | Wet solid | Salt and coformer |
| Nicotinamide | Wet solid | Salt and coformer |
| Ethyl vanillin | Orange oil; opened for air drying | N/A |
| Sulfacetamide | Wet gummy solid | Salt and coformer |
| Creatine | Wet gummy solid | Salt and coformer |
| Saccharin | Light yellow oil; opened for air drying | N/A |
| Vanillic acid | Wet gummy solid | Salt and coformer |
| Methyl salicylate | Wet solid | Salt |
| Blank monoorotate (no coformer) | Wet solid | Salt |

The screening experiments with nicotine mucate resulted in a number of wet and gummy solids after grinding. The XRPD analyses showed mixtures of the input salt and coformer in most instances.

TABLE 8

Co-crystal screen using nicotine ditartrate salt in nitromethane

| Coformer | Observations after milling | XRPD |
|---|---|---|
| L-aspartic acid | Wet solid | Salt and coformer |
| Succinic acid | Wet solid | Salt and coformer |
| L-pyroglutamic acid | Wet solid | Salt and coformer |
| Hippuric acid | Wet solid | Salt and coformer |
| L-ascorbic acid | Wet solid | Salt and coformer |
| Nicotinamide* | Wet solid | Salt and coformer and one additional peak |
| Ethyl vanillin | Wet solid | Salt and coformer |
| Sulfacetamide | Wet solid | Salt and coformer |
| Creatine | Wet solid | Salt and coformer |
| Saccharin | Wet solid | Salt and coformer |
| Vanillic acid | Yellow wet solid | Salt and coformer |
| Methyl salicylate | Wet solid | Salt |
| Blank monoorotate (no coformer) | Wet solid | Salt |

*Material showed a new peak, but as only one additional peak was observed, no further work on this material was conducted.

The screen with commercially available nicotine ditartrate salt gave solids that showed mixtures of the input materials. In conclusion, three solids showing new XRPD patterns were obtained from the screens above, namely, a material from nicotine L-malate with succinic acid; a material from nicotine monoorotate with succinic acid; and a material from nicotine fumarate with nicotinamide. $^1$H NMR analysis of material obtained from ethyl vanillin and nicotinamide (see Table 5, above) was contaminated with nicotinamide, and no further analysis of this material was conducted.

Certain materials that showed new XRPD patterns were analyzed by $^1$H NMR. It is noted that the material obtained from nicotine monoorotate with succinic acid was not evaluated by NMR, as insufficient material was available. $^1$H NMR analysis of material obtained from nicotine-L-malate salt and succinic acid (see starred entry in Table 2, above) indicated 0.9 equivalents succinic acid and 1.0 equivalent L-malic acid, with no significant residual solvent. $^1$H NMR analysis of material obtained from nicotine fumarate salt and nicotinamide (see starred entry in Table 5, above) indicated 1.0 equivalents nicotinamide and 0.8 equivalents of nitromethane. The $^1$H NMR analyses also confirmed the presence of nicotine, the salt counter ions, and the coformers in both of these salt co-crystals. Studies were conducted to obtain these two salt co-crystals (as well as the material obtained from nicotine fumarate with nicotinamide) in scaled up form, as described in Examples 2-4, below.

Example 2

Preparation and Characterization of (S)-Nicotine L-Malate-(L-Malic Acid-Succinic Acid) Salt Co-Crystal Various methods were attempted to prepare nicotine L-malate-(L-malic acid-succinic acid) salt co-crystals. Crystallization from a single solvent, including ethanol, acetone, methanol, THF, and water was attempted by separately dissolving nicotine L-malate (25 mg) and succinic acid (1 equivalent) in the same solvent at 50° C., mixing the resulting solutions together, and cooling using a ramp from 50 to 5° C. at 0.1° C./min. The only solvent preparation attempted that provided a sufficient amount of solid was a preparation in acetone. Further crystallization methods using nicotine L-malate with succinic acid and L-malic acid (in a ratio of 1:1 for the two acids) rather than using nicotine L-malate with succinic acid only did not show any advantages. Generally, the material prepared from acetone was found to exhibit no evidence of residual input material.

Grinding methods were also pursued, wherein nicotine L-malate and succinic acid or nicotine, L-malic acid, and succinic acid were ground together using stainless steel beads at 650 rpm for two hours. The grinding method produced the desired salt co-crystal of interest only as a mixture containing some or all starting materials. Grinding experiments with altered stoichiometry did not produce any new crystalline forms and did not result in the preparation of the desired salt co-crystal without starting material present.

The material prepared from crystallization in acetone was characterized by XRPD, $^1$H NMR, TGA, DSC, and PLM. The XPRD data indicated a crystalline new structure (consistent with the findings of Example 1) and was clean, with no excess succinic acid indicated. The $^1$H NMR was also consistent with the expected structure, showing ~1.3 equivalents malic acid and 0.5 equivalents of succinic acid. TGA showed no significant weight loss below 110° C. and DSC showed a sharp endotherm onset at 108.0° C. PLM of this sample showed lath-shaped crystals, unsuitable for SCXRD.

Further material was prepared on a larger (1 g) scale as follows. Nicotine L-malate (1 g) was treated with acetone (40 mL, 40 volumes) at 50° C. with stirring. Succinic acid (1 equivalent, 400 mg) was dissolved in acetone (4 mL) at 50° C. and added into the nicotine L-malate suspension (which became thinner upon the addition). The suspension was kept at 50° C. for 1 hour and then a ramp was set up to cool to 5° C. at 0.1° C./minute and the sample was kept at 5° C. overnight, after which a thick suspension was observed. The solid was filtered under suction and washed with acetone (3×20 mL), heptane (10 mL), and dried under vacuum over three days at room temperature (494 mg, 35% yield).

The mother liquors were allowed to evaporate slowly at ambient conditions and lath shaped crystals were obtained, suitable for single crystal x-ray diffraction (SCXRD) data collection. The crystal subjected to SCXRD was determined to have approximate dimensions 0.16×0.15×0.09 mm. See FIGS. 1A and 1B, providing optical micrographs of the batch and the single crystal used for data collection, respectively. The structure of the salt co-crystal was determined at 100K in the triclinic system, space group P1 with the final R1 [I>2σ(I)]=4.47%. A summary of all structural data can be found in Tables 10 and 11 below. The compound was identified as a 2:0.1:0.9 (S)-Nicotine L-malate-(L-malic acid-succinic acid) salt co-crystal as depicted in FIG. 2.

Figure 3:
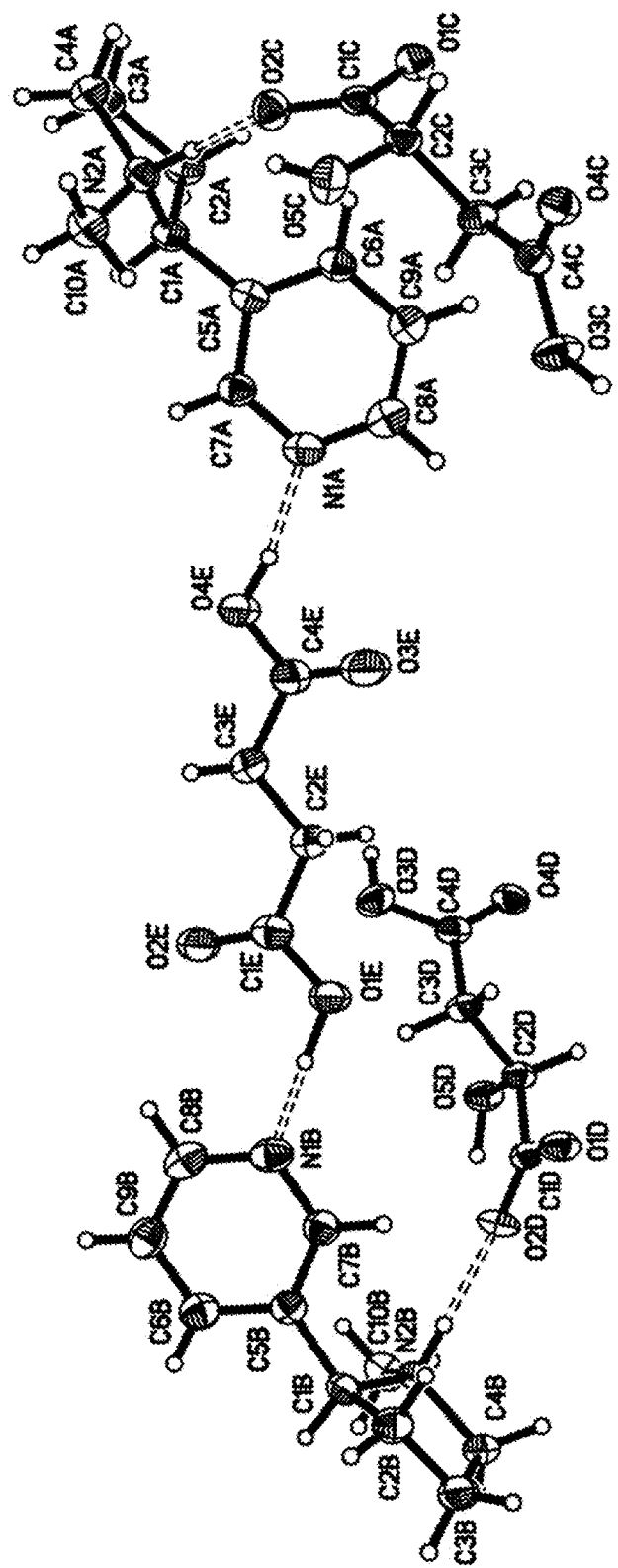
FIG. 3 is a view of the molecules of a (S)-nicotine L-malate-(L-malic acid-succinic acid) salt co-crystal from the crystal structure showing the numbering scheme employed, with minor components of the disorder omitted for clarity.

As shown in FIG. 3, the asymmetric unit of the (S)-nicotine L-malate-(L-malic acid-succinic acid) salt co-crystal contains two fully ordered molecules of nicotinium ions, two molecules of L-malic ions with one of the carboxylic acid groups deprotonated and one molecule with a 0.9 occupancy of neutral succinic and 0.1 occupancy of neutral L-malic acid. The malic acid and succinic acid molecules are believed to function as neutral bridging agents/linkers between nicotine L-malate molecules. Anisotropic atomic displacement ellipsoids for the non-hydrogen atoms are shown at the 50% probability level. Hydrogen atoms are displayed with an arbitrarily small radius. The absolute stereochemistry of the (S)-Nicotine L-malate-(L-malic acid-succinic acid) salt co-crystal was not determined from single crystal X-ray diffraction data using the Flack or Hooft parameters as the Friedel pair coverage was only 80%. However, the stereochemistry for the determined crystal structure was consistent with the naturally occurring (S)-nicotine.

Figure 4:
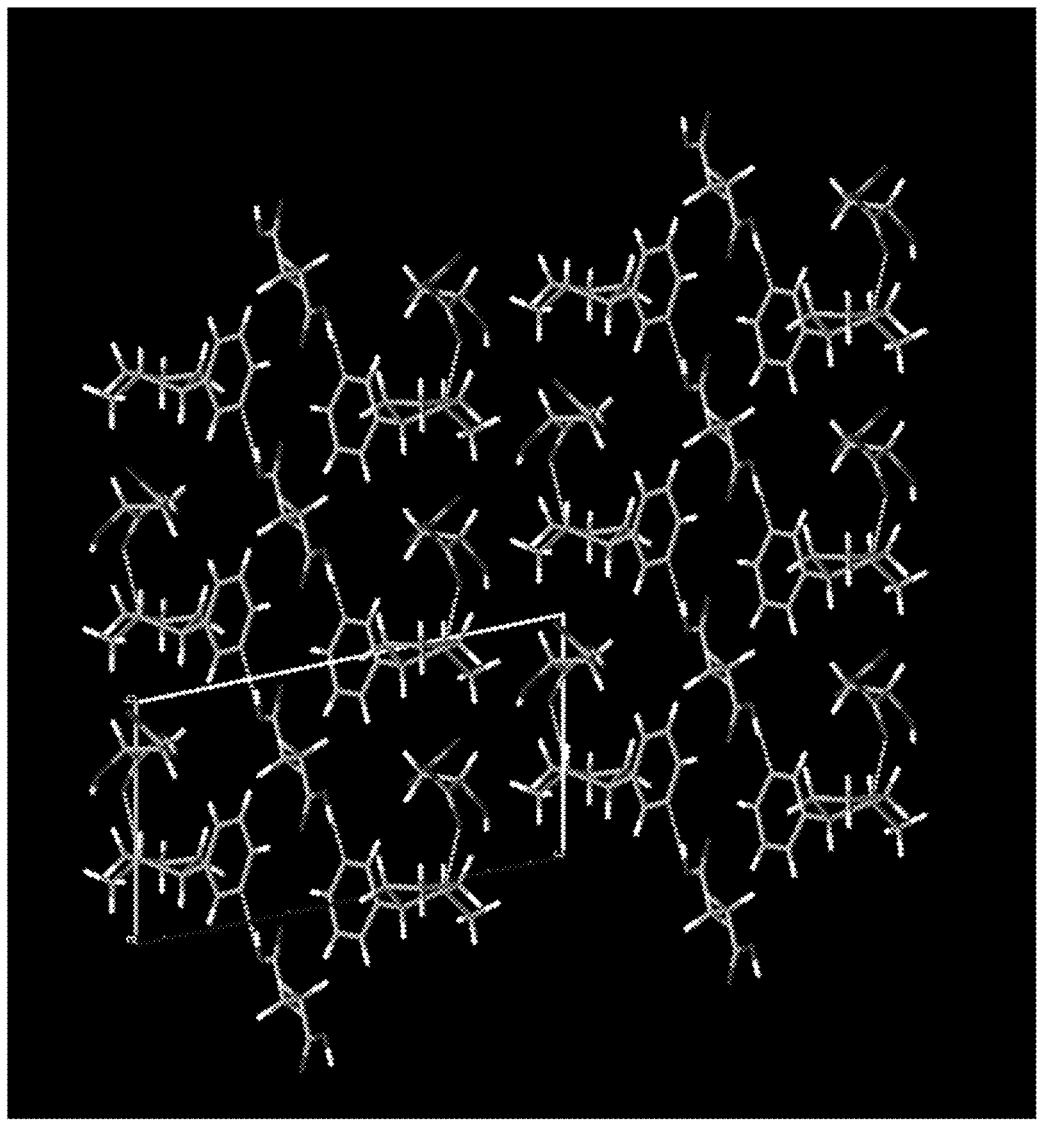
FIG. 4 shows crystal packing of the (S)-nicotine L-malate-(L-malic acid-succinic acid) salt co-crystal looking along the crystallographic a axis, with minor components of the disorder omitted for clarity.
Figure 5:
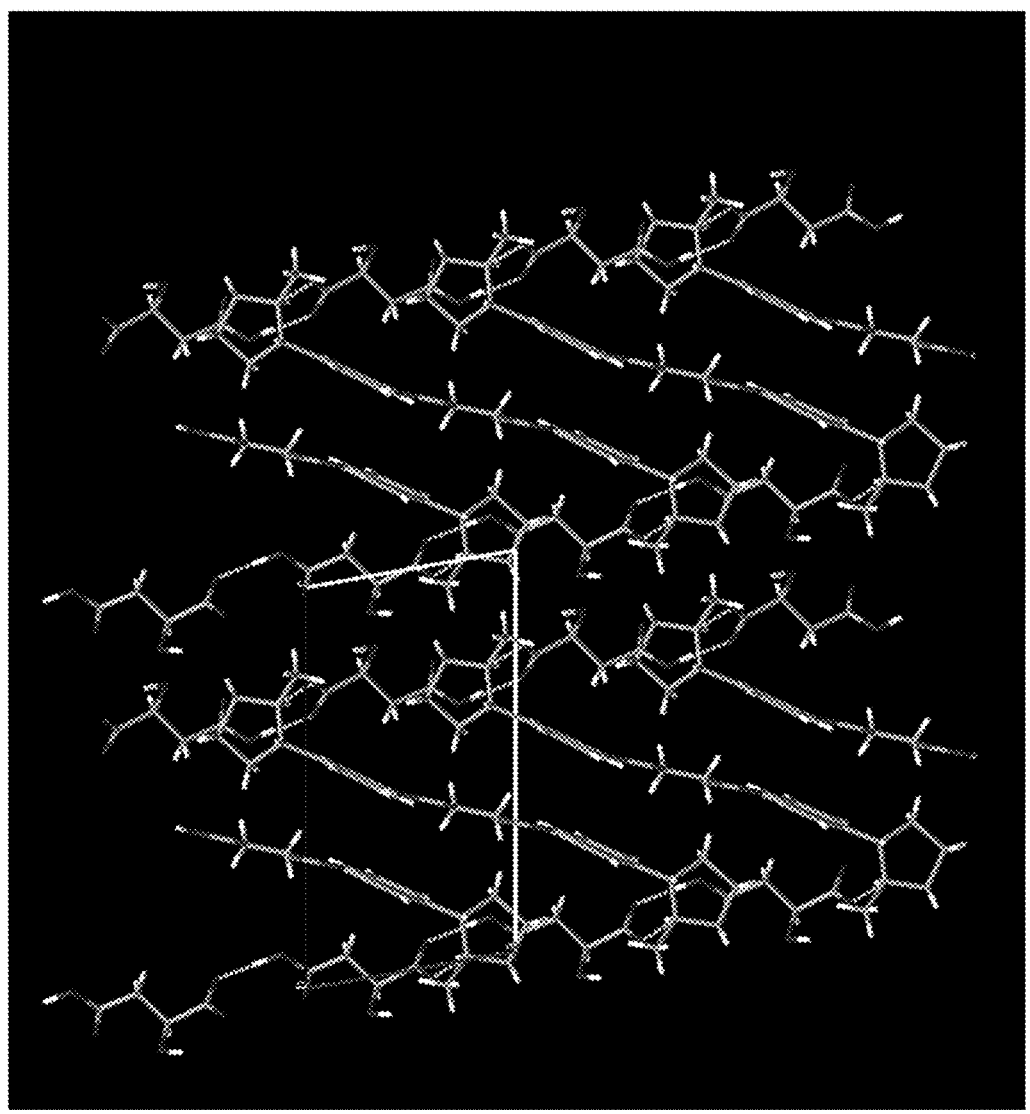
FIG. 5 shows crystal packing of the (S)-nicotine L-malate-(L-malic acid-succinic acid) salt co-crystal looking along the crystallographic b axis with minor components of the disorder omitted for clarity.
Figure 6:
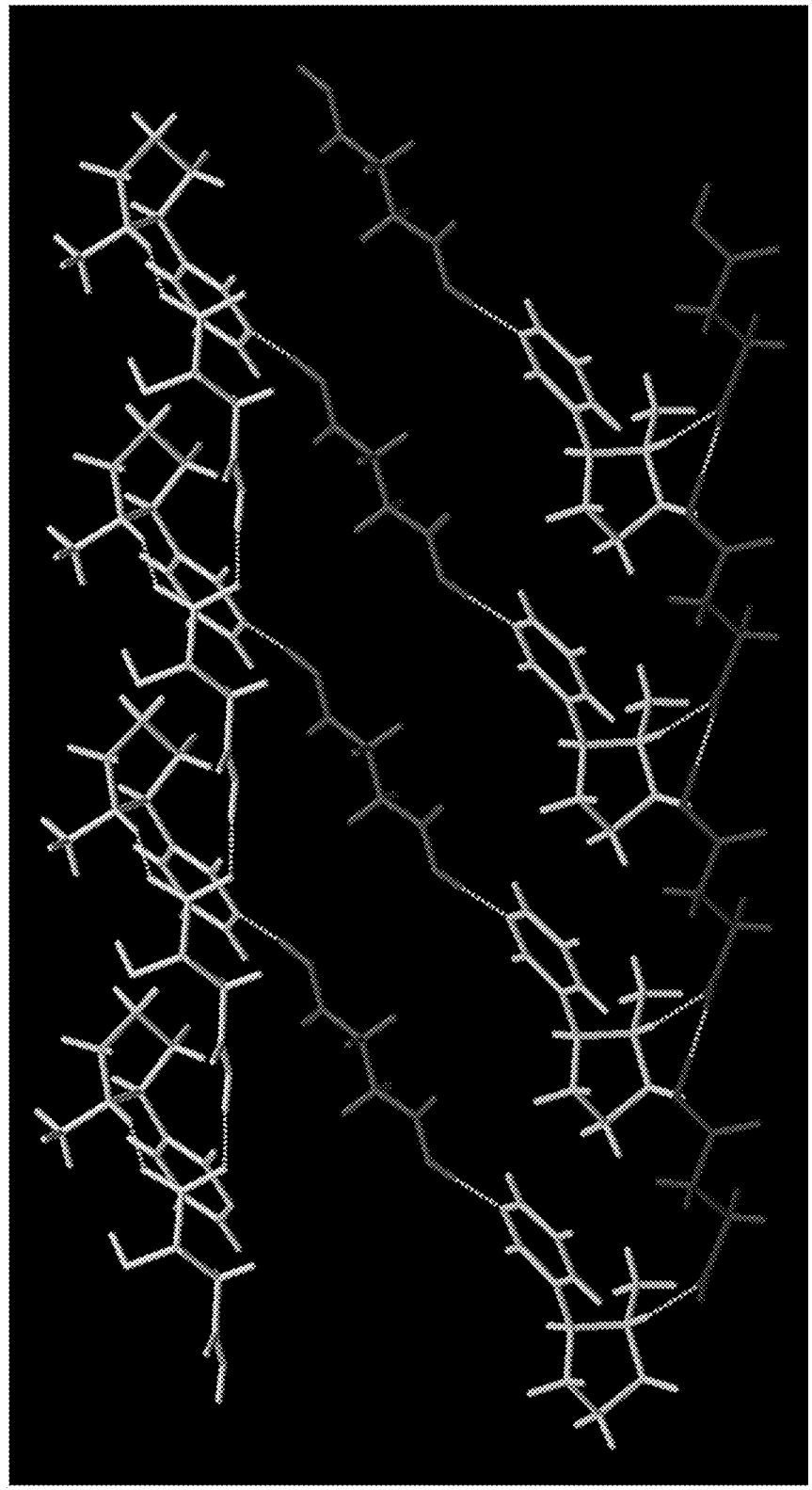
FIG. 6 is an image of the crystal packing of the (S)-nicotine L-malate-(L-malic acid-succinic acid) salt co-crystal showing the main hydrogen bonds between molecules, with partially occupied L-malic acid omitted for clarity.
Figure 7:
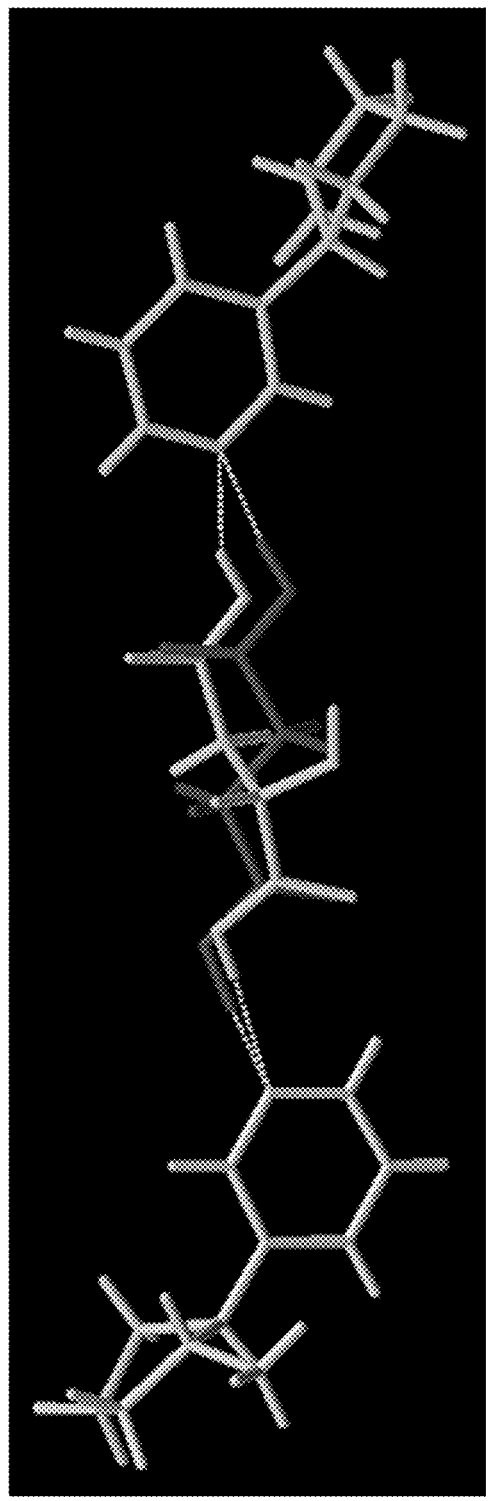
FIG. 7 is a diagram showing two molecules with partial occupation of 0.9 (succinic acid) and 0.1 (L-malic acid)

A view of the packing within the unit cell can be seen in FIGS. 4, 5, and 6. The inter-molecular hydrogen bonds are shown as dashed lines. There are 9 inter-molecular hydrogen-bonding interactions in the structure resulting in a complex hydrogen bonded network. Details of these hydrogen bonds are provided in Table 9, below.

TABLE 9

Hydrogen bonding interactions (Å and °).

| D-H...A | d(D-H) | d(H . . . A) | d(D . . . A) | <(DHA) |
|---|---|---|---|---|
| N2A-H2A . . . O2C#1 | 0.88(5) | 1.86(5) | 2.684(4) | 157(4) |
| N2B-H2B . . . O2D#2 | 0.91(5) | 1.83(5) | 2.695(4) | 158(4) |
| O3C-H3C . . . O1C#3 | 1.06(8) | 1.48(8) | 2.536(4) | 177(6) |
| O5C-H5C . . . O4D#4 | 0.87(6) | 2.62(6) | 3.334(4) | 140(5) |
| O3D-H3D . . . O1D#2 | 0.95(7) | 1.58(8) | 2.530(4) | 173(6) |
| O1E-H1E . . . N1B | 1.09(6) | 1.55(6) | 2.642(5) | 174(5) |
| O4E-H4E . . . N1A#5 | 0.93(6) | 1.72(6) | 2.637(4) | 168(6) |
| O1F-H1F . . . N1B | 0.84 | 2.05 | 2.87(5) | 167.9 |
| O4F-H4F . . . N1A#5 | 0.84 | 1.94 | 2.72(3) | 154.2 |

1x, y + 1, z − 1
2x + 1, y, z
3x − 1, y, z
4x, y − 1, z
5x + 2, y + 1, z

Figure 8:
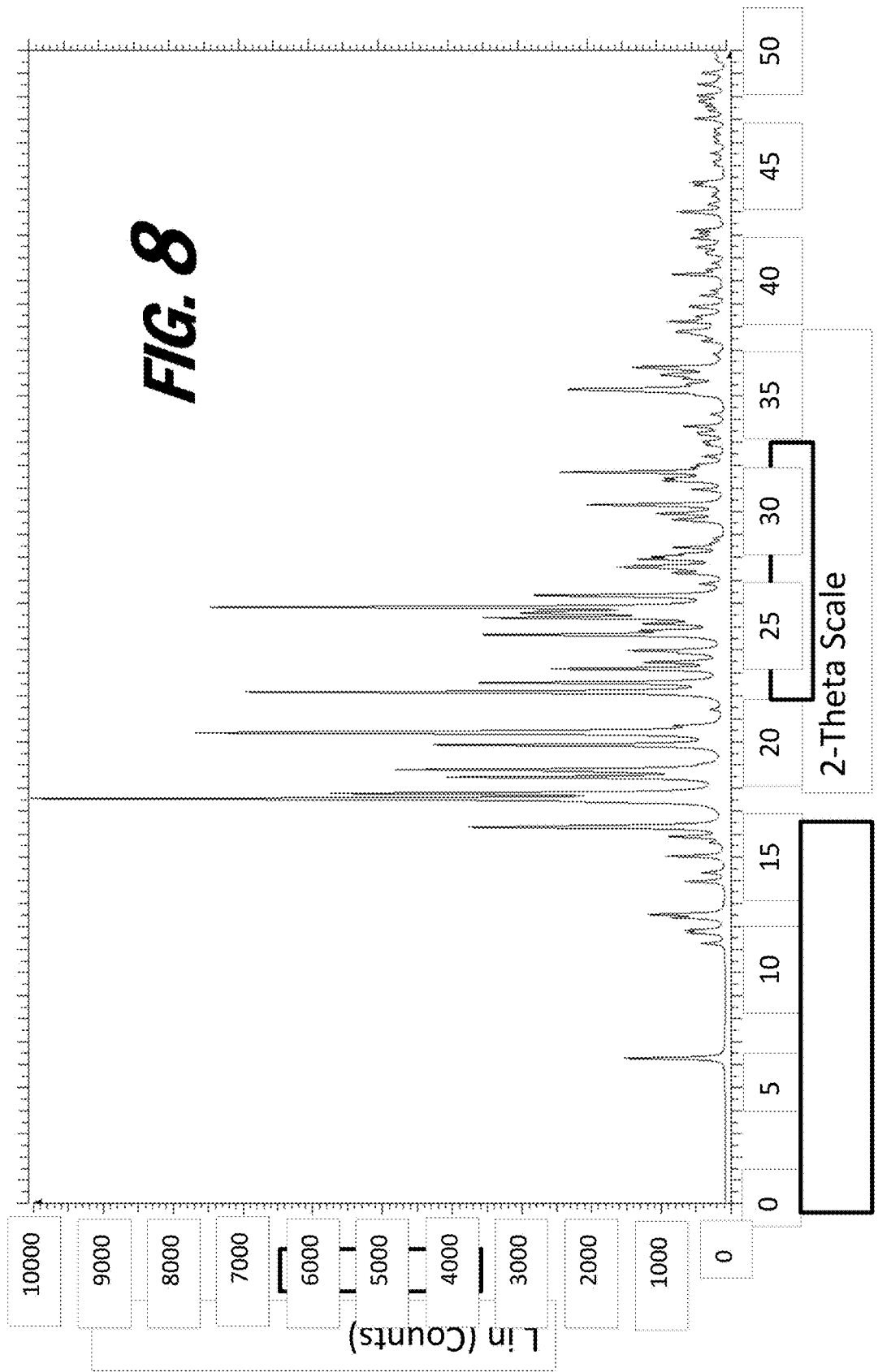
FIG. 8 is a simulated XRPD pattern of a (S)-nicotine L-malate-(L-malic acid-succinic acid) salt co-crystal.
Figure 9:
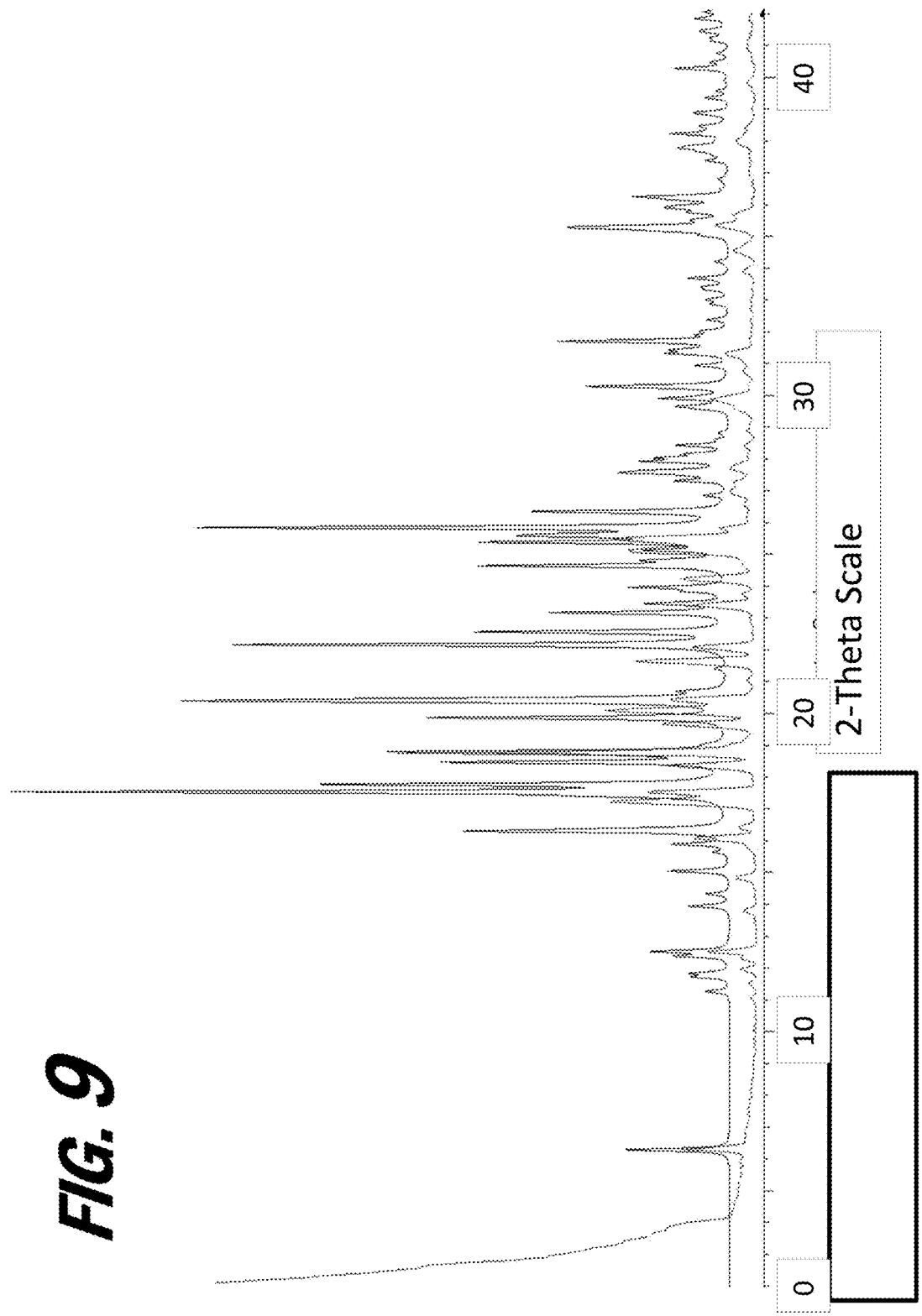
FIG. 9 is an overlay of the simulated (upper) and experimental (lower) XRPD diffractograms of a nicotine L-malate-(L-malic acid-succinic acid) salt co-crystal.

There are no other unusual structural features, and the final Fourier difference map is featureless, showing maximal and minimal electron densities of 0.256 and −0.219 eÅ$^{-3}$, respectively. The simulated XRPD pattern for the (S)-Nicotine L-malate-(L-malic acid-succinic acid) salt co-crystal at 100 K is shown in FIG. 8. An overlay with the experimental diffractogram at RT (FIG. 9) shows that the single crystal is mostly consistent with the bulk crystals obtained. Slight differences are attributable to lattice variations with temperature and preferred orientation. Sample details and crystal data for the analyzed crystal are provided below in Table 10 and data collection and structure refinement data are provided in Table 11. Table 12 provides a refinement summary, and Table 13 provides details on site occupancy factors that deviate from unity.

TABLE 10

Sample details and crystal data

| Compound | 2:2:0.1:0.9 (S)-Nicotine L-malate-(L-malic acid-succinic acid) salt co-crystal |
|---|---|

TABLE 10-continued

Sample details and crystal data

| | |
|---|---|
| Crystallization solvents | Acetone |
| Crystallization method | Slow evaporation |
| Empirical formula sum | $C_{32}H_{46}N_4O_{14.10}$ |
| Empirical formula extended | $(C_{10}H_{15}N_2)_2 (C_4H_5O_5)_2 (C_4H_6O_5)_{0.1}$ $(C_4H_6O_4)_{0.9}$ |
| Formula weight | 712.33 |
| Temperature | 100(2) K |
| Wavelength | 1.54178 Å |
| Crystal size | 0.160 × 0.150 × 0.090 mm |
| Crystal habit | Colorless prism |
| Crystal system | Triclinic |
| Space group | P1 |
| Unit cell dimensions | a = 7.6165(3) Å    α = 78.164(4)° |
| | b = 8.0468(3) Å    β = 79.694(4)° |
| | c = 14.6995(6) Å   γ = 88.146(3)° |
| Volume | 867.52(6) Å$^3$ |
| Z | 1 |
| Density (calculated) | 1.363 Mg/m$^3$ |
| Absorption coefficient | 0.909 mm$^{-1}$ |
| F(000) | 379 |

TABLE 11

Data collection and structure refinement

| | |
|---|---|
| Diffractometer | SuperNova, Dual, Cu at zero, Atlas |
| Radiation source | SuperNova (Cu) X-ray Source, CuKα |
| Data collection method | Omega scans |
| Theta range for data collection | 3.120 to 76.228° |
| Index ranges | $-9 \leq h \leq 8, -10 \leq k \leq 10, -18 \leq l \leq 18$ |
| Reflections collected | 32580 |
| Independent reflections | 6514 [R(int) = 0.0515] |
| Coverage of independent reflections | 100.0% |
| Variation in check reflections | N/A |
| Absorption correction | Semi-empirical from equivalents |
| Max. and min. transmission | 1.00000 and 0.47886 |
| Structure solution technique | Direct methods |
| Structure solution program | SHELXTL (Sheldrick, 2013) |
| Refinement technique | Full-matrix least-squares on F$^2$ |
| Refinement program | SHELXTL (Sheldrick, 2013) |
| Function minimized | $\Sigma w(Fo^2 - Fc^2)^2$ |
| Data/restraints/parameters | 6514/21/519 |
| Goodness-of-fit on F$^2$ | 1.048 |
| $\Delta/\sigma_{max}$ | 0.000 |
| Final R    5704 data; I > 2σ(I) | R1 = 0.0447, wR2 = 0.1054 |
| indices    all data | R1 = 0.0550, wR2 = 0.1147 |
| Weighting scheme | $w = 1/[\sigma^2 (Fo^2) + (0.0546P)^2 + 0.2965P]$ where $P = (Fo^2 + 2Fc^2)/3$ |
| Absolute structure parameter | −0.01(13) |
| Extinction coefficient | n/a |
| Largest diff. peak and hole | 0.256 and −0.219 eÅ$^{-3}$ |

TABLE 12

Refinement summary:

| | |
|---|---|
| Ordered Non-H atoms, XYZ | Freely refining |
| Ordered Non-H atoms, U | Anisotropic |
| H atoms (on carbon), XYZ | Idealized positions riding on attached atoms |
| H atoms (on carbon), U | Appropriate multiple of U(eq) for bonded atomH |
| H atoms (on heteroatoms), XYZ | Freely refining when possible, otherwise appropriate HFIX used |
| H atoms (on heteroatoms), U | Isotropic when possible, otherwise multiple of U(eq) for bonded atom |
| Disordered atoms, OCC | A succinic and a L-malic acid molecule occupy the same position with final refined occupancies of 0.9 and 0.1 respectively |
| Disordered atoms, XYZ | Freely refining when possible, otherwise appropriate SAME instruction used |
| Disordered atoms, U | Isotropic when possible, otherwise appropriate EADP used |

TABLE 13

Site occupancy factors that deviate from unity

| Atom | sof |
|---|---|
| C4D | 1 |
| O2E | 0.909(4) |
| H4E | 0.909(4) |
| H2EA | 0.909(4) |
| H3EA | 0.909(4) |
| O1F | 0.091(4) |
| O3F | 0.091(4) |
| O5F | 0.091(4) |
| C2F | 0.091(4) |
| H3FA | 0.091(4) |
| O1E | 0.909(4) |
| O3E | 0.909(4) |
| C1E | 0.909(4) |
| H2EB | 0.909(4) |
| H3EB | 0.909(4) |
| H1F | 0.091(4) |
| O4F | 0.091(4) |
| H5FA | 0.091(4) |
| H2FA | 0.091(4) |
| H3FB | 0.091(4) |
| H1E | 0.909(4) |
| O4E | 0.909(4) |
| C2E | 0.909(4) |
| C3E | 0.909(4) |
| C4E | 0.909(4) |
| O2F | 0.091(4) |
| H4F | 0.091(4) |
| C1F | 0.091(4) |
| C3F | 0.091(4) |
| C4F | 0.091(4) |

Analysis of the scaled up material indicated a crystalline new pattern by XRPD, which was consistent with that of the material prepared on a smaller scale (as found in Example 1). XRPD peaks for the scaled-up sample are provided below in Table 14. Table 14: Characteristic XRPD pattern peaks of nicotine L-malate-(L-malic acid-succinic acid) salt co-crystal

| Angle (2-Theta °) | Relative Intensity (%) |
|---|---|
| 6.2 | 22 |
| 11.9 | 7 |
| 12.5 | 16 |
| 13.7 | 7 |
| 14.7 | 8 |

-continued

| Angle (2-Theta °) | Relative Intensity (%) |
|---|---|
| 16.0 | 19 |
| 16.4 | 8 |
| 29.8 | 14 |
| 17.1 | 39 |
| 17.5 | 29 |
| 18.3 | 25 |
| 18.7 | 100 |
| 19.6 | 26 |
| 20.0 | 40 |
| 20.4 | 24 |
| 21.6 | 33 |
| 22.0 | 19 |
| 23.3 | 19 |
| 24.2 | 22 |
| 25.1 | 35 |
| 25.4 | 38 |
| 29.8 | 14 |

Figure 10:
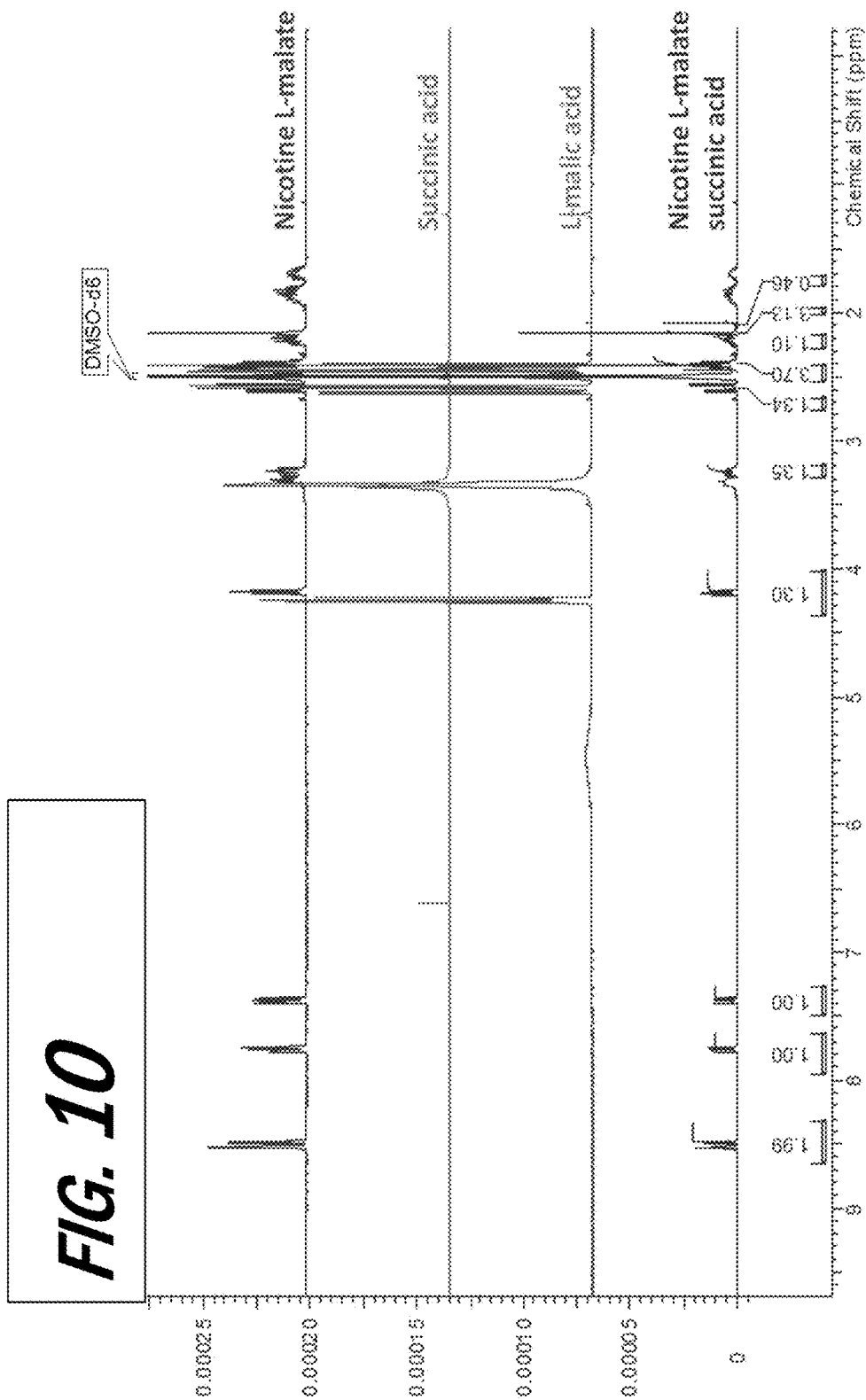
FIG. 10 is a $^1$H-NMR spectrum of a nicotine L-malate-(L-malic acid-succinic acid) salt co-crystal compared to input materials FIG. 11 provides TGA and DSC analyses of a nicotine L-malate-(L-malic acid-succinic acid) salt co-crystal.
Figure 11:
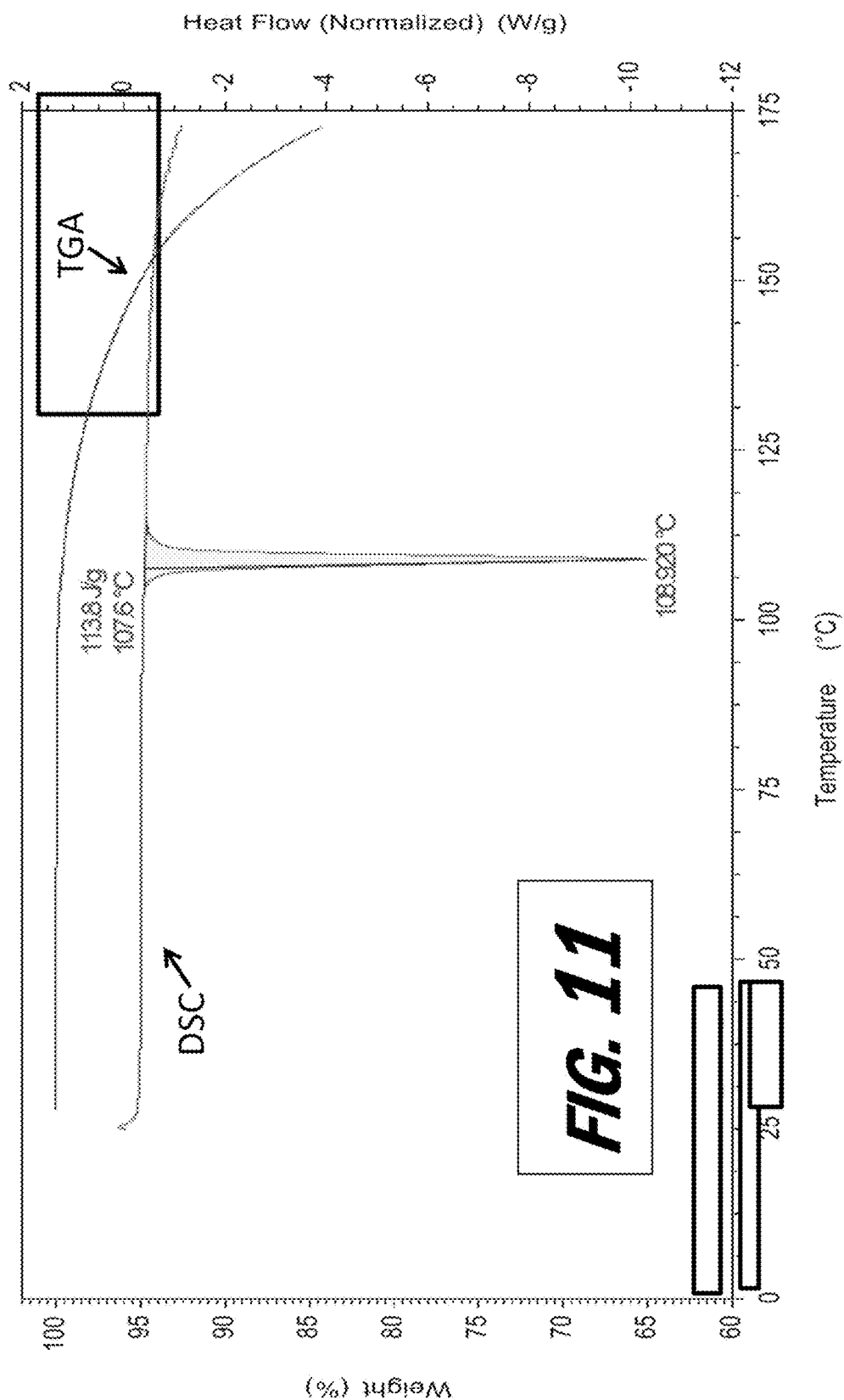
Figure 12A:
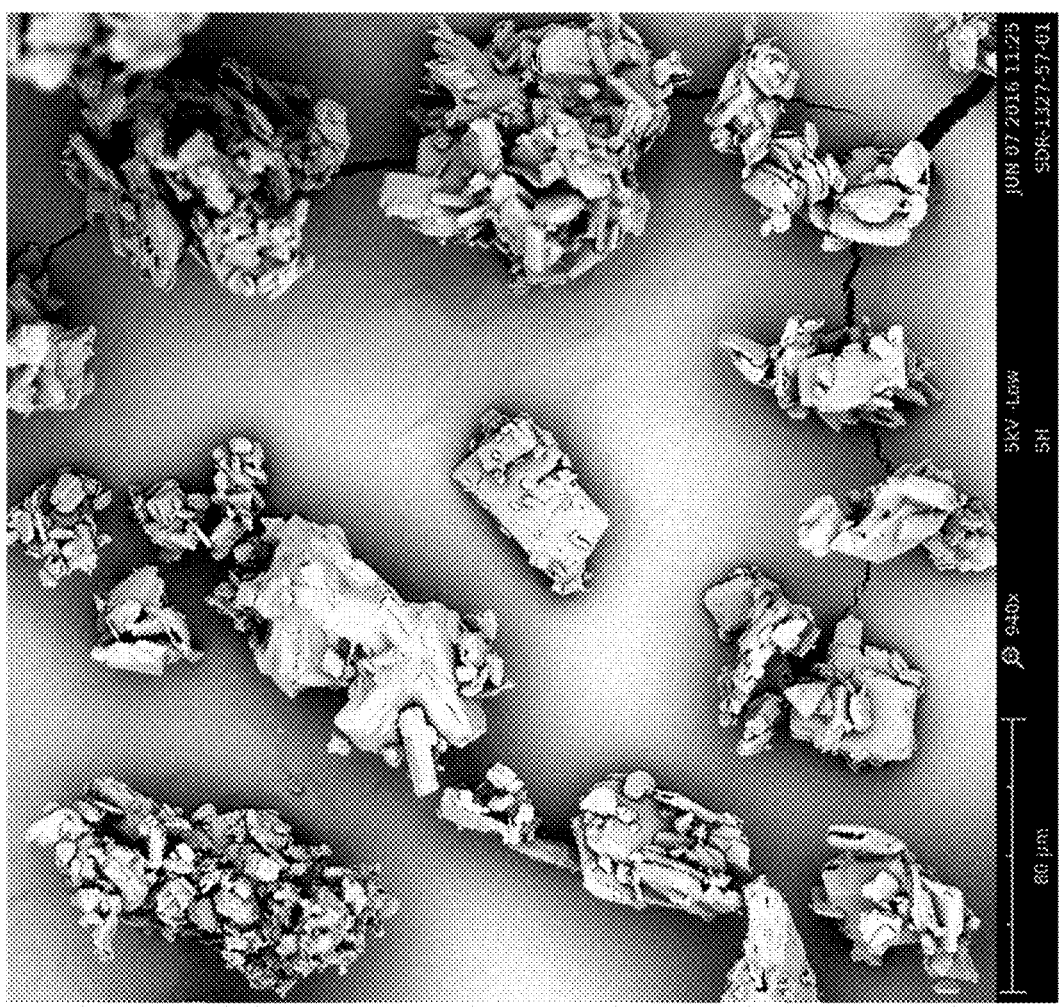
FIGS. 12A and 12B are SEM images of a nicotine L-malate-(L-malic acid-succinic acid) salt co-crystal at different magnifications.
Figure 12B:
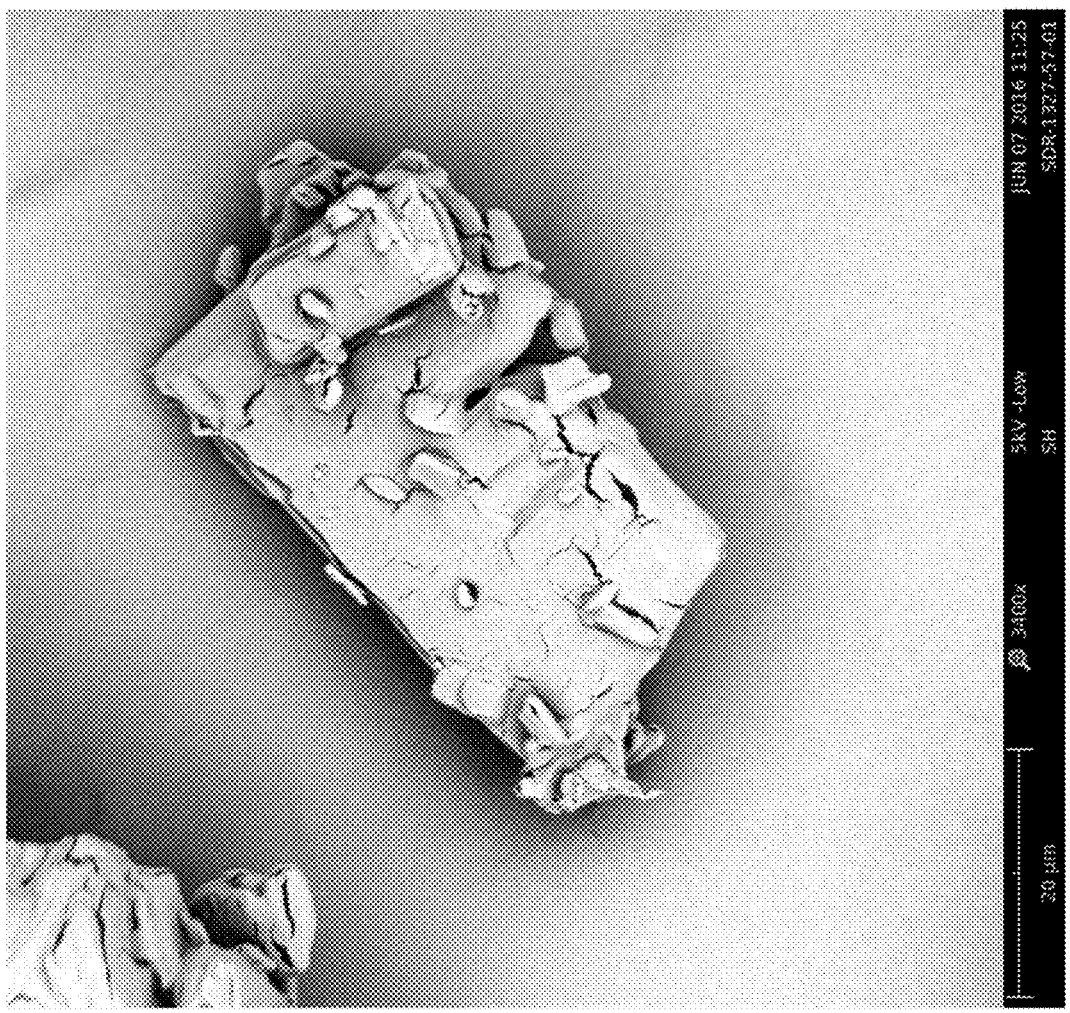

$^1$H NMR analysis of this scaled-up sample is shown in FIG. 10. TGA and DSC analyses are provided in FIG. 11. The melting endotherm in the DSC has an onset at 107.6° C. The material was not stable at elevated humidity conditions, showing deliquescence after 5 days. High hygroscopicity was highlighted from the GVS experiment, also showing deliquescence, quantified as a 67% w/w moisture uptake between 0-90% RH. The aqueous solubility of the material is >200 mg/mL. SEM images of the material are provided in FIGS. 12A and 12B (showing lath-shaped crystals of sizes between 5 to 50 μm long, mainly in the form of agglomerates (up to 100 μm long).

A similar preparation was done on a 10 g scale, giving the nicotine L-malate-(L-malic acid-succinic acid) salt co-crystal in 57% yield (8.0 g). Analysis of the scaled up material indicated a crystalline new pattern by XRPD, which was consistent with that of the material prepared on a smaller scale. $^1$H NMR analysis was also consistent with that of the material prepared on a smaller scale. The melting endotherm in the DSC has an onset at 107.1° C.

Elemental CHN analysis was carried out for both scaled up materials, with theoretical values calculated for salt co-crystals with varying stoichiometries. The best fit corresponded to the calculations with 2:0.1:0.9 nicotine L-malate salt: L-malic acid: succinic acid, as shown in Table 15.

TABLE 15

Elemental CHN analysis of nicotine L-malate-(L-malic acid-succinic acid) salt co-crystal

| ELEMENT | C | H | N |
|---|---|---|---|
| Theoretical Based on various nicotine L-malate: L-malic acid: succinic acid stoichiometries | | | |
| 2:0:1 | 51.08 | 6.52 | 7.88 |
| 2:0.1:0.9 (per crystal structure) | 53.96 | 6.50 | 7.87 |
| 2:0.5:0.5 | 53.51 | 6.39 | 7.80 |
| 2:1:1 | 51.24 | 6.09 | 6.64 |
| Experimental | | | |
| 1 g scale material run 1 | 53.76 | 6.61 | 7.81 |
| 1 g scale material run 2 | 53.74 | 6.62 | 7.77 |
| 10 g scale material run 1 | 53.73 | 6.42 | 7.81 |
| 10 g scale material run 2 | 53.72 | 6.43 | 7.80 |

The data in sum showed that the nicotine L-malate-(L-malic acid-succinic acid) salt co-crystal could be prepared reproducibly on a scale up to 10 grams. Characterization showed this to be an anhydrous form with a ratio of 2:0.1:0.9 nicotine L-malate salt:L-malic acid:succinic acid. The material was found to be highly hygroscopic and melts around 107° C.

Example 3

Preparation and Characterization of Nicotine Fumarate Nicotinamide Salt Co-Crystal Various methods were attempted to prepare nicotine fumarate nicotinamide salt co-crystals. Crystallization from nitromethane was attempted by weighing 50 mg of nicotine fumarate into a vial, adding 1 equivalent of nicotinamide, adding the solvent in portions, up to a maximum of 50 volumes, and heating the resulting mixture to 50° C. The mixture was then cooled using a ramp from 50° C. to 5° C. at 0.1° C./min. When 30 μL of nitromethane was used as the solvent, a wet solid was produced and found to exhibit the noted XRPD pattern (see Example 1).

Grinding methods were also pursued, wherein nicotine fumarate and nicotinamide were ground together using stainless steel beads at 650 rpm for two hours. The grinding method produced the desired salt co-crystal of interest only as a mixture containing some or all starting materials. Attempts using 50 mg of nicotinamide and 10 μL nitromethane gave an agglomerated solid, exhibiting the noted XRPD pattern consistent with Example 1 (one trial giving some evidence of residual input material and the other trial giving a sample with no evidence of residual input material). Grinding experiments with altered stoichiometry (double the nitromethane) did not demonstrate any significant benefit in obtaining the desired XPRD pattern.

Crystallization from a single solvent, including acetone, THF, acetonitrile, methyl ethyl ketone, nitromethane, ethanol, isopropyl alcohol, 1,4-dioxane, water, and methanol was attempted by separately dissolving nicotine fumarate (50 mg) and nicotinamide (1 equivalent) in the same solvent at 50° C., mixing the resulting solutions together, and cooling using a ramp from 50 to 5° C. at 0.1° C./min. The only solvent that provided a sufficient amount of solid was acetone, producing a small amount of material. Crystallization from acetonitrile, methyl ethyl ketone, and nitromethane resulted in crystalline solids with new patterns (distinguishable from that found in Example 1); however, no further characterization of these materials was conducted due to limited amounts of material.

Further material was attempted to be prepared on a larger (1 g) scale. An attempt to prepare material from an acetone solution on a larger scale (based on the screening method outlined above) was unsuccessful (resulting in a crystalline material, but indicating by $^1$H NMR that no nicotine was present, believed to be a nicotinamide:fumaric acid co-crystal). Further attempts to prepare material from an acetone solution on a larger scale (based on the screening method outlined above) initially led to solid material exhibiting the noted XRPD pattern (when material was extracted while the mixture was at 50° C.); however, after cooling the reaction mixture, additional XRPD peaks were noted, which were not previously identified, and no more work was carried out on these samples. Finally, attempts to prepare material by grinding on a larger scale (based on the screening method outlined above) led to a material that was determined, by XRPD, to be a mixture of the nicotine fumarate nicotinamide salt co-crystals and unreacted nicotine fumarate. No more work was carried out on this sample either. These examples highlight that preparation procedures for this material were not reproducible during scale-up.

Given that the scale-up experiments were not successful, further characterization of the nicotine fumarate nicotinamide salt co-crystals was conducted using a batch containing a small amount of nicotine fumarate (prepared from the small-scale grinding experiments). This material was characterized by XRPD, $^1$H NMR, TGA, DSC, and GVS. The XPRD showed a crystalline new structure (with a small amount of nicotine fumarate, as expected). The $^1$H NMR was consistent with the expected structure, showing about 1.3 equivalents fumaric acid and about 1.3 equivalents nicotinamide. TGA showed slight weight loss of 0.4% below 65° C. and DSC showed a broad endotherm between 25° C. and 60° C. (8.5 J/g), followed by a larger broad endotherm with onset at 72.7° C. (46.8 J/g) and decomposition above 125° C. The material was found to be deliquescent after 3 days under storage at 40° C./75% RH and after 3 days under storage at 25° C./97% RH. GVS showed 57% w/w moisture uptake between 0-90% RH and the material deliquesced during the experiment. It was determined that this material is highly hygroscopic and deliquesces at elevated temperature/humidity and after the GVS experiment. The material generally has low thermal stability.

Example 4

Preparation and Characterization of Nicotine Monoorotate Succinic Acid Salt Co-Crystal Various methods were attempted to prepare nicotine monoorotate succinic acid salt co-crystals. Crystallization from a single solvent, including ethanol, acetone, methanol, THF, and water was attempted by separately dissolving nicotine monoorotate (50 mg) and succinic acid (1 equivalent) in the same solvent at 50° C., mixing the resulting solutions together, and cooling using a ramp from 50 to 5° C. at 0.1° C./min. Solid was produced in experiments using all solvents. However, XRPD indicated that the solids produced in ethanol, acetone, and methanol were nicotine diorotate. The referenced pattern from the screening experiments outlined above in Example 1 was observed only from cooling in THF and only a small amount of material was afforded.

Further attempts to prepare this salt co-crystal on a larger (0.5 g) scale were pursued as follows. Nicotine mono or diorotate (400 mg) was treated with THF (15 or 30 volumes) at 50° C. with stirring. Succinic acid (1 equivalent) was dissolved in THF (15 or 30 volumes) at 50° C. and added into the nicotine orotate solutions. The solutions were kept at 50° C. for 1 hour and then a ramp was set up to cool to 5° C. at 0.1° C./minute and aliquots were removed from the resulting suspensions for XRPD analysis. Analysis of each attempted preparation indicated that the solid was nicotine diorotate. No evidence of the desired salt co-crystal was observed and no further work was carried out on these samples.

Figure 13:
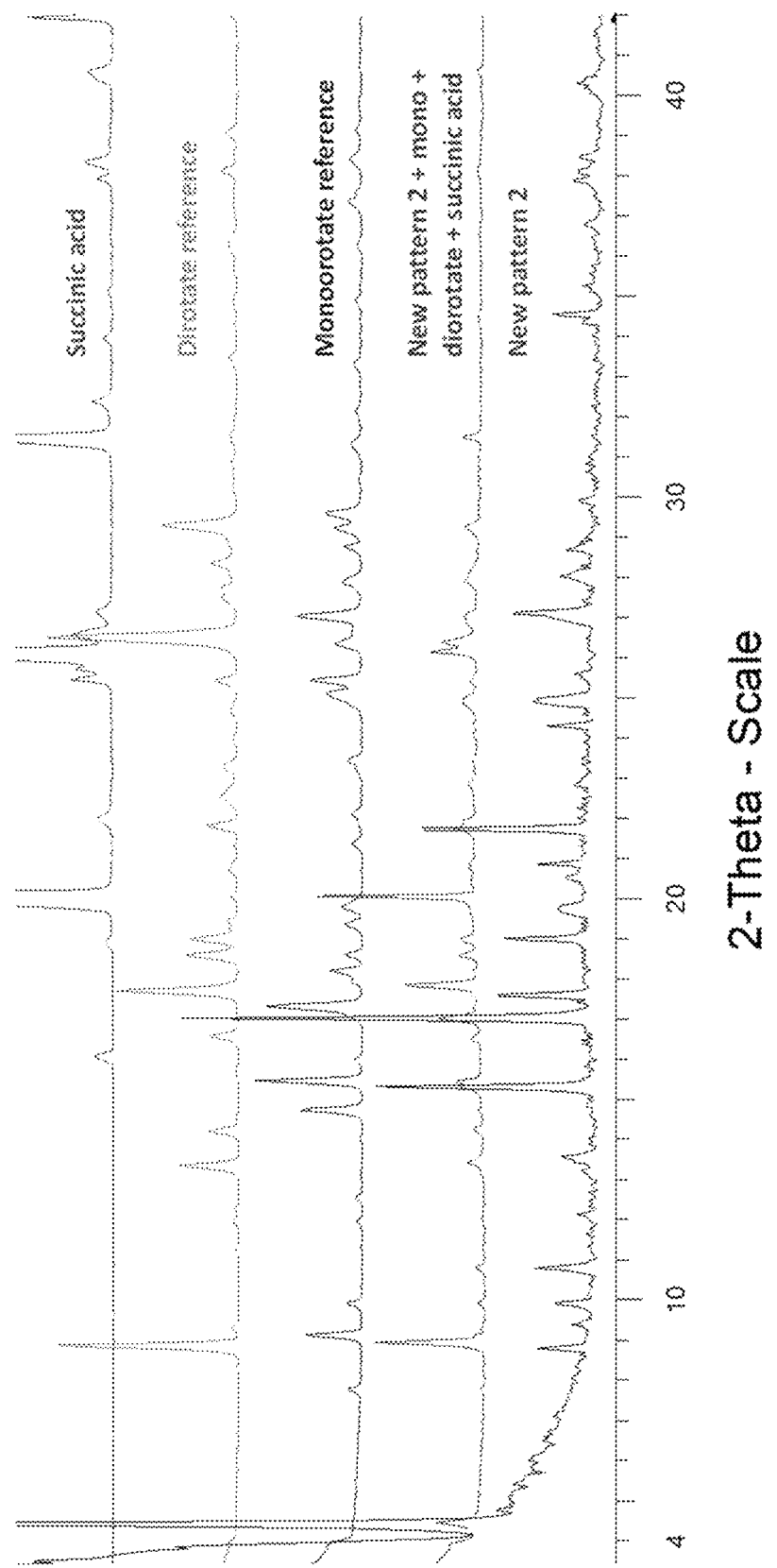
FIG. 13 is an XRPD pattern overlay of a nicotine monoorotate succinic acid co-crystal sample (referred to in the Figure as "New pattern 2") compared with reference input materials.

Given that the scale-up experiments were not successful, further characterization of the nicotine monoorotate succinic acid salt co-crystals was conducted using a batch prepared from the small-scale THF solution preparation experiment. This material was characterized by XRPD and 1H NMR. The XRPD indicated a crystalline material, with a pattern consistent with that identified in Example 1. FIG. 13 is an XRPD pattern overlay of the nicotine monoorotate succinic acid salt co-crystal sample (referred to in the Figure as "New pattern 2") compared with reference input materials. Characteristic peaks are shown below in Table 16.

TABLE 16

Characteristic XRPD pattern peaks of nicotine monoorotate succinic acid salt co-crystal sample

| Angle (2-Theta °) | Relative Intensity (%) |
|---|---|
| 4.4 | 100 |
| 8.7 | 10 |
| 9.9 | 8 |
| 10.8 | 10 |
| 15.3 | 28 |
| 17.0 | 50 |
| 17.6 | 14 |
| 19.0 | 15 |
| 20.9 | 10 |
| 21.7 | 23 |
| 24.3 | 9 |
| 24.9 | 10 |
| 27.1 | 13 |

$^1$H NMR analysis was consistent with the structure and indicated 1.0 equivalents orotic acid and 1.0 equivalents succinic acid. Further characterization was not possible due to the small amount of recovered material.

Example 5

Preparation and Characterization of Nicotine Mucate Salt

As noted above in Example 1, attempts to prepare nicotine mucate led to a form of nicotine mucate that was determined by XRPD to be different than that described in the Experimental section of US Pat. App. Publ. No. 2015/0344456, which is incorporated herein by reference in its entirety. As such, more comprehensive characterization of this salt form (prepared as described above in Example 1) was carried out, as described herein.

Figure 14:
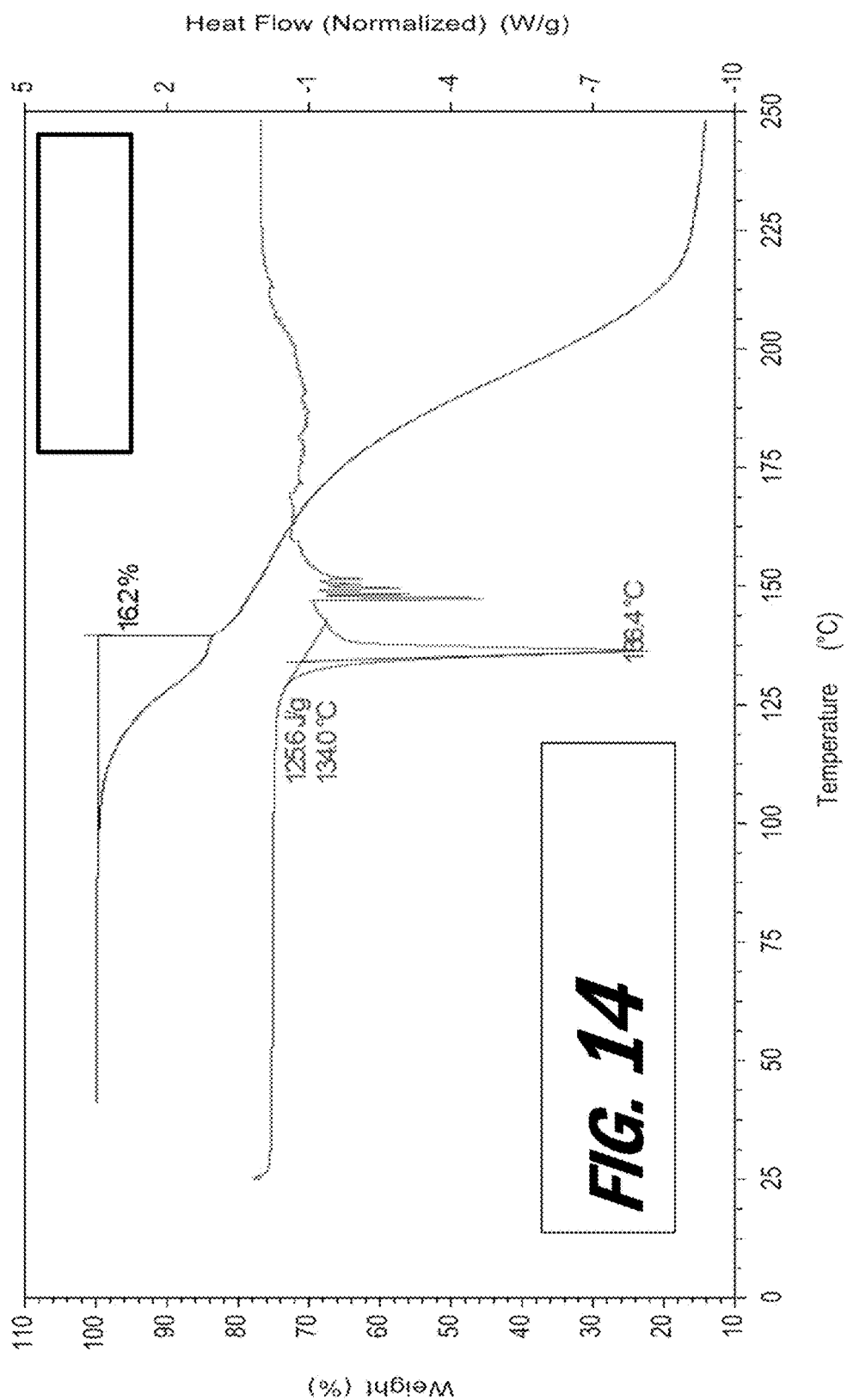
FIG. 14 provides TGA and DSC analyses of a nicotine mucate salt.
Figure 15:
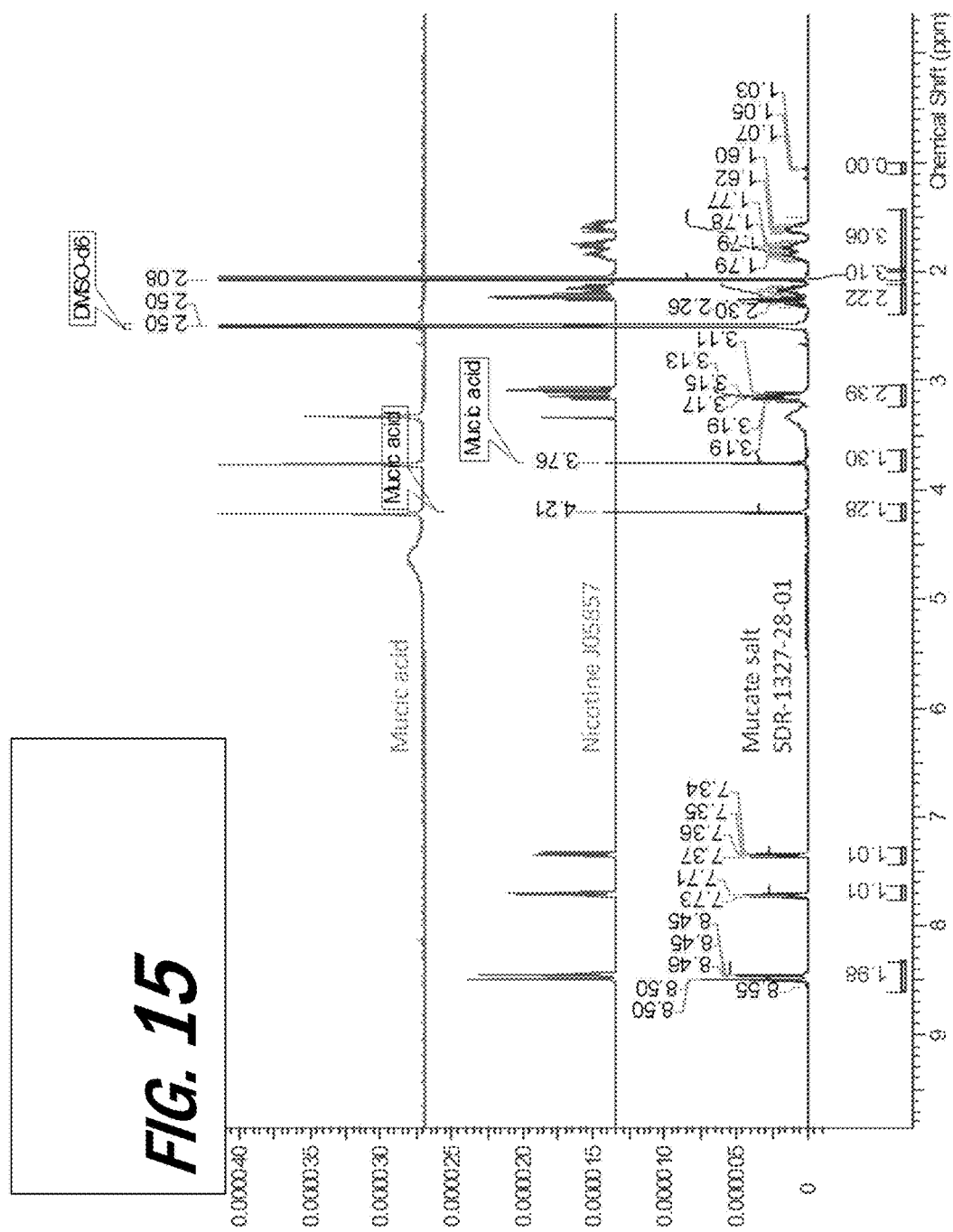
FIG. 15 is a $^1$H-NMR spectrum of a nicotine mucate salt form compared to input materials.

A salt of nicotine with mucic acid was prepared from ethanol as a white crystalline powder in ~84% yield. The solid was analyzed by differential scanning calorimetry (DSC), which showed a sharp endotherm at 125.6° C., followed by decomposition (with no significant weight loss below 100° C. as shown by thermogravimetric analysis (TGA), as shown in FIG. 14). The salt was found to be water soluble in 10 volumes at 50° C., with a solubility of greater than 100 mg/mL at 50° C. Elemental analysis results were a best fit with (S)-nicotine: mucic acid stoichiometry of 1.0: 0.6 nicotine: mucic acid (distinguishable from the stoichiometry reported in US Pat. App. Publ. No. 2015/0344456 of 1.0:0.7 nicotine: mucic acid). The stoichiometry of the salt was also confirmed by $^1$H NMR spectroscopy, as shown in FIG. 15, also providing comparative spectra for input materials. The water content was determined to be 0.3% by Karl Fisher titration, and the salt was found to be slightly hygroscopic, deliquescing after 6 days at 25° C./97% RH and 40° C./75% RH. Elemental C, H, and N analysis was conducted on the mucic acid salt form prepared according to this Example, and the results are provided in the following table.

TABLE 17

Elemental CHN analysis on new nicotine mucate salt form

| ELEMENT | C | H | N |
|---|---|---|---|
| Theoretical | | | |
| 0.5 eq. mucic acid | 58.41 | 7.16 | 10.48 |
| 0.6 eq. mucic acid (as per $^1$H NMR) | 56.70 | 6.93 | 9.72 |
| 0.1 eq. mucic acid | 51.75 | 6.24 | 7.54 |
| Experimental | | | |
| Run 1 | 56.26 | 7.18 | 9.52 |
| Run 2 | 56.20 | 7.09 | 9.50 |

This nicotine mucate salt form deliquesced upon storage at 40° C./75%RH and 25° C./ 97%RH (6 days), melts at about126° C. and is soluble in water (>100 mg/ml at 50° C.). Representative XRPD peaks of the new salt form are provided below in Table 18.

TABLE 18

Characteristic XRPD pattern peaks of nicotine mucate sample

| Angle (2-Theta °) | Relative Intensity (%) |
|---|---|
| 8.1 | 11 |
| 9.2 | 32 |
| 10.2 | 35 |
| 10.8 | 8 |
| 13.0 | 9 |
| 13.6 | 11 |
| 15.2 | 34 |
| 15.5 | 100 |
| 16.1 | 35 |
| 17.1 | 78 |
| 19.4 | 67 |
| 19.7 | 34 |
| 20.0 | 33 |
| 20.5 | 14 |
| 20.9 | 26 |
| 21.7 | 82 |
| 23.6 | 15 |
| 24.4 | 12 |
| 25.1 | 29 |
| 26.7 | 36 |
| 27.7 | 24 |
| 28.9 | 15 |
| 29.9 | 25 |

Figure 16:
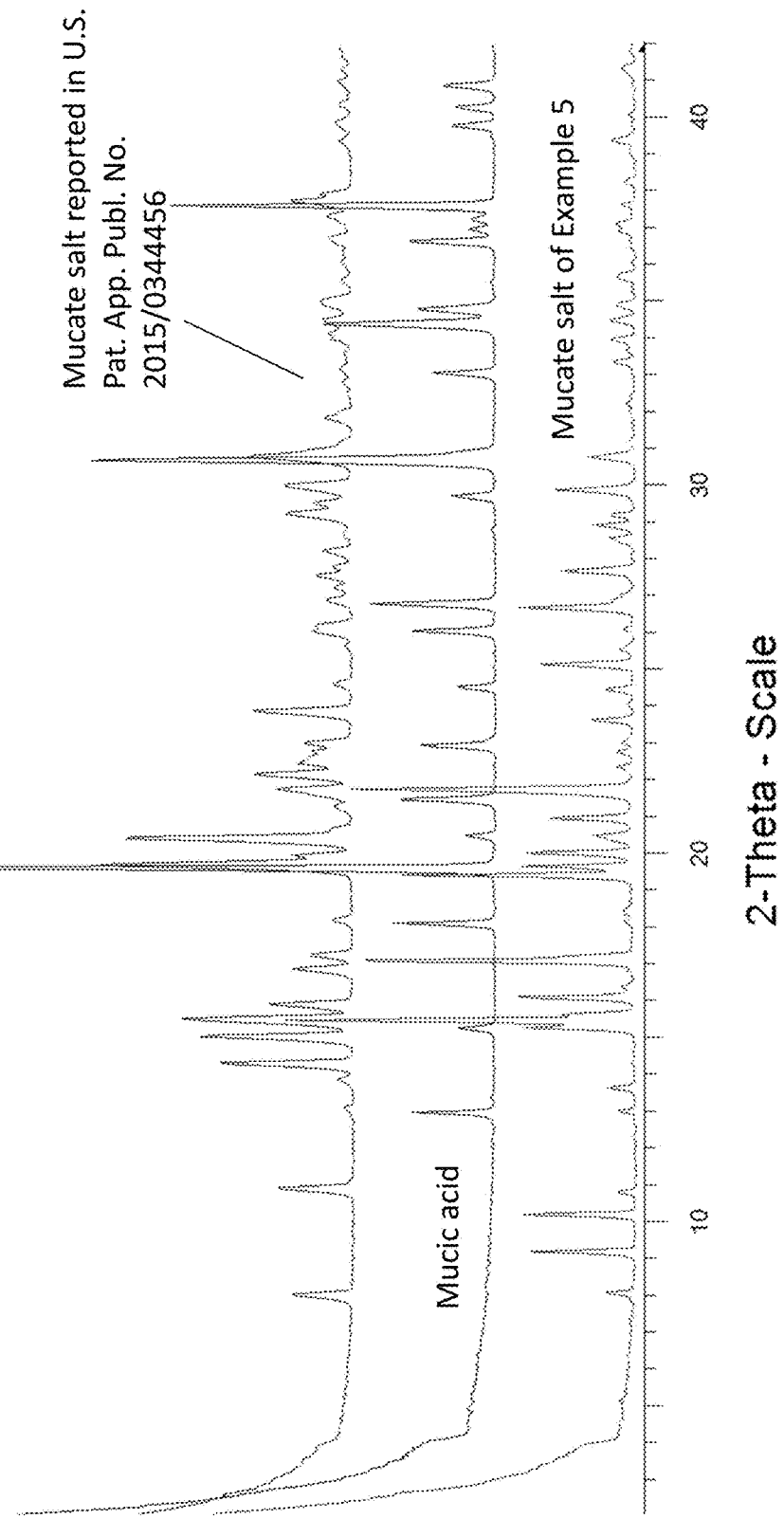
FIG. 16 is an XRPD pattern overlay of a nicotine mucate salt, compared with a previously reported mucate salt and reference input material.

Scale-up studies were conducted to investigate formation of the known nicotine mucate salt form (reported in US Pat. App. Publ. No. 2015/0344456) and it was found that the XRPD pattern reported therein was obtained in those instances where 4 equivalents of nicotine were added. Most other experiments yielded free mucic acid solids, suggesting that salt formation does not occur unless an excess of nicotine is used (with the excess nicotine remaining in liquid form). FIG. 16 provides a comparison of the XRPD pattern of the known nicotine mucate salt pattern previously reported and the new XPRD pattern identified herein. It is noted also that a single crystal x-ray structure was obtained for the known nicotine mucate salt pattern previously reported, as provided in FIG. 17. It was determined that the asymmetric unit contains two molecules of nicotinium and one molecule of mucate.

Example 6

Preparation and Analysis of Lozenges Containing Nicotine Salts and Salt Co-Crystals Lozenges were prepared incorporating: a) nicotine bitartrate dihydrate (control); b) nicotine mucate salt (as described in Example 5 herein); c) nicotine L-malate; and d) nicotine-L-malate (L-malic acid-succinic acid) (as described in Example 2 herein). Three lozenges were prepared with each nicotine source, and the lozenge weight averages were between 1.78 and 1.9 g. Each lozenge contained between 0.74 and 0.79 mg/g nicotine, i.e., from 1.36 to 1.44 mg nicotine (0.074-0.079% nicotine by weight). The lozenges generally contained, in addition to the nicotine source, a significant amount of isomalt (about 96% by weight), maltitol syrup (about 1% by weight), sodium chloride (about 1.4% by weight), sucralose (about 0.01% by weight), and water.

The lozenges were informally evaluated by 9 panelists who placed each lozenge type in his/her mouth and described the resulting sensory characteristics associated therewith. None of the lozenges evaluated in this study was found generally to provide significantly worse sensory characteristics based on generalizing the data from all nine panelists. The lozenge containing the (S)-nicotine mucate was described, e.g., as having a sweet/caramel taste, being "smooth," and "pleasant," "slightly salty." The lozenge containing the (S) nicotine L-malate (L-malic acid-succinic acid) salt-co-crystal was described, e.g., as having a salty and/or spicy note, being "warming" and "mild" and smooth/creamy.

Example 7

Pyrolysis Studies

The salt co-crystal of Example 2 ((S)-nicotine L-malate-(L-malic acid-succinic acid) salt co-crystal) and the salt of Example 5 (nicotine mucate) decompose when exposed to 650° C., liberating mostly nicotine as determined by GC/MS.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A salt-co-crystal of nicotine, L-malic acid, and succinic acid, characterized by an X-ray powder diffraction pattern having peaks at one or more of the following 2-theta diffraction angles: 17.1, 18.7, 20.0, 21.6, 25.1, and 25.4 wherein the salt-co-crystal has a stoichiometry of about 2:0.1:0.9 nicotine malate:L-malic acid:succinic acid.

2. The salt-co-crystal of claim 1, wherein the nicotine is (S)-nicotine.

3. The salt-co-crystal of claim 1, wherein at least about 50% of the salt or salt-co-crystal is in crystalline form.

4. The salt-co-crystal of claim 1, wherein at least about 80% of the salt is in crystalline form.

5. The salt-co-crystal of claim 1, wherein at least about 90% of the salt is in crystalline form.

6. The salt-co-crystal of claim 1, wherein the salt-co-crystal exhibits a melting point onset around 107° C.

7. The salt-co-crystal of claim 1, characterized by an X-ray powder diffraction pattern having peaks at two or more of the following 2-theta diffraction angles: 17.1, 18.7, 20.0, 21.6, 25.1, and 25.4.

8. The salt-co-crystal of claim 1, characterized by an X-ray powder diffraction pattern having peaks at three or more of the following 2-theta diffraction angles: 17.1, 18.7, 20.0, 21.6, 25.1, and 25.4.

9. The salt-co-crystal of claim 1, characterized by an X-ray powder diffraction pattern having peaks at four or more of the following 2-theta diffraction angles: 17.1, 18.7, 20.0, 21.6, 25.1, and 25.4.

10. The salt-co-crystal of claim 1, characterized by an X-ray powder diffraction pattern having peaks at five or more of the following 2-theta diffraction angles: 17.1, 18.7, 20.0, 21.6, 25.1, and 25.4.

11. The salt-co-crystal of claim 1, characterized by an X-ray powder diffraction pattern having peaks at all six of the following 2-theta diffraction angles: 17.1, 18.7, 20.0, 21.6, 25.1, and 25.4.

12. A method of preparing the salt-co-crystal of claim 1, comprising combining the nicotine, L-malic acid, and succinic acid to form the salt-co-crystal, and isolating the salt-co-crystal.

13. The method of claim 12, wherein the method comprises combining 1 equivalent of each of nicotine L-malate and succinic acid.

14. The method of claim 12, wherein the combining is done in a solvent.

15. The method of claim 14, wherein the solvent comprises acetone.

* * * * *